United States Patent
Foster et al.

(10) Patent No.: US 11,510,980 B2
(45) Date of Patent: Nov. 29, 2022

(54) BRARTEMICIN ANALOGUES

(71) Applicants: VICTORIA LINK LTD, Wellington (NZ); OSAKA UNIVERSITY, Osaka (JP)

(72) Inventors: Amy Jane Foster, Wellington (NZ); Bridget Louise Stocker, Wellington (NZ); Mattheus Simon Maria Timmer, Wellington (NZ); Sho Yamasaki, Shinsenri-higashimachi (JP)

(73) Assignees: VICTORIA LINK LTD., Wellington (NZ); OSAKA UNIVERSITY, Osaka (JP)

( * ) Notice: Subject to any disclaimer, the term of this patent is extended or adjusted under 35 U.S.C. 154(b) by 264 days.

(21) Appl. No.: 16/761,027

(22) PCT Filed: Nov. 2, 2018

(86) PCT No.: PCT/NZ2018/050156
§ 371 (c)(1),
(2) Date: May 1, 2020

(87) PCT Pub. No.: WO2019/088854
PCT Pub. Date: May 9, 2019

(65) Prior Publication Data
US 2021/0177965 A1 Jun. 17, 2021

(30) Foreign Application Priority Data
Nov. 2, 2017 (NZ) ........................ 736941

(51) Int. Cl.
*A61P 37/04* (2006.01)
*C07H 13/08* (2006.01)
*A61K 31/7024* (2006.01)
*A61K 39/39* (2006.01)
*C07H 15/18* (2006.01)

(52) U.S. Cl.
CPC .......... *A61K 39/39* (2013.01); *A61K 31/7024* (2013.01); *A61P 37/04* (2018.01); *C07H 13/08* (2013.01); *C07H 15/18* (2013.01)

(58) Field of Classification Search
None
See application file for complete search history.

(56) References Cited

U.S. PATENT DOCUMENTS

| 2011/0218171 A1* | 9/2011 | Nishizawa | C07H 13/08 514/53 |
| 2013/0331346 A1* | 12/2013 | Liu | C07H 13/08 514/25 |
| 2014/0248317 A1* | 9/2014 | Nishizawa | A61P 31/04 424/278.1 |

FOREIGN PATENT DOCUMENTS

| EP | 2351764 A1 | 8/2011 | |
| WO | WO-2019165114 A1 * | 8/2019 | ............. A61K 39/04 |

OTHER PUBLICATIONS

M. Rhia L. Stone, "Exploring the structure-activity relationship of Mincle ligands" A thesis submitted to Victoria University of Wellington In fulfillment of the requirements for the degree of Master of Science in Chemistry (Year: 2016).*

(Continued)

*Primary Examiner* — Eric Olson
(74) *Attorney, Agent, or Firm* — Polsinelli PC

(57) ABSTRACT

The invention relates to brartemicin analogues of Formula (IV) and their uses. These compounds are potent Mincle agonists and Th1-stimulating vaccine adjuvants.

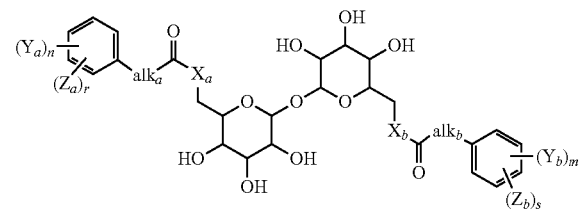

Formula IV

15 Claims, 6 Drawing Sheets

(56) References Cited

OTHER PUBLICATIONS

Figure 1:
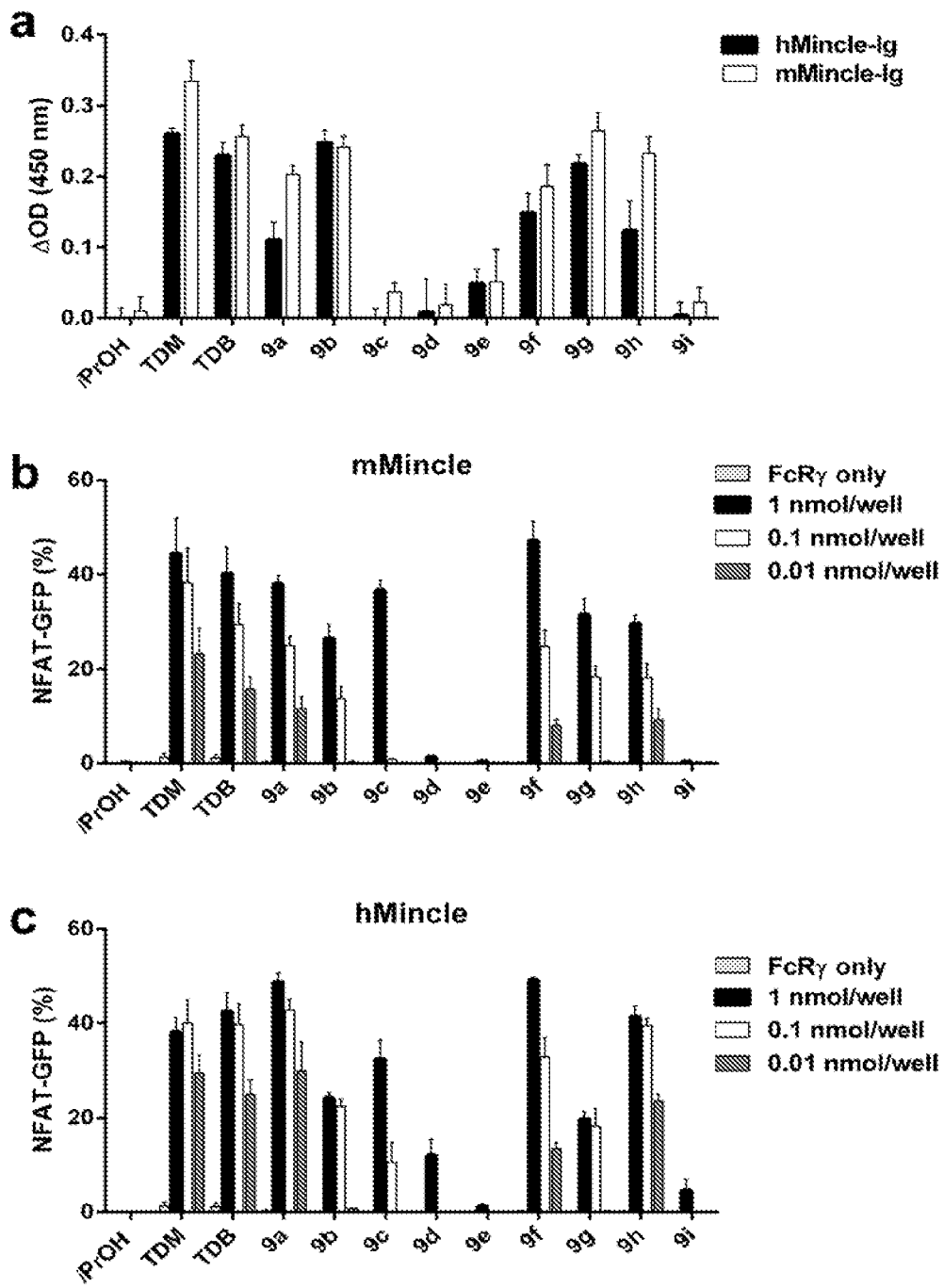

Penny et al., "The challenges for cancer chemoprevention" Chem. Soc. Rev., vol. 44 pp. 8836-8847, DOI: 10.1039/c5cs00705d (Year: 2015).*
Lee et al., "Mincle and STING-Stimulating Adjuvants Elicit Robust Cellular Immunity and Drive Long-Lasting Memory Responses in a Foot-and-Mouth Disease Vaccine" Frontiers in Immunology vol. 10:2509 DOI: 10.3389/fimmu.2019.02509 (Year: 2019).*
Braganza et al., "Identification and Biological Activity of Synthetic Macrophage Inducible C-Type Lectin Ligands" Frontiers in Immunology 8:1940 doi: 10.3389/fimmu.2017.01940 (Year: 2018).*
Olivera J. Finn, "The dawn of vaccines for cancer prevention" Nature Reviews Immunology vol. 18 pp. 183-194 doi:10.1038/nri. 2017.140 (Year: 2017).*
International Search Report and Written Opinion dated Feb. 1, 2019 for corresponding PCT Application No. PCT/NZ2018/050156.
International Preliminary Report on Patentability dated Aug. 5, 2019 for corresponding PCT Application No. PCT/NZ2018/050156.
Amy J. Foster et al., "Lipidated Brartemicin Analogues Are Potent Th1-Stimulating Vaccine Adjuvants", Journal Of Medicinal Chemistry, vol. 61, No. 3, 2018, pp. 1045-1060.
Avraham Liav et al., "Synthesis of 6,6'-di-O-acylated *,*-trehaloses via 2,3,4,2',3',4'-hexa-O-benzyl-*,*trehalose", Carbohydrate Research, vol. 81, No. 1, 1980, C1-C3, p. C2.
Avraham Liav et al., "Diamide pseudo cord-factors: bis-N-acyl derivatives of 6,6'-diamino-6,6'-dideoxy-*,*-trehalose", Carbohydrate Research, vol. 94, No. 2, 1980, 230-5, p. 231.
Hadar Feinberg et al., "Binding Sites for Acylated Trehalose Analogs of Glycolipid Ligands on an Extended Carbohydrate Recognition Domain of the Macrophage Receptor Mincle," The journal of Biological Chemistry, vol. 291, No. 40, 2016, pp. 21222-21233.

* cited by examiner

BRARTEMICIN ANALOGUES

CROSS-REFERENCE TO RELATED APPLICATIONS

This application is a national stage application (under 35 U.S.C. § 371) of PCT/NZ2018/050156, filed Nov. 2, 2018, which claims benefit of New Zealand Application No. 736941, filed Nov. 2, 2017, which are incorporated herein by reference in their entireties.

1. FIELD OF THE INVENTION

This invention relates generally to brartemicin analogues, pharmaceutical compositions comprising these and their uses.

2. BACKGROUND TO THE INVENTION

Adjuvants have traditionally been used to enhance the adaptive immune response to a vaccine, with most current vaccines providing protection primarily through humoral immunity. However, humoral immunity is insufficient to confer protection against some pathogens, thus necessitating the need for adjuvants that enhance acquired cellular (Th1) immunity. Th1 cells secrete cytokines which activate macrophages, inducing production of opsonizing antibodies by B cells. The Th1 response protects against invasive pathogens such as bacteria, protozoa, fungi and viruses. The Th1 response also activates cytotoxic T-lymphocytes (CTL), a sub-group of T cells that induce death of pathogen-infected cells. Natural killer (NK) cells are also activated by the Th1 response and play a major role in apoptosis in tumours and virus-infected cells.

Effective Th1-stimulating adjuvants often engage the innate immune system by activating pattern recognition receptors (PRRs) on professional antigen presenting cells (APCs). Previously, there has been much interest in the Toll-like receptors (TLRs) as targets for vaccine adjuvants. However more recently, Macrophage inducible C-type lectin (Mincle) has been identified as a PRR on the surface of macrophages and dendritic cells (DCs) and so is a promising new target for vaccine development.

Pathogen associated molecular patterns (PAMPs) are molecules associated with groups of pathogens that are recognised by cells of the innate immune system. A large number of molecules can act as PAMPs, including glycans and glycoconjugates. PAMPs bind to PRRs, with the specificity of the ensuing immune response being directed by the type of PRR activated and the structure of each specific PAMP.

Mincle is activated by a number of PAMPs including the *Mycobacterium tuberculosis* cell wall glycolipid trehalose dimycolate (TDM) with Mincle activation leading to the induction of the FcRγ-Syk-Card9-Bcl10-Malt1 signalling axis and a Th1-polarised immune response. A number of synthetically derived ligands also bind and activate Mincle, for example, trehalose dibehenate (TDB).

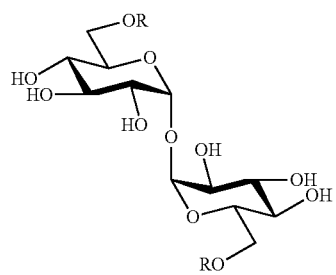

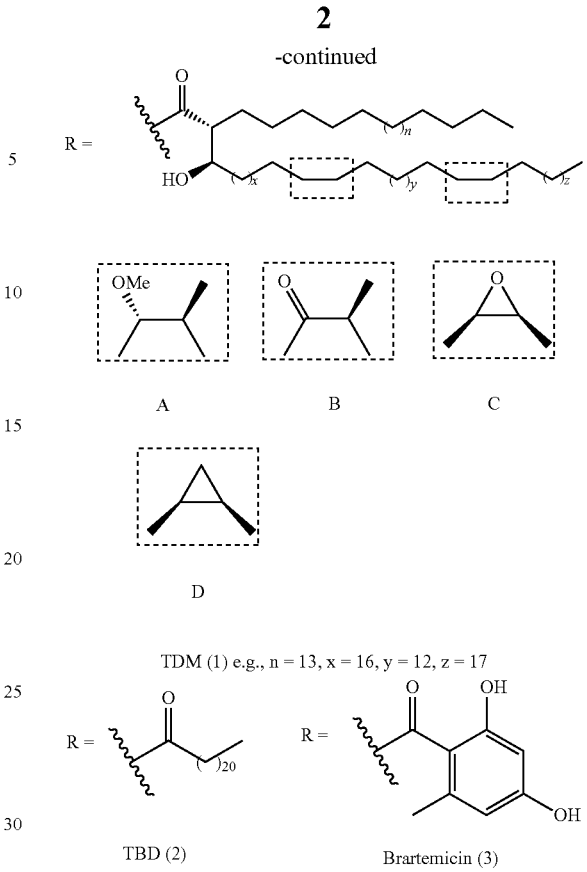

However, TDM is highly toxic so cannot be used as a therapeutic agent. It also comprises a complex mixture of compounds and is difficult to synthesise.

Accordingly, alternative Mincle agonists are needed, preferably compounds with high activity and low toxicity that are simple to prepare. It is an object of the invention to go at least some way towards providing an alternative Mincle agonist and/or a method of enhancing an immune response in a subject using such an alternative Mincle agonist and/or to provide at least one Th1-stimulating vaccine adjuvant and/or to at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

3. SUMMARY OF THE INVENTION

The inventors have surprisingly found that brartemicin analogues containing long lipophilic tails are potent Mincle agonists and Th1-stimulating vaccine adjuvants.

In one aspect the invention provides a compound of Formula I

Formula I

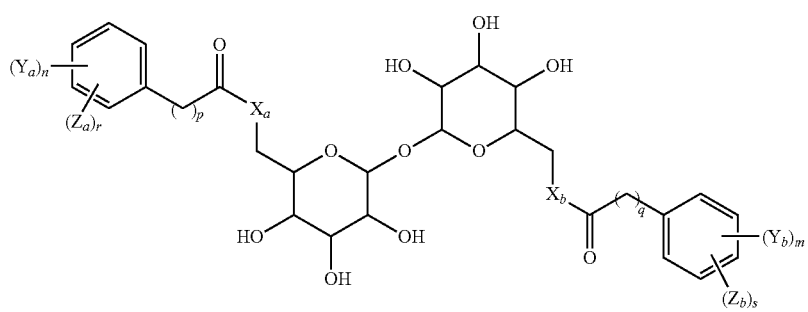

wherein $X_a$ and $X_b$ are independently selected from O or NH;

each $Y_a$ and $Y_b$ is independently selected from the group comprising —I, —Br, —Cl, —F, —OH, —$R^1$ and —$OR^1$ where $R^1$ is selected from ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl and ($C_2$-$C_6$)alkynyl are each optionally substituted with —OH or ($C_1$-$C_6$)alkoxy;

n and m are independently 0 to 4;

each $Z_a$ and $Z_b$ is independently selected from $R^2$, —$OR^2$, —$NHR^2$, —NHC(O)—$R^2$ and —S—$R^2$, where $R^2$ is selected from ($C_5$-$C_{26}$)alkyl, ($C_5$-$C_{26}$)alkenyl and ($C_5$-$C_{26}$)alkynyl, wherein ($C_5$-$C_{26}$)alkyl, ($C_5$-$C_{26}$)alkenyl and ($C_5$-$C_{26}$)alkynyl are each optionally substituted with —OH or ($C_1$-$C_6$)alkoxy;

r and s are independently 1 to 3;

p and q are independently 0 to 4;

wherein n+r=1 to 5; and m+s=1 to 5;

with the proviso that p and q are not both 3 when X is O, n and m are both 0, $Z_a$ and $Z_b$ are —$OR^2$ when $R^2$ is $C_{16}$-$C_{23}$ and r and s are both 1 or 2.

In another aspect the invention provides a compound of Formula Ia

Formula Ia

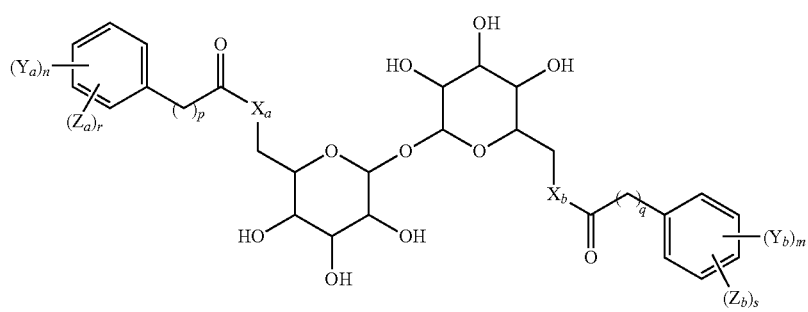

wherein $X_a$ and $X_b$ are independently selected from O or NH;

each $Y_a$ and $Y_b$ is independently selected from the group comprising —I, —Br, —Cl, —F, —OH, —$R^1$ and —$OR^1$ where $R^1$ is selected from ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl and ($C_2$-$C_6$)alkynyl are each optionally substituted with —OH or ($C_1$-$C_6$)alkoxy;

n and m are independently 0 to 4;

each $Z_a$ and $Z_b$ are independently selected from $R^2$, —$OR^2$, —$NHR^2$, —NHC(O)—$R^2$ and —S—$R^2$, where $R^2$ is selected from ($C_5$-$C_{26}$)alkyl, ($C_5$-$C_{26}$)alkenyl and ($C_5$-$C_{26}$)alkynyl, wherein ($C_5$-$C_{26}$)alkyl, ($C_5$-$C_{26}$)alkenyl and ($C_5$-$C_{26}$)alkynyl can be optionally substituted with —OH or ($C_1$-$C_6$)alkoxy;

r and s are independently 1 to 3;

p and q are independently 0 to 2;

wherein n+r=1 to 5; and m+s=1 to 5.

In another aspect the invention provides a compound of Formula Ib

Formula Ib

[Chemical structure of Formula Ib showing a disaccharide with two substituted phenyl-acetyl groups attached via $X_a$ and $X_b$ linkers, with $(Y_a)_n$, $(Z_a)_r$ on one aromatic ring and $(Y_b)_m$, $(Z_b)_s$ on the other]

wherein $X_a$, $X_b$, $Y_a$, $Y_b$, $Z_a$, $Z_b$, $R^1$, $R^2$, n, r, p, q, m and s are as defined for Formula I.

In another aspect the invention provides a compound of Formula Ib wherein $X_a$, $X_b$, $Y_a$, $Y_b$, $Z_a$, $Z_b$, $R^1$, $R^2$, n, r, p, q, m and s are as defined for Formula Ia.

In the above aspects of the invention, in one embodiment $X_a$ and $X_b$ are both O.

In another embodiment, $X_a$ and $X_b$ are both NH.

In another embodiment one of $X_a$ and $X_b$ is O and one is NH.

In another embodiment, n and m are both 0.

In another embodiment n and m are both 1 and $Y_a$ and $Y_b$ are independently selected from —OH and Me.

In another embodiment n and m are both 2 and $Y_a$ is —OH in one ortho position and Me in the other ortho position.

In one embodiment, s and r are both 1.

In one embodiment, $Z_a$ and $Z_b$ are both $OR^2$ wherein $R^2$ is $(C_5-C_{22})$alkyl, preferably $(C_7-C_{19})$alkyl.

In one embodiment, $Z_a$ and $Z_b$ are both $R^2$ wherein $R^2$ is $(C_5-C_{22})$alkyl, preferably $(C_7-C_{19})$alkyl.

In another aspect the invention provides a compound of Formula II n is 0 to 4;

each Z is independently selected from $R^2$, —$OR^2$, —$NHR^2$, —NHC(O)—$R^2$ and —S—$R^2$, where $R^2$ is selected from $(C_5-C_{26})$alkyl, $(C_5-C_{26})$alkenyl and $(C_5-C_{26})$alkynyl, wherein $(C_5-C_{26})$alkyl, $(C_5-C_{26})$alkenyl and $(C_5-C_{26})$alkynyl are each optionally substituted with —OH or $(C_1-C_6)$alkoxy;

r is 1 to 3;

p is 0 to 4;

wherein n+r=1 to 5;

with the proviso that p is not 3 when X is O, n is 0, Z is —$OR^2$ when $R^2$ is $C_{16}-C_{22}$ and r is 1 or 2.

In one embodiment X is O.

In another embodiment X is NH.

In another embodiment, n and m are both 0.

In another embodiment n and m are both 1 and Y is selected from —OH and Me.

In another embodiment n and m are both 2 and Y is-OH in one ortho position and Me in the other ortho position.

Formula II

[Chemical structure of Formula II showing a disaccharide with two substituted phenyl-acetyl groups attached via X linkers, with $(Y)_n$, $(Z)_r$ on each aromatic ring]

wherein X is selected from O or NH;

each Y is independently selected from the group comprising —I, —Br, —Cl, —F, —OH, —$R^1$ and —$OR^1$ where $R^1$ is selected from $(C_1-C_6)$alkyl, $(C_2-C_6)$alkenyl and $(C_2-C_6)$alkynyl, wherein $(C_1-C_6)$alkyl, $(C_2-C_6)$alkenyl and $(C_2-C_6)$alkynyl are each optionally substituted with —OH or $(C_1-C_6)$alkoxy;

In one embodiment, s and r are both 1.

In one embodiment, $Z_a$ and $Z_b$ are both $OR^2$ wherein $R^2$ is $(C_5-C_{22})$alkyl, preferably $(C_7-C_{19})$alkyl.

In one embodiment, $Z_a$ and $Z_b$ are both $R^2$ wherein $R^2$ is $(C_5-C_{22})$alkyl, preferably $(C_7-C_{19})$alkyl.

In another aspect the invention provides a compound of Formula III

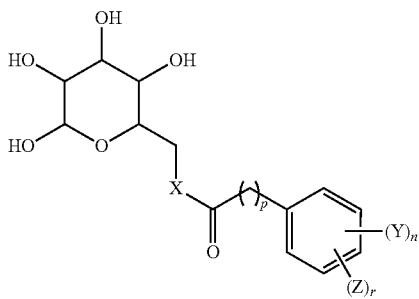

Formula III wherein X is selected from O or NH;

each Y is independently selected from the group comprising —I, —Br, —Cl, —F, —OH, —$R^1$ and —$OR^1$ where $R^1$ is selected from ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl and ($C_2$-$C_6$)alkynyl are each optionally substituted with —OH or ($C_1$-$C_6$)alkoxy;

n is 0 to 4;

each Z is independently selected from $R^2$, —$OR^2$, —$NHR^2$, —NHC(O)—$R^2$ and —S—$R^2$, where $R^2$ is selected from ($C_5$-$C_{26}$)alkyl, ($C_5$-$C_{26}$)alkenyl and ($C_5$-$C_{26}$)alkynyl, wherein ($C_5$-$C_{26}$)alkyl, ($C_5$-$C_{26}$)alkenyl and ($C_5$-$C_{26}$)alkynyl are each optionally substituted with —OH or ($C_1$-$C_6$)alkoxy;

r is 1 to 3;

p is 0 to 4;

wherein n+r=1 to 5.

In one embodiment X is O.

In one embodiment, Y is independently selected from —OH and Me.

In one embodiment, Z is $OR^2$ wherein $R^2$ is ($C_5$-$C_{22}$)alkyl, preferably ($C_7$-$C_{19}$)alkyl.

In one embodiment, Z is $R^2$ wherein $R^2$ is ($C_5$-$C_{22}$)alkyl, preferably ($C_7$-$C_{19}$)alkyl.

In another aspect the invention provides a compound of Formula IV

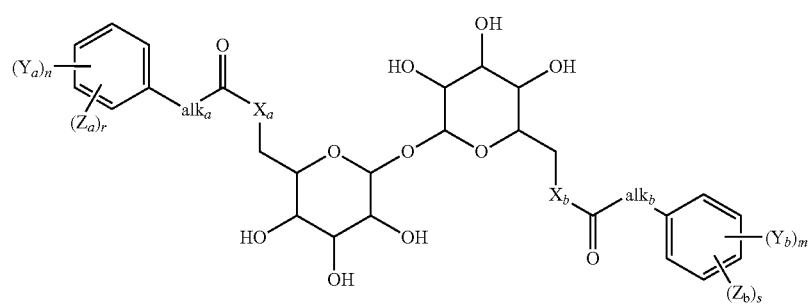

Formula IV wherein $X_a$ and $X_b$ are independently selected from O or NH;

each $Y_a$ and $Y_b$ is independently selected from the group comprising —I, —Br, —Cl, —F, —OH, —$R^1$ and —$OR^1$ where $R^1$ is selected from ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl and ($C_2$-$C_6$)alkynyl are each optionally substituted with —OH or ($C_1$-$C_6$)alkoxy;

n and m are independently 0 to 4;

each $Z_a$ and $Z_b$ is independently selected from $R^2$, —$OR^2$, —$NHR^2$, —NHC(O)—$R^2$ and —S—$R^2$, where $R^2$ is selected from ($C_5$-$C_{26}$)alkyl, ($C_5$-$C_{26}$)alkenyl and ($C_5$-$C_{26}$)alkynyl, wherein ($C_5$-$C_{26}$)alkyl, ($C_5$-$C_{26}$)alkenyl and ($C_5$-$C_{26}$)alkynyl are each optionally substituted with —OH or ($C_1$-$C_6$)alkoxy;

r and s are independently 1 to 3;

$alk_a$ and $alk_b$ are independently selected from ($C_1$-$C_4$)alkylene, ($C_2$-$C_4$)alkenylene and ($C_2$-$C_4$)alkynylene or each $alk_a$ and $alk_b$ may be absent such that the aryl ring connects directly to the C(O) carbon;

wherein n+r=1 to 5; and m+s=1 to 5;

with the proviso that $alk_a$ and $alk_b$ are not both $C_3$ alkylene when X is O, n and m are both 0, $Z_a$ and $Z_b$ are —$OR^2$ when $R^2$ is $C_{16}$-$C_{23}$ and r and s are both 1 or 2.

In another aspect the invention provides a compound of Formula IVa

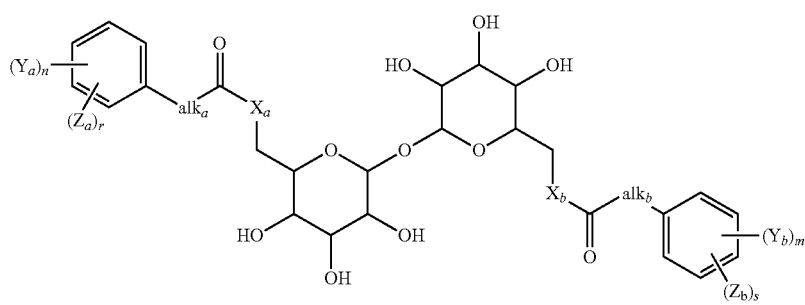

Formula IVa wherein $X_a$ and $X_b$ are independently selected from O or NH;

each $Y_a$ and $Y_b$ is independently selected from the group comprising —I, —Br, —Cl, —F, —OH, —$R^1$ and —$OR^1$ where $R^1$ is selected from $(C_1$-$C_6)$alkyl, $(C_2$-$C_6)$alkenyl and $(C_2$-$C_6)$alkynyl, wherein $(C_1$-$C_6)$alkyl, $(C_2$-$C_6)$alkenyl and $(C_2$-$C_6)$alkynyl are each optionally substituted with —OH or $(C_1$-$C_6)$alkoxy;

n and m are independently 0 to 4;

each $Z_a$ and $Z_b$ is independently selected from $R^2$, —$OR^2$, —$NHR^2$, —NHC(O)—$R^2$ and —S—$R^2$, where $R^2$ is selected from $(C_5$-$C_{26})$alkyl, $(C_5$-$C_{26})$alkenyl and $(C_5$-$C_{26})$alkynyl, wherein $(C_5$-$C_{26})$alkyl, $(C_5$-$C_{26})$alkenyl and $(C_5$-$C_{26})$alkynyl are each optionally substituted with —OH or $(C_1$-$C_6)$alkoxy;

r and s are independently 1 to 3;

$alk_a$ and $alk_b$ are independently selected from $(C_1$-$C_4)$alkylene, $(C_2$-$C_4)$alkenylene and $(C_2$-$C_4)$alkynylene or each $alk_a$ and $alk_b$ may be absent such that the aryl ring connects directly to the C(O) carbon;

wherein n+r=1 to 5; and m+s=1 to 5.

In another aspect the invention provides a compound of Formula IVb wherein $X_a$, $X_b$, $Y_a$, $Y_b$, $Z_a$, $Z_b$, $R^1$, $R^2$, n, r, $alk_a$ and $alk_b$, m and s are as defined for Formula IV.

In another aspect the invention provides a compound of Formula Ib wherein $X_a$, $X_b$, $Y_a$, $Y_b$, $Z_a$, $Z_b$, $R^1$, $R^2$, n, r, $alk_a$ and $alk_b$, m and s are as defined for Formula IVa.

In the above aspects of the invention, in one embodiment $X_a$ and $X_b$ are both O.

In another embodiment, $X_a$ and $X_b$ are both NH.

In another embodiment one of $X_a$ and $X_b$ is O and one is NH.

In another embodiment, n and m are both 0.

In another embodiment n and m are both 1 and $Y_a$ and $Y_b$ are independently selected from —OH and Me.

In another embodiment n and m are both 2 and $Y_a$ is -OH in one ortho position and Me in the other ortho position.

In one embodiment, s and r are both 1.

In one embodiment, $alk_a$ and $alk_b$ are independently selected from $(C_1$-$C_4)$alkylene and $(C_2$-$C_4)$alkenylene, preferably $(C_1$-$C_4)$alkylene.

In one embodiment, $Z_a$ and $Z_b$ are both $OR^2$ wherein $R^2$ is $(C_5$-$C_{22})$alkyl, preferably $(C_7$-$C_{19})$alkyl.

In one embodiment, $Z_a$ and $Z_b$ are both $R^2$ wherein $R^2$ is $(C_5$-$C_{22})$alkyl, preferably $(C_7$-$C_{19})$alkyl.

In another aspect the invention provides a compound of Formula V

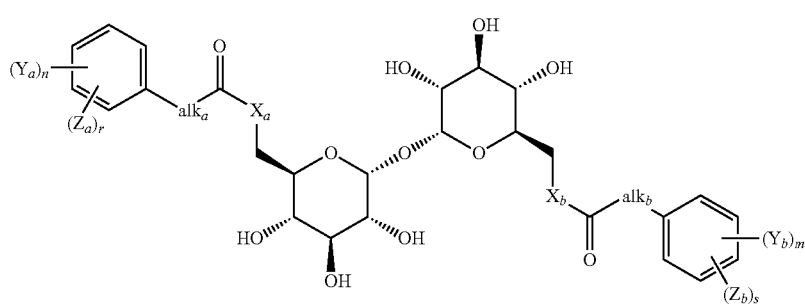

Formula IVb

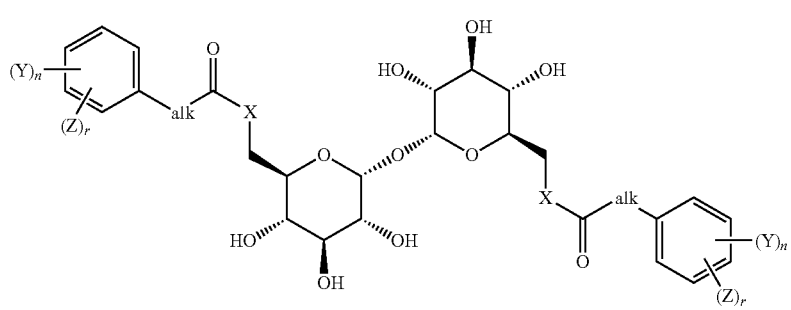

Formula V wherein X is selected from O or NH;

each Y is independently selected from the group comprising —I, —Br, —Cl, —F, —OH, —$R^1$ and —$OR^1$ where $R^1$ is selected from ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl and ($C_2$-$C_6$)alkynyl are each optionally substituted with —OH or ($C_1$-$C_6$)alkoxy;

n is 0 to 4;

each Z is independently selected from $R^2$, —$OR^2$, —$NHR^2$, —NHC(O)—$R^2$ and —S—$R^2$, where $R^2$ is selected from ($C_5$-$C_{26}$)alkyl, ($C_5$-$C_{26}$)alkenyl and ($C_5$-$C_{26}$)alkynyl, wherein ($C_5$-$C_{26}$)alkyl, ($C_5$-$C_{26}$)alkenyl and ($C_5$-$C_{26}$)alkynyl are each optionally substituted with —OH or ($C_1$-$C_6$)alkoxy;

r is 1 to 3;

alk is selected from ($C_1$-$C_4$)alkylene, ($C_2$-$C_4$)alkenylene and ($C_2$-$C_4$)alkynylene or alk may be absent such that the aryl ring connects directly to the C(O) carbon;

wherein n+r=1 to 5;

with the proviso that p is not 3 when X is O, n is 0, Z is —$OR^2$ when $R^2$ is $C_{16}$-$C_{22}$ and r is 1 or 2.

In one embodiment X is O.

In another embodiment X is NH.

In another embodiment, n and m are both 0.

In another embodiment n and m are both 1 and Y is selected from —OH and Me.

In another embodiment n and m are both 2 and Y is-OH in one ortho position and Me in the other ortho position.

In one embodiment, s and r are both 1.

In one embodiment, alk is ($C_1$-$C_4$)alkylene or ($C_2$-$C_4$)alkenylene, preferably ($C_1$-$C_4$)alkylene.

In one embodiment, $Z_a$ and $Z_b$ are both $OR^2$ wherein $R^2$ is ($C_5$-$C_{22}$)alkyl, preferably ($C_7$-$C_{19}$)alkyl.

In another embodiment, $Z_a$ and $Z_b$ are both $R^2$ wherein $R^2$ is ($C_5$-$C_{22}$)alkyl, preferably ($C_7$-$C_{19}$)alkyl.

In another aspect the invention provides a compound of Formula VI

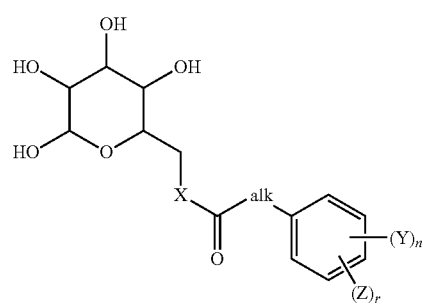

Formula VI wherein X is selected from O or NH;

each Y is independently selected from the group comprising —I, —Br, —Cl, —F, —OH, —$R^1$ and —$OR^1$ where $R^1$ is selected from ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl and ($C_2$-$C_6$)alkynyl are each optionally substituted with —OH or ($C_1$-$C_6$)alkoxy;

n is 0 to 4;

each Z is independently selected from $R^2$, —$OR^2$, —$NHR^2$, —NHC(O)—$R^2$ and —S—$R^2$, where $R^2$ is selected from ($C_5$-$C_{26}$)alkyl, ($C_5$-$C_{26}$)alkenyl and ($C_5$-$C_{26}$)alkynyl, wherein ($C_5$-$C_{26}$)alkyl, ($C_5$-$C_{26}$)alkenyl and ($C_5$-$C_{26}$)alkynyl are each optionally substituted with —OH or ($C_1$-$C_6$)alkoxy;

r is 1 to 3;

alk is selected from ($C_1$-$C_4$)alkylene, ($C_2$-$C_4$)alkenylene and ($C_2$-$C_4$)alkynylene or alk may be absent such that the aryl ring connects directly to the C(O) carbon;

wherein n+r=1 to 5.

In one embodiment X is O.

In one embodiment, Y is independently selected from —OH and Me.

In one embodiment, alk is $(C_1-C_4)$alkylene and $(C_2-C_4)$ alkenylene, preferably $(C_1-C_4)$alkylene.
In one embodiment, Z is $OR^2$ wherein $R^2$ is $(C_5-C_{22})$alkyl, preferably $(C_7-C_{19})$alkyl.
In one embodiment, Z is $R^2$ wherein $R^2$ is $(C_5-C_{22})$alkyl, preferably $(C_7-C_{19})$alkyl.
In another aspect the invention provides a compound selected from the group consisting of
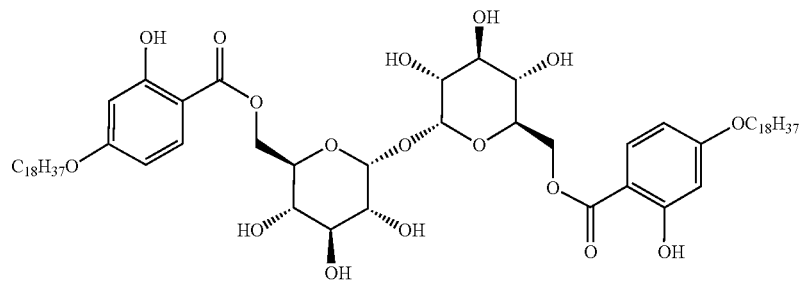
9a
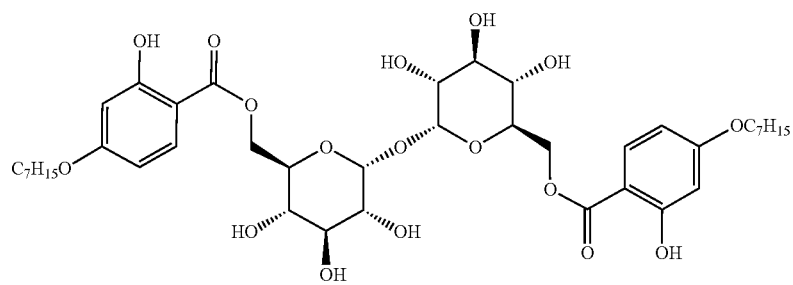
9b
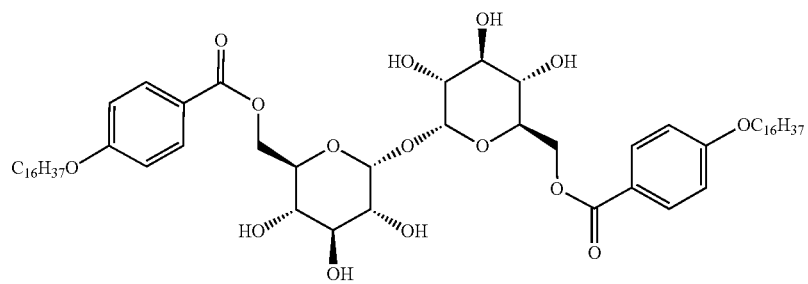
9f
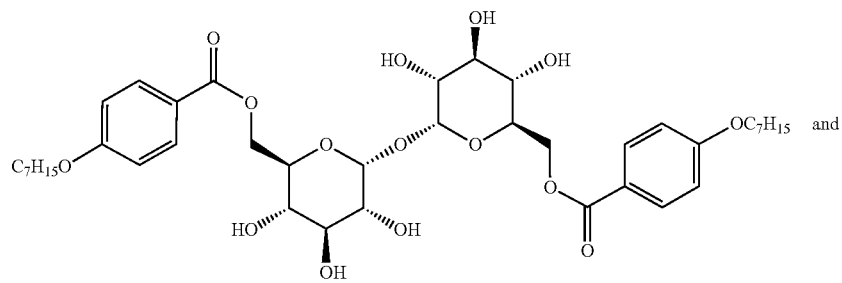
9g and
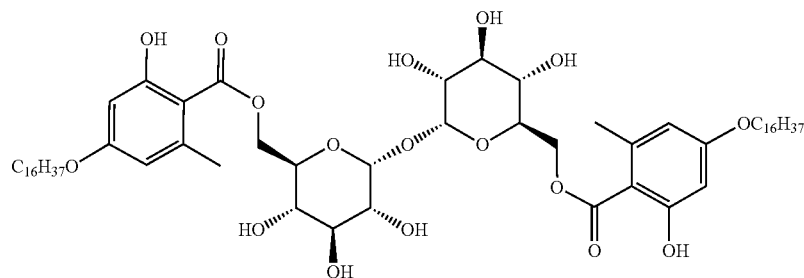
9h In another aspect the invention provides a compound selected from the group consisting of
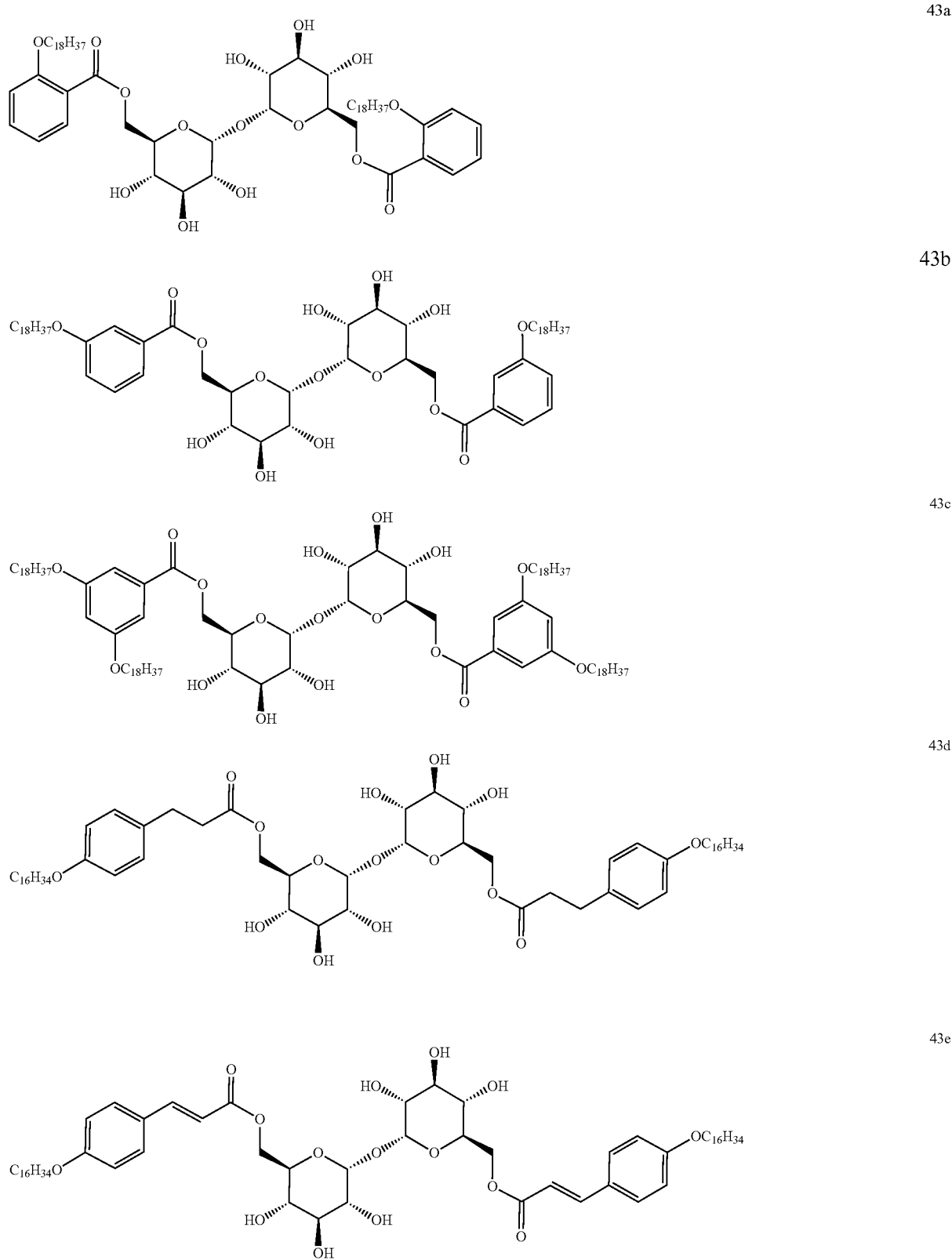

-continued
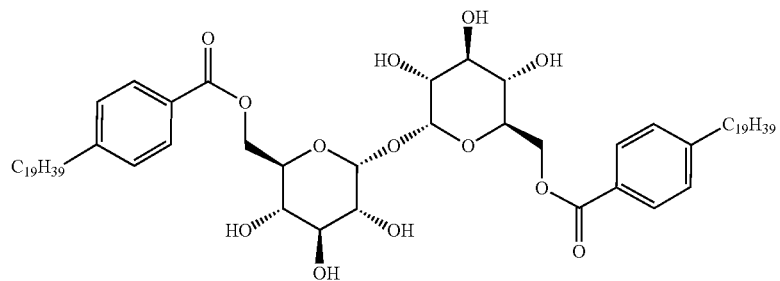
43f
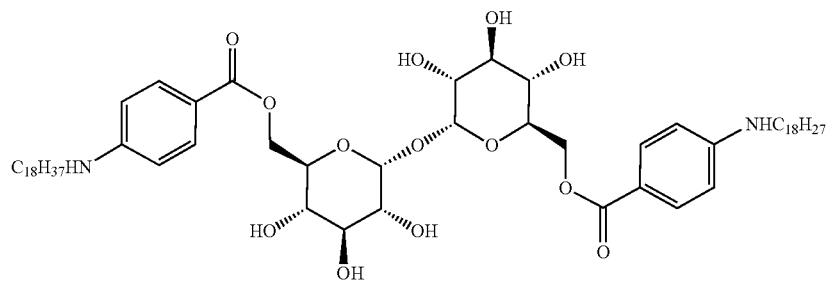
43g
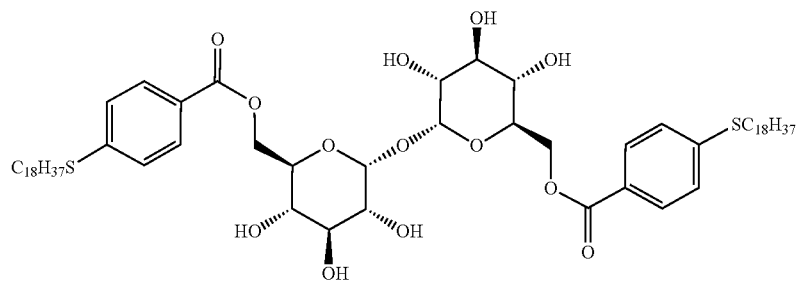
43h
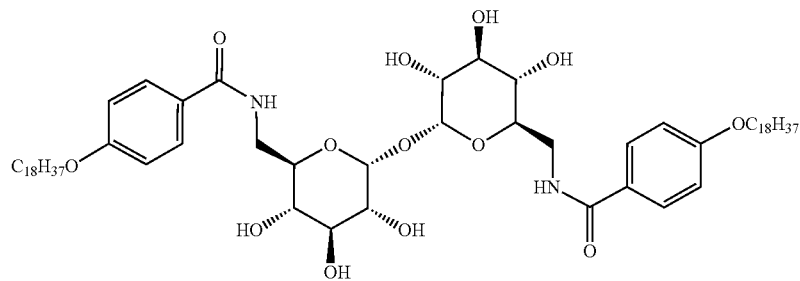
43i
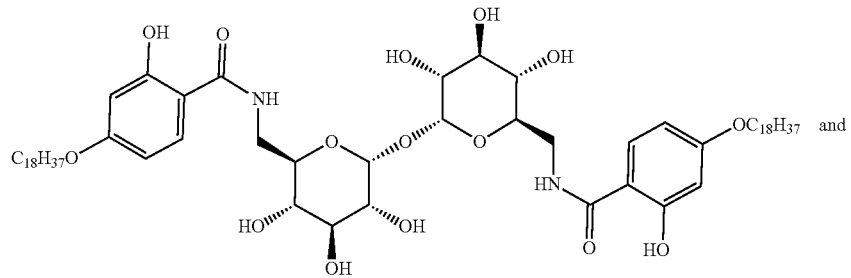
43j
and

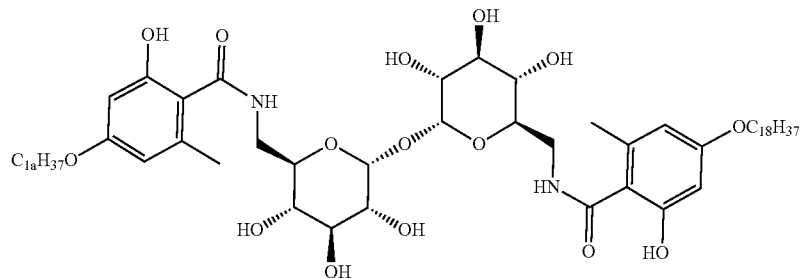

43k

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Other aspects of the invention may become apparent from the following description which is given by way of example only and with reference to the accompanying drawings.

4. BRIEF DESCRIPTION OF THE FIGURES

The invention will now be described with reference to the figures in the accompanying drawings.

FIG. 1 shows the compounds of the invention binding and signaling through mMincle and hMincle: (FIG. 1*a*) Plates coated with brartemicin analogues (0.1 nmol/well) were incubated with Ig-mMincle, Ig-hMincle, or Ig-only and ligand bound protein was detected via ELISA. Data is representative of three independent experiments performed in triplicate (mean±SD). (FIG. 1*b*) NFAT-GFP 2B4 reporter cells expressing mMincle+FcRγ or (FIG. 1*c*) hMincle+FcRγ were stimulated using ligand coated plates (0.01, 0.1, or 1 nmol/well) for 18 hours. The reporter cells were harvested and examined for NFAT-GFP expression. Data represents the mean of three independent experiments performed in duplicate (mean±SEM).

Figure 2:
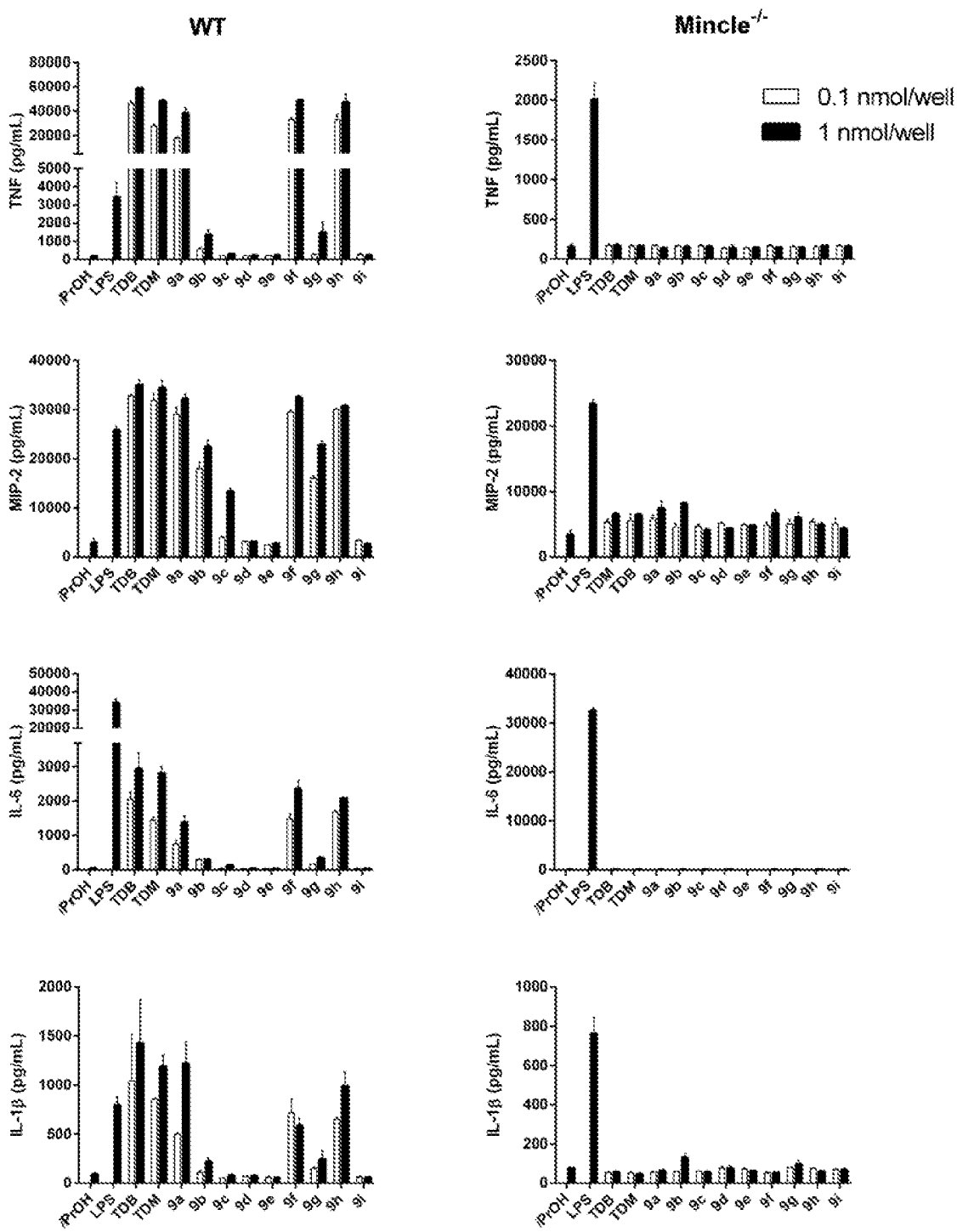

FIG. 2 shows the brartemicin analogues of the invention induce Mincle dependent inflammatory cytokine production: TNF, MIP-2, IL-6 and IL-1β production by harvested wild-type or Mincle−/− GM-CSF BMDMs treated with brartemicin derivatives. Harvested GM-CSF BMDMs were stimulated using TDB, TDM, or brartemicin derivative-coated plates (0.1 or 1 nmol/well) or solubilised LPS (100 ng/mL). Cytokine production was measured by ELISA from the supernatant collected after 24 hours. Data is representative of three independent experiments performed in triplicate (±SD).

Figure 3:
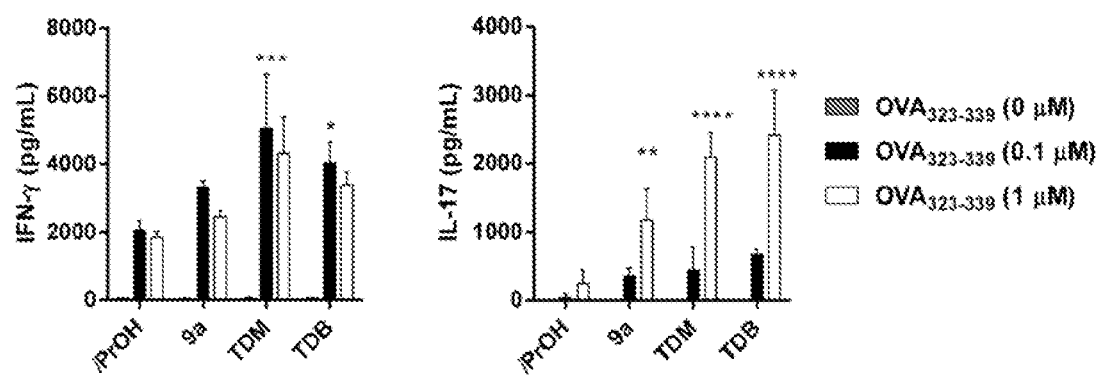

FIG. 3 shows that compound 9a displays adjuvant activity in vitro. OT-II CD4+ T-cells were co-cultured with GM-CSF BMDMs in the presence of TDM (0.1 nmol/well), TDB (0.1 nmol/well), 9a (0.1 nmol/well) and OVA323-339 peptide (0, 0.1, and 1 µM). After 48 hours, the supernatant was collected and levels of IFN-γ and IL-17 were measured using ELISA. Data is representative of two experiments performed in triplicate (mean±SD). *P≤0.05; P≤0.01; *P≤0.005; ****P≤0.001.

Figure 4:
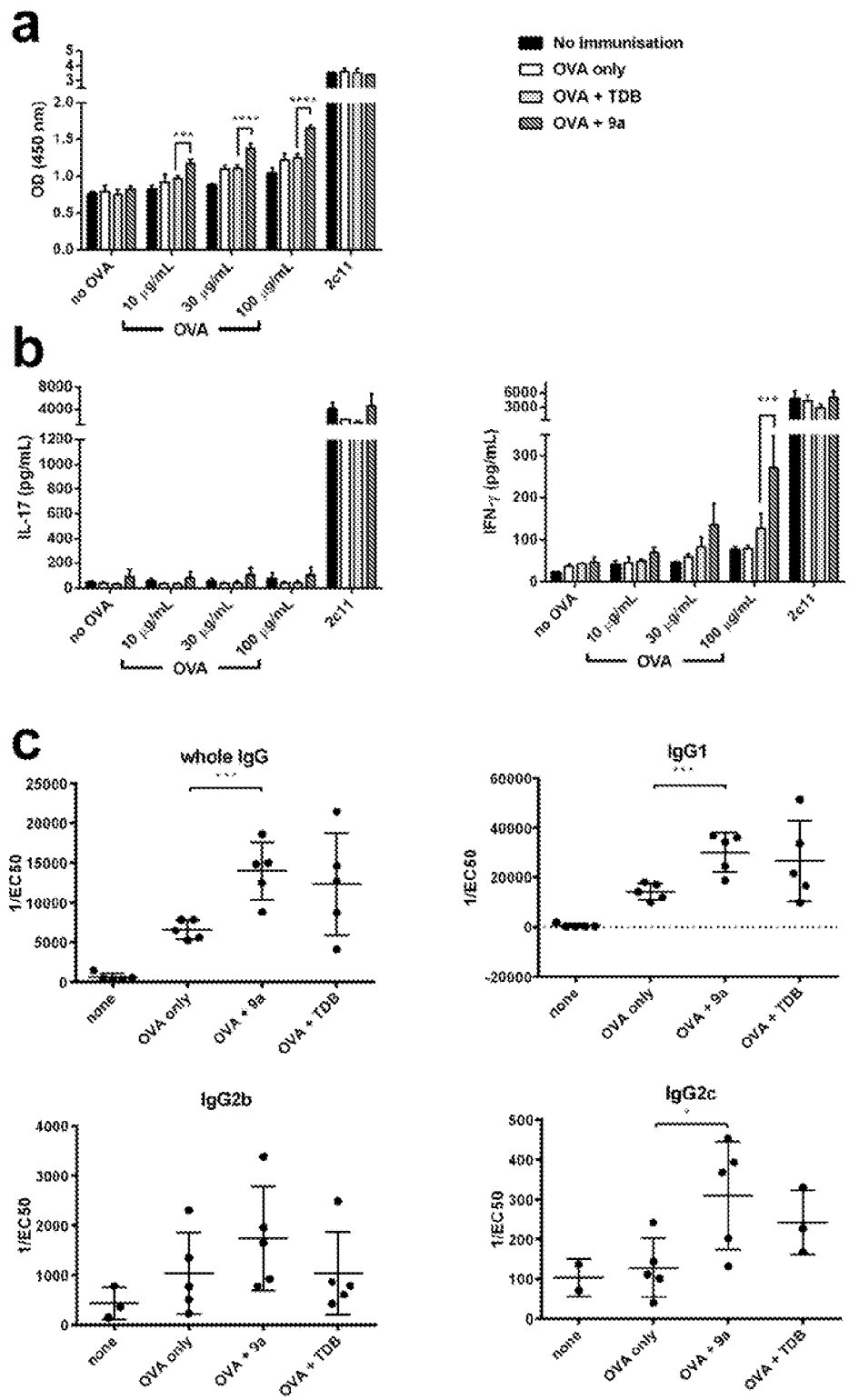

FIG. 4 shows that compound 9a displays potent adjuvant activity in vivo. C57BL/6 mice (n=5 per group) were immunised subcutaneously with oil-in-water emulsions containing OVA only (200 µg), OVA+TDB (OVA=200 µg, TDB=0.3 µmol) OVA+9a (OVA=200 µg, 9a=0.3 µmol), or emulsion only. After seven days, the mice were challenged with OVA (100 µg/footpad). After a further seven days, the mice were sacrificed, blood samples taken, and their spleens were harvested. Total splenocyte number (FIG. 4*a*) and cytokine production (FIG. 4*b*) were measured following restimulation with OVA. Blood serum was analysed for OVA-specific antibody production (FIG. 4*c*). *P≤0.05; P≤0.01; *P≤0.005; ****P≤0.001.

Figure 5:
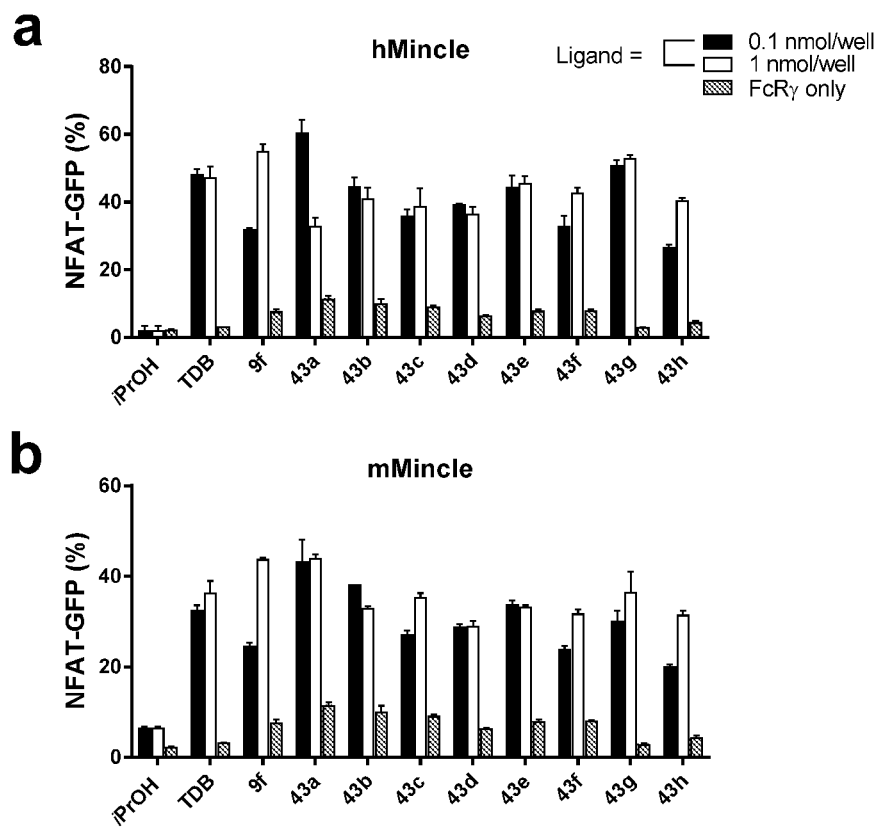

FIG. 5 shows compounds 43a-43h and 9f of the binding and signalling through mMincle and hMincle: (FIG. 5) NFAT-GFP 2B4 reporter cells expressing hMincle+FcRγ (FIG. 5*a*) or mMincle+FcRγ (FIG. 5*b*) were incubated in plates coated with TDB, 9f, and analogues 43a-43h (0.1 and 1 nmol/well) for 20 hours. The 2B4 reporter cells were then harvested and examined for NFAT-GFP expression using flow cytometry. Data is representative of two independent experiments performed in duplicate (mean±SD).

Figure 6:
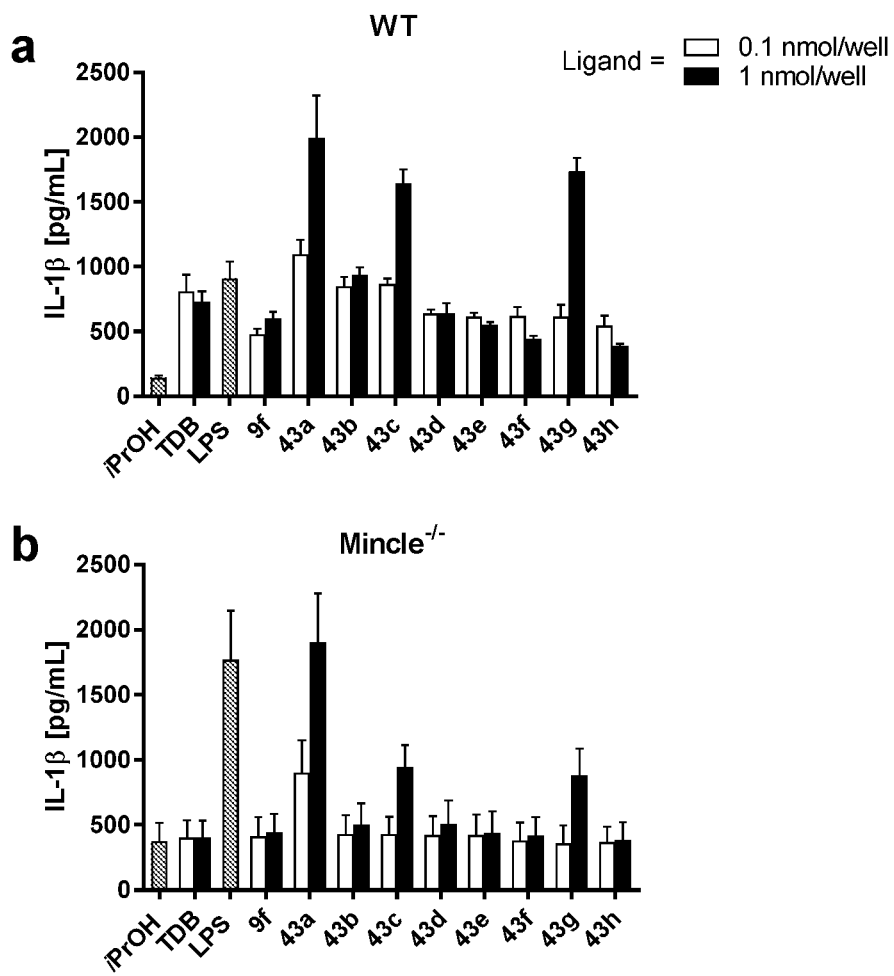

FIG. 6 shows compounds 43a-43h and 9f of the induce IL-1β production. Harvested GM-CSF BMDMs were stimulated using plates coated with TDB, derivative 9f, brartemicin derivatives 43a-43h (0.1 or 1 nmol/well), or solubilised LPS (100 ng/mL). Cytokine production was measured by ELISA from the supernatant collected after 24 hours. Data represents the mean of three independent experiments performed in duplicate (mean±SD).

5. DETAILED DESCRIPTION OF THE INVENTION

5.1 Definitions

The following definitions are presented to better define the present invention and as a guide for those of ordinary skill in the art in the practice of the present invention.

The term "alkyl" means any saturated hydrocarbon radical having up to 30 carbon atoms and includes any $C_1$-$C_{26}$, $C_1$-$C_{22}$, $C_1$-$C_{18}$, $C_1$-$C_{10}$, or $C_1$-$C_7$ alkyl group, and is intended to include cyclic (including fused bicyclic) alkyl groups (sometimes referred to herein as "cycloalkyl"), straight-chain and branched-chain alkyl groups, and straight or branched chain alkyl groups substituted with cyclic alkyl groups. Examples of alkyl groups include: methyl group, ethyl group, n-propyl group, /so-propyl group, cyclopropyl group, n-butyl group, /so-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, cyclohexyl group, cyclooctyl group, and 1-methyl-2-ethylpropyl group.

The term "alkylene" means a diradical corresponding to an alkyl group. Examples of alkylene groups include methylene group, cyclohexylene group, ethylene group. An alkylene group can incorporate one or more cyclic alkylene group(s) in the alkylene chain, for example, "alkylene" can include a cyclohexylene group attached to a methylene group. Any alkylene group may be optionally substituted with one or more substituents selected from the group consisting of hydroxyl, halogen, e.g. fluorine, alkyl, e.g. methyl, and aryl. Any alkylene may optionally include one or more arylene moieties within the alkylene chain, for example, a phenylene group may be included within an alkylene chain.

The term "alkenyl" means any hydrocarbon radical having at least one double bond, and having up to 30 carbon atoms, and includes any $C_2$-$C_{26}$, $C_2$-$C_{22}$, $C_2$-$C_{18}$, $C_2$-$C_{10}$, or $C_2$-$C_7$, alkenyl group, and is intended to include both straight- and branched-chain alkenyl groups. Examples of alkenyl groups include: ethenyl group, n-propenyl group, iso-propenyl group, n-butenyl group, iso-butenyl group, sec-butenyl group, f-butenyl group, n-pentenyl group, 1,1-dimethylpropenyl group, 1,2-dimethylpropenyl group, 2,2-dimethylpropenyl group, 1-ethylpropenyl group, 2-ethylpropenyl group, n-hexenyl group and 1-methyl-2-ethylpropenyl group.

The term "alkenylene" means a diradical corresponding to an alkene group. Any alkylene group may be optionally substituted with one or more substituents selected from the group consisting of hydroxyl, halogen, e.g. fluorine, alkyl, e.g. methyl, and aryl. Any alkylene may optionally include one or more arylene moieties within the alkylene chain, for example, a phenylene group may be included within an alkylene chain.

The term "alkynyl" means any hydrocarbon radical having at least one triple bond, and having up to 30 carbon atoms, and includes any $C_2$-$C_{26}$, $C_2$-$C_{22}$, $C_2$-$C_{18}$, $C_2$-$C_{10}$, or $C_2$-$C_7$, alkenyl group, and is intended to include both straight- and branched-chain alkenyl groups. Examples of alkenyl groups include: ethynyl group, n-propynyl group, iso-propynyl group, n-butynyl group, iso-butynyl group, sec-butynyl group, f-butynyl group, n-pentynyl group and the like.

The term "alkynylene" means a diradical corresponding to an alkynyl group. Any alkynylene group may be optionally substituted with one or more substituents selected from the group consisting of hydroxyl, halogen, e.g. fluorine, alkyl, e.g. methyl, and aryl. Any alkylene may optionally include one or more arylene moieties within the alkylene chain, for example, a phenylene group may be included within an alkylene chain.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "alkoxy" means an O-alkyl group, where alkyl as defined above.

The term "acyl" means C(=O)R' group, where R' is alkyl as defined above.

The term "acyloxy" means OR" group, where R" is acyl as defined above.

The term "amide" includes both N-linked (—NHC(O)R) and C-linked (—C(O)NHR) amides.

The term "antigen" refers to any substance capable of inducing a specific immune response and of reacting with the products of that response. Antigens may be molecules such as toxins and proteins, or parts of bacteria and/or tissue cells.

The term "immunologic adjuvant" means a substance that, when incorporated into, or administered in conjunction with, a vaccine composition, acts to accelerate, prolong or enhance the antigen-specific immune response to the vaccine.

The term "pharmaceutically acceptable excipient" means a carrier, diluent or vehicle with which the therapeutic is administered, that is not unduly toxic. Pharmaceutically acceptable excipients have been approved by relevant government regulatory agencies. Excipients include but are not limited to sterile liquids such as water and oils, including animal, vegetable, synthetic or petroleum oils, saline solutions, aqeuous dextrose and glycerol solutions, starch glucose, lactose, sucrose, gelatin, sodium stearate, glycerol monostearate, sodium chloride, propylene glycol, ethanol, wetting agents, emulsifying agents, binders, dispersants, thickeners, lubricants, pH adjusters, solubilizers, softening agents, surfactants and the like. The compositions of the invention can take the form of solutions, suspensions, emulsions, tablets, pills, capsules, powders and sustained-release formulations. Examples of suitable pharmaceutical excipients are described in Remington's Pharmaceutical Sciences $18^{th}$ Ed., Gennaro, ed. (Mack Publishing Co. 1990).

The pharmaceutically acceptable excipient is present in a composition of the invention in an amount that does not impair the activity of the compound of the invention.

As used herein, the term "substituted" is intended to mean that one or more hydrogen atoms in the group indicated is replaced with one or more independently selected suitable substituents, provided that the normal valency of each atom to which the substituent/s are attached is not exceeded, and that the substitution results in a stable compound. Suitable substituents include the optional substituents indicated herein.

Asymmetric or chiral centers may exist in the compounds of the invention. Asymmetric or chiral centers may be designated as (R) or (S), depending on the configuration of substituents in three dimensional space at the chiral atom. All stereochemical isomeric forms of the compounds, including diastereomeric, enantiomeric, and epimeric forms, as well as d-isomers and l-isomers, and mixtures thereof, including enantiomerically enriched and diastereomerically enriched mixtures of stereochemical isomers, are included herein.

Individual enantiomers can be prepared synthetically from commercially available enantiopure starting materials or by preparing enantiomeric mixtures and resolving the mixture into individual enantiomers. Resolution methods include conversion of the enantiomeric mixture into a mixture of diastereomers and separation of the diastereomers by, for example, recrystallization or chromatography, and any other appropriate methods known in the art. Starting materials of defined stereochemistry may be commercially available or made and, if necessary, resolved by techniques well known in the art.

The compounds of the invention may also exist as conformational or geometric stereoisomers, including cis, trans, syn, anti, entgegen (E), and zusammen (Z) isomers. All such stereoisomers and any mixtures thereof are within the scope of the invention. Also within the scope of the invention are any tautomeric isomers or mixtures thereof of the compounds of the invention. As would be appreciated by those skilled in the art, a wide variety of functional groups and other structures may exhibit tautomerism. Examples include, but are not limited to, keto/enol, imine/enamine, and thioketone/enethiol tautomerism.

The compounds of the invention may also exist as isotopologues and isotopomers, wherein one or more atoms in the compounds are replaced with different isotopes. Suitable isotopes include, for example, 1H, 2H (D), 3H (T), 12C, 13C, 14C, 16O, and 18O. Procedures for incorporating such isotopes into the compounds will be apparent to those skilled in the art. Isotopologues and isotopomers of the compounds are also within the scope of the invention.

Also within the scope of the invention are pharmaceutically acceptable salts of the compounds of the invention. Such salts include, acid addition salts, base addition salts, and quaternary salts of basic nitrogen-containing groups.

Acid addition salts can be prepared by reacting compounds, in free base form, with inorganic or organic acids. Examples of inorganic acids include, but are not limited to, hydrochloric, hydrobromic, nitric, sulfuric, and phosphoric acid. Examples of organic acids include, but are not limited to, acetic, trifluoroacetic, propionic, succinic, glycolic, lactic, malic, tartaric, citric, ascorbic, maleic, fumaric, pyruvic, aspartic, glutamic, stearic, salicylic, methanesulfonic, benzenesulfonic, isethionic, sulfanilic, adipic, butyric, and pivalic. Base addition salts can be prepared by reacting compounds, in free acid form, with inorganic or organic bases. Examples of inorganic base addition salts include alkali metal salts, alkaline earth metal salts, and other physiologically acceptable metal salts, for example, aluminium, calcium, lithium, magnesium, potassium, sodium, or zinc salts. Examples of organic base addition salts include amine salts, for example, salts of trimethylamine, diethylamine, ethanolamine, diethanolamine, and ethylenediamine. Quaternary salts of basic nitrogen-containing groups in the compounds may be may be prepared by, for example, reacting the compounds with alkyl halides such as methyl, ethyl, propyl, and butyl chlorides, bromides, and iodides, dialkyl sulfates such as dimethyl, diethyl, dibutyl, and diamyl sulfates, and the like.

N-Oxides of the compounds of the invention are also within the scope of the present invention.

The compounds of the invention may form or exist as solvates with various solvents. If the solvent is water, the solvate may be referred to as a hydrate, for example, a mono-hydrate, a di-hydrate, or a tri-hydrate. All solvated forms and unsolvated forms of the compounds are within the scope of the invention.

The terms "administering" or "administration" refer to placement of the composition or compound of the invention into a subject by a method appropriate to result in an immune response. The dosage form is selected and used as appropriate depending on the therapeutic purpose and the subject. The dose of the composition of the invention may be selected depending on the therapeutic purpose and the characteristics of the subject including their species, age, sex, general health and disease progression. In general, for human subjects, the compound of the invention may be administered in a dose of 0.01 to 100 mg, preferably 0.1 to 50 mg per day, per kg of body weight, either once or divided over several administrations.

A "therapeutically effective amount" (or "effective amount") is an amount sufficient to effect beneficial or desired results, including clinical results, but not limited thereto. A therapeutically effective amount can be administered in one or more administrations by various routes of administration. The therapeutically effective amount of the compound to be administered to a subject depends on, for example, the purpose for which the compound is administered, mode of administration, nature and dosage of any co-administered compounds, and characteristics of the subject, such as general health, other diseases, age, sex, genotype, body weight and tolerance to drugs. A person skilled in the art will be able to determine appropriate dosages having regard to these any other relevant factors.

A "subject" refers to a human or a non-human animal, preferably a vertebrate that is a mammal. Non-human mammals include, but are not limited to; livestock, such as, cattle, sheep, swine, deer, and goats; sport and companion animals, such as, dogs, cats, and horses; and research animals, such as, mice, rats, rabbits, and guinea pigs. Preferably, the subject is a human.

The term "cancer" includes breast, testicular, pancreatic, lung, ovarian, stomach, gallbladder, kidney, skin, prostate, eosophageal, liver, oral, colonic, rectal, uterine, bladder, thyroid and bile duct cancer. It also includes islet cell adenoma, adrenal cortical carcinoma, malignant carcinoid tumour, glioma, osteosarcoma, myeloma, soft tissue sarcoma, neuroblastoma, malignant lymphoma and leukaemia.

For the purposes of the invention, any reference to the disclosed compounds includes all possible formulations, configurations, and conformations, for example, in free form (e.g. as a free acid or base), in the form of salts or hydrates, in the form of isomers (e.g. cis/trans isomers), stereoisomers such as enantiomers, diastereomers and epimers, in the form of mixtures of enantiomers or diastereomers, in the form of racemates or racemic mixtures, or in the form of individual enantiomers or diastereomers. Specific forms of the compounds are described in detail herein.

As used in this specification, the words "comprises", "comprising", and similar words, are not to be interpreted in an exclusive or exhaustive sense. In other words, they are intended to mean "including, but not limited to".

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner In this specification where reference has been made to patent specifications, other external documents, or other sources of information, this is generally for the purpose of providing a context for discussing the features of the invention. Unless specifically stated otherwise, reference to such external documents is not to be construed as an admission that such documents; or such sources of information, in any jurisdiction, are prior art, or form part of the common general knowledge in the art.

5.2 Synthesis of the Compounds of the Invention

The compounds of the invention can be prepared in accordance with the process set out in Example 1, with reference to known methods of chemical synthesis, as explained in, for example, "Compendium of Organic Synthetic Methods", Vol. 1-13, Eds. I. Harrison/L. S. Hegedus/ L. G. Wade/M. B. Smith, 1971-2014, John Wiley & Sons, New York, and "Organic Synthesis: Concepts and Methods", $3^{rd}$ ed., J.-H. Fuhrhop, L. Guangtao, 2003, John Wiley &. Sons, New York.

Methods for protecting reactive species can be found in, for example, Greene's Protective Groups in Organic Synthesis. Fourth Edition. By Peter G. M. Wuts and Theodora W. Greene. John Wiley &. Sons, Inc., Floboken, N J. 2006. Other methods are described in Goodman, M. Methods of Org. Chem. (Flouben-Weyl) add. and suppl. vol. to the 4th ed., Vol. E 22 a, 2002, pp. 425-888; Advanced Organic Chemistry, Part B: Reaction and Synthesis. Fifth Edition. By Francis A. Carey and Richard J. Sundberg, Springer US. 2007. Peptide coupling techniques are described in A. El-Faham and F. Albericio. Peptide coupling reagents: more than a letter soup. Chem. Rev. 111, 6557-6602 (2011) and M. Tsakos, E. S. Schaffert, L. L. Clement, N. L. Villadsen, T. B. Poulsen. Ester coupling reactions—an enduring challenge in the chemical synthesis of bioactive natural products. Nat. Prod. Rep. 32 (4), 605-632 (2015). Esterification reactions are outlined in J. Otera. Transesterification Chem. Rev. 93 (4), 1449-1470 (1993) and V. R. Pattabiraman, J. W. Bode. Rethinking amide bond synthesis. Nature 480, 471-479 (2011).

One exemplary method of preparing the symmetrical compounds of the invention is shown in Scheme 1 below. A detailed description of the methods is found in the Experimental section below.

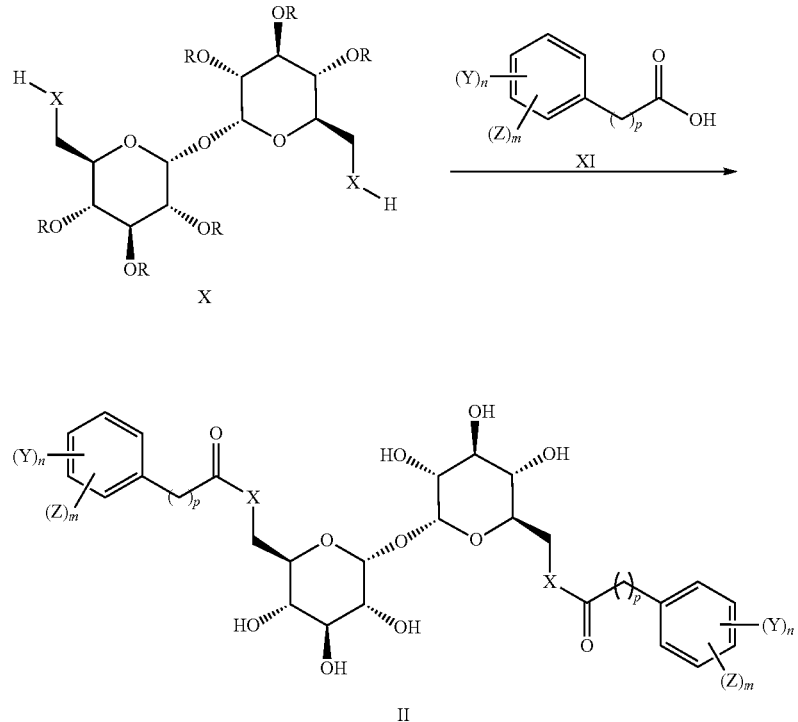

Scheme 1

For the synthesis of compounds of formula II, a compound of formula X (X=O or X=NH), either protected (for example R=Bn, TMS, Lev) or unprotected (R=H) is condensed with a compound of formula XI (with Y, Z, n, m and p as defined previously for Formula II) under the agency of a coupling reagent (for example DCC, BOP, HATU, COMU, $Ph_3P$/DEAD, or any of their derivatives) or using an activated form of carboxylic acid XI (for example an anhydride or acid chloride), followed by optional deprotection (for example using hydrogenation, acid or base) to form the compositions of the invention II.

Alternatively, compounds of formula X (X=NFH) can be formed in situ via the reduction of the corresponding azides using a reducing agent (for example hydrogen, hydride, sulfide or phosphine). Also, compounds of formula X can be subjected to an enzyme, acid, or base catalysed reaction with ester derivatives of XI (such as a Me, Et, or vinyl ester), followed by optional deprotection (for example using hydrogenation, acid or base) to form compositions of the invention II.

Synthesis of unsymmetric compounds of the invention (compounds of formula I) can be carried out in two steps, as shown in Scheme 2 below which illustrates synthesis of compounds of formula Ib.

Scheme 2

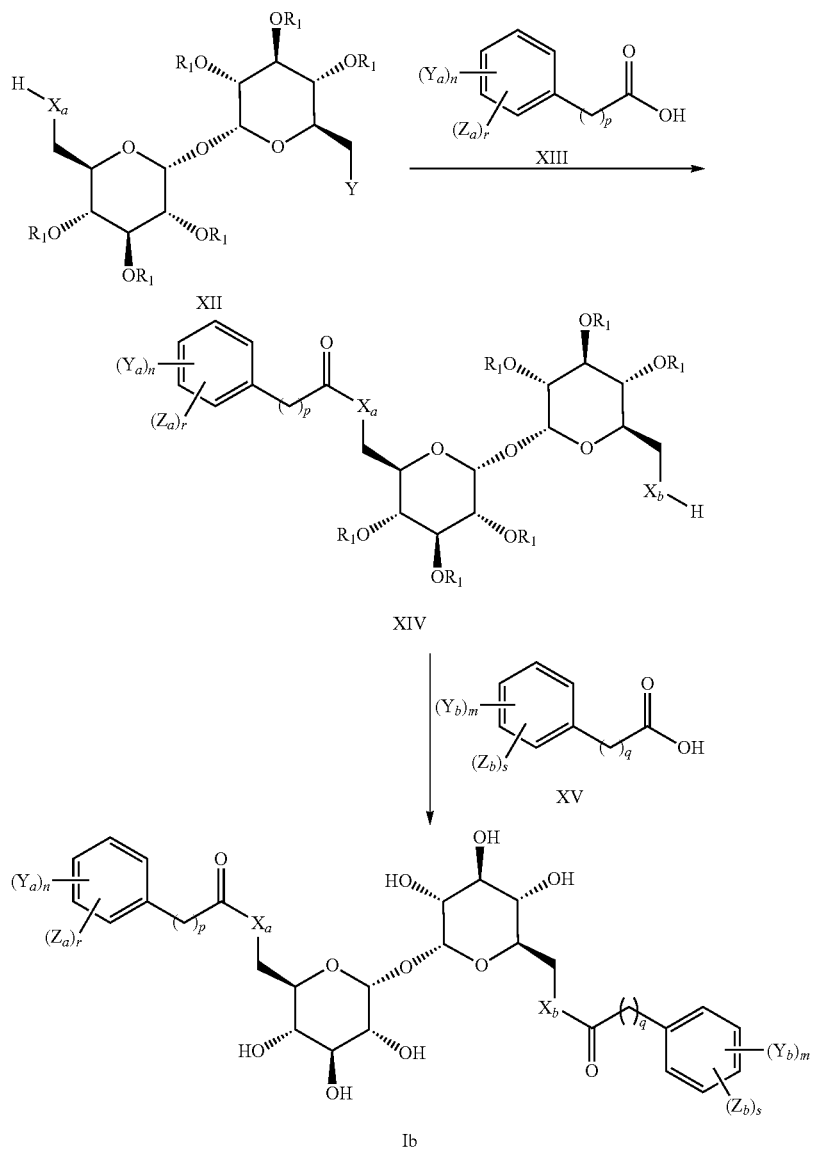

In the synthesis of compounds of formula Ib, a compound of formula XII ($X_a$=O or $X_a$=NH; Y=$OR_2$, where $R_2$=H or protecting group, or Y=$NR_2R_3$, where $R_2$, $R_3$=H or protecting group), either protected (for example $R_1$=Bn, TMS, Lev) or unprotected ($R_1$=H) is condensed with a compound of formula XIII (with $Y_a$, $Z_a$, n, r and p as defined as for Formula I) under the agency of a coupling reagent (for example DCC, BOP, HATU, COMU, $Ph_3P$/DEAD, or any of their derivatives) or using an activated form of carboxylic acid XIII (for example an anhydride or acid chloride), followed by optional deprotection (for example using hydrogenation, acid or base) to form compounds of formula XIV ($X_b$=O or $X_b$=NH). Subsequent condensation of the compounds of formula XIV with a compound of formula XV (with $Y_b$, $Z_b$, m, s and q as defined for Formula I) under the agency of a coupling reagent (for example DCC, BOP, HATU, COMU, $Ph_3P$/DEAD, or any of their derivatives) or using an activated form of carboxylic acid XV (for example an anhydride or acid chloride), followed by optional deprotection (for example using hydrogenation, acid or base) gives the compositions of the invention Ib.

Alternatively, compounds of formula XII ($X_a$=NH) or compounds of formula XIV ($X_b$=NH) can be formed in situ via the reduction of the corresponding azides using a reducing agent (for example hydrogen, hydride, sulfide or phosphine). Also, compounds of formula XII or compounds of formula XIV can be subjected to an enzyme, acid, or base catalysed reaction with ester derivatives of XIII or XV (such as a Me, Et, or vinyl ester), followed by optional deprotection (for example using hydrogenation, acid or base) to form compositions of the invention Ib.

Another exemplary method of preparing the compounds of the invention is set out below. This method was used to prepare the compounds of Example 7. Trehalose was selectively iodinated at the C6 and C6' positions to give 6,6'-dideoxy-6,6'-diiodo-α,α'-trehalose in good (75%) yields (Scheme 3). The iodo-groups were then substituted for azides to give 6,6'-diazido-6,6'-dideoxy-α,α'-trehalose. The di-azide was then subjected to Staudinger reduction conditions to form the intermediate 6,6'-diamino-6,6'-dideoxy-α,α'-trehalose, which was immediately subjected to a coupling reaction with the appropriate benzoic acid, with any phenols protected with benzyl groups, to form the di-amides in good to excellent (57%-93%) yields. Where appropriate, the benzyl protecting groups of the lipid were removed by subjecting the di-amides to palladium catalysed hydrogenation reactions. This provided amides 43i, 43j and 43k.

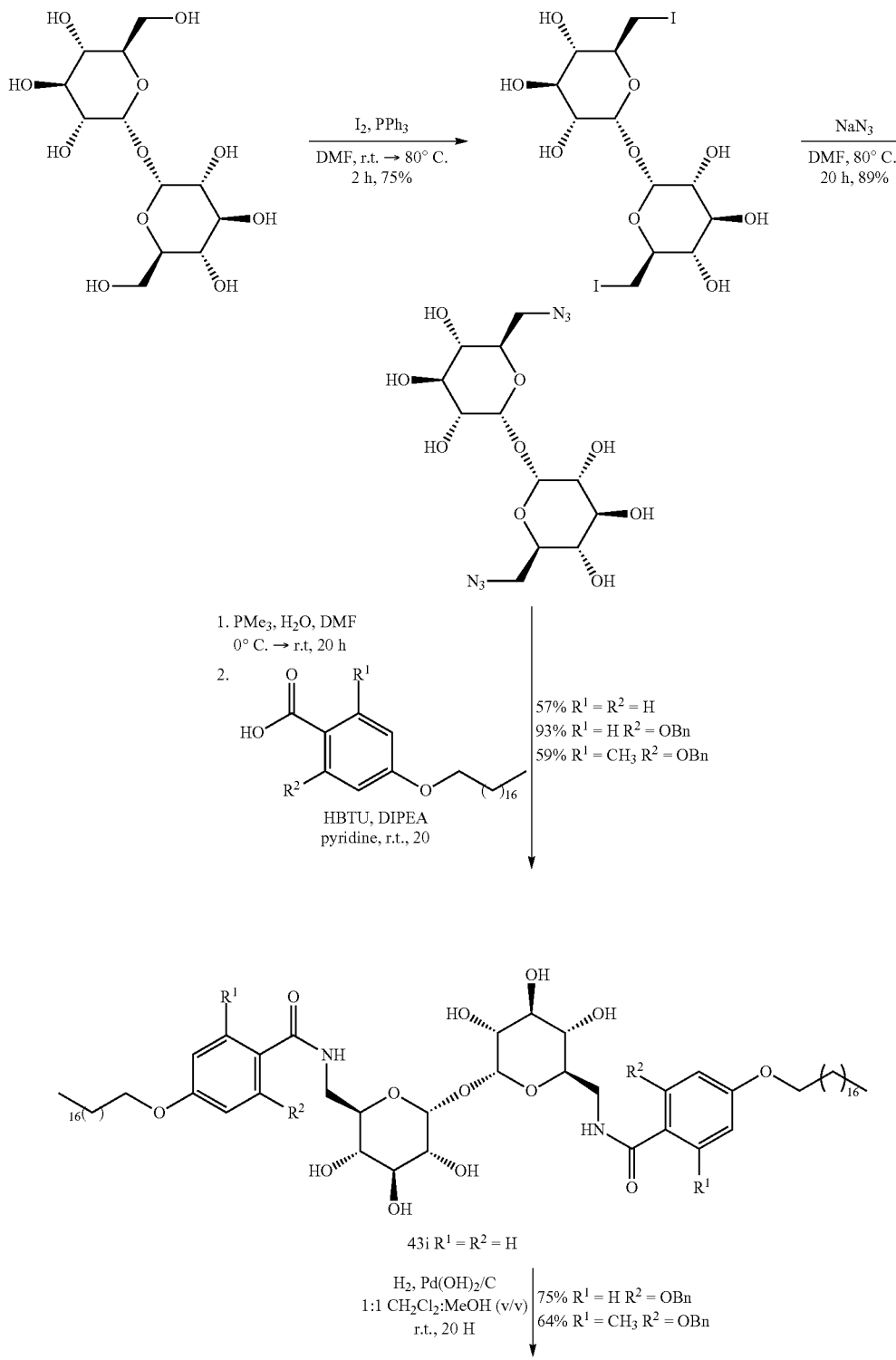

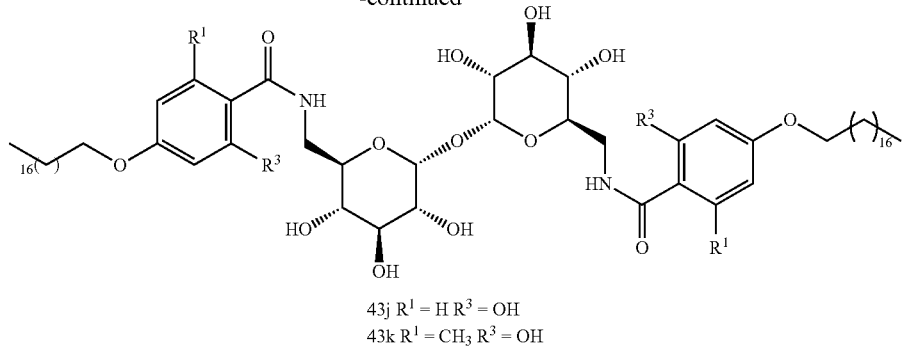

43j R¹ = H R³ = OH
43k R¹ = CH₃ R³ = OH

Methyl 2-hydroxybenzoate (44) and ethyl 3-hydroxybenzoate (45) were first alkylated with 1-bromooctadecane to give the corresponding lipophilic esters 46 and 47 in 29 and 87% yield, respectively (Scheme 4). Next, NaOH mediated hydrolysis of lipophilic esters 46 and 47 gave the o-substituted (48) and m-substituted (49) acids in excellent yield (82 and 88%, respectively). With the appropriate acids in hand, these were then subjected to an EDCI-promoted esterification with benzyl protected trehalose 31. The coupling reaction proceeded uneventfully to yield the corresponding protected glycolipids 50 and 51 in excellent yield (82 and 88%, respectively). Finally, removal of the benzyl protecting groups using Pearlman's catalyst and $H_2$ furnished the target brartemicin analogues o-$OC_{18}$ (43a) and m-$OC_{18}$ (43b).

Scheme 4

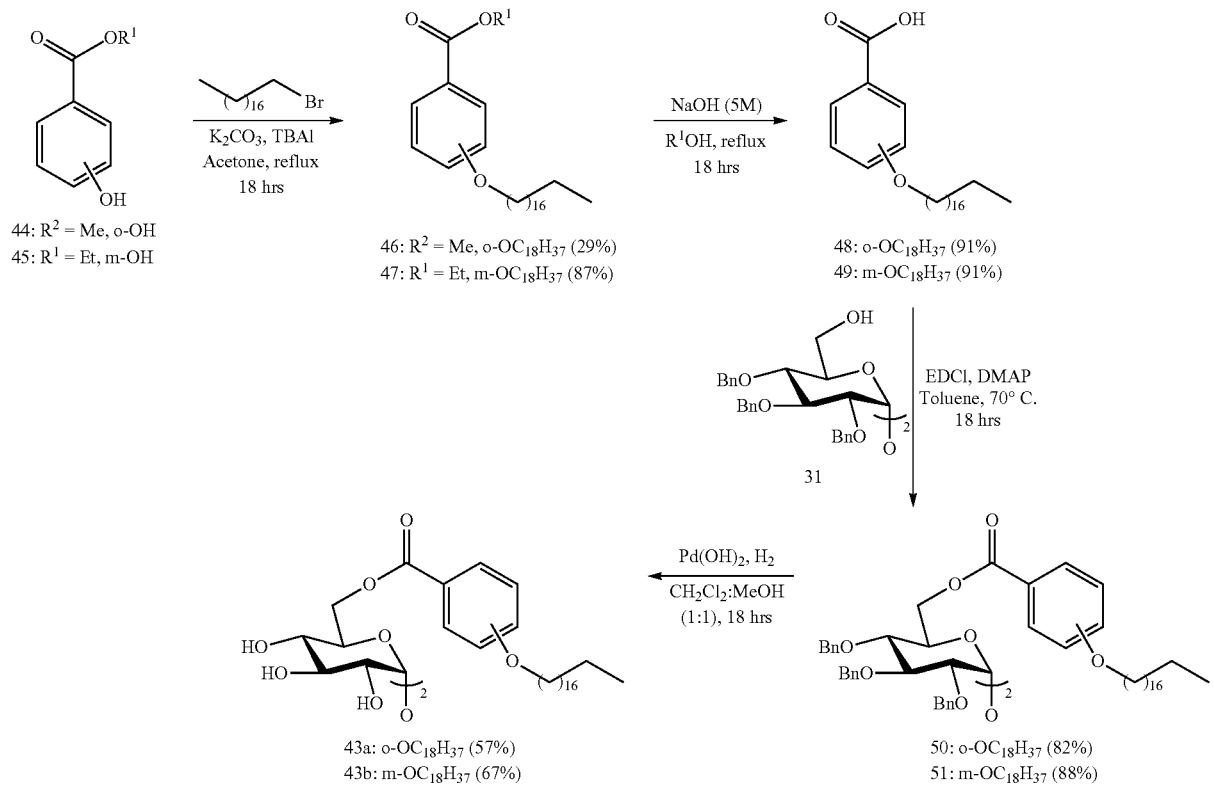

Methyl 3,5-dihydroxybenzoate 52 was di-alkylated with 1-bromooctadecane to install the lipophilic ethers in moderate (63%) yield (Scheme 5). Hydrolysis of methyl ester 53 then afforded the corresponding acid 54, which was then subsequently subjected to an EDCI-mediated esterification with benzyl protected trehalose 31 to yield protected glycolipid 55.

Scheme 5

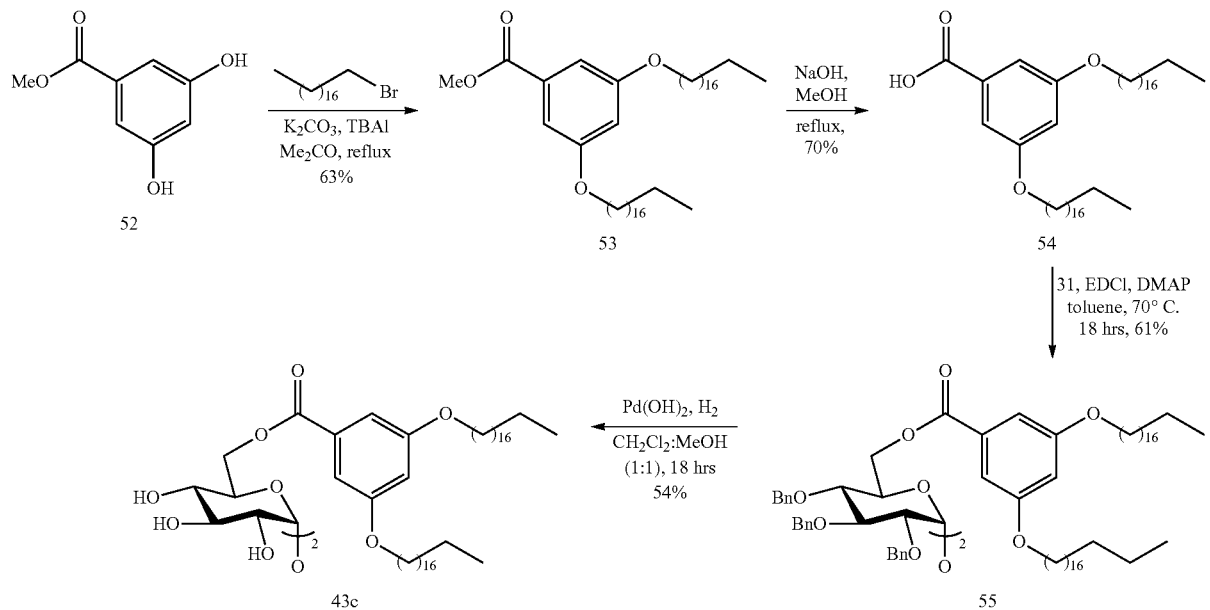

The synthesis of dihydrocinnamate derivative 43d commenced with the alkylation of methyl benzoate 56 with 1-bromohexadecane to install the $C_{16}$ lipid in good (68%) yield (Scheme 6). Hydrolysis of the methyl ester 57 then gave the corresponding acid 58, which was used to esterify benzyl protected trehalose 31 to afford glycolipid 59 in moderate (43%) yield. Finally, the benzyl protecting groups on diester 59 were removed under the agency of Pearlman's catalyst and $H_2$ to give the target glycolipid 43d in 64% yield.

Scheme 6

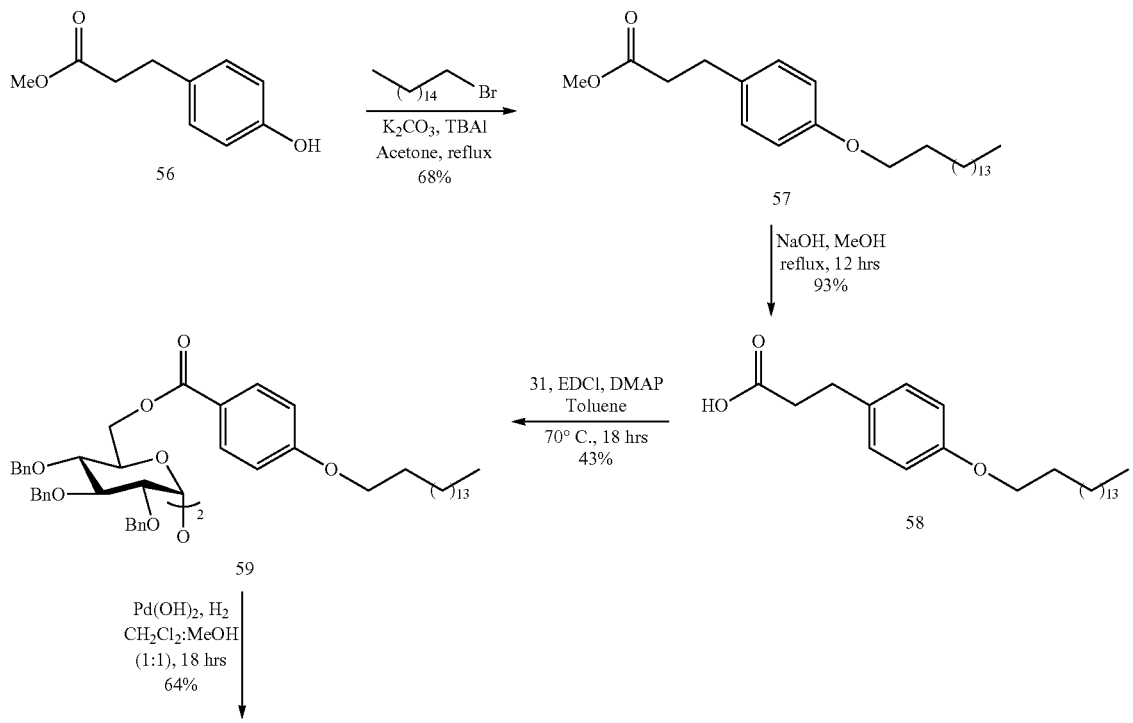

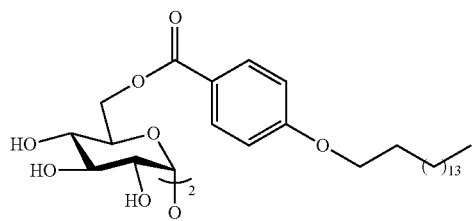

43d

Methyl 4-hydroxycinnamate 61 was treated with 1-bromohexadecane and $K_2CO_3$ to give the lipophilic ester 62 in excellent (88%) yield (Scheme 7). Hydrolysis of methyl ester 62 then gave the corresponding acid 63, which was subsequently used to esterify TMS-protected trehalose 60 to give the α,β-unsaturated diester 64 in moderate yield (32% over two steps). Finally, removal of the TMS protecting groups was achieved using Dowex-H$^+$ to give the target glycolipid 43e in 40% yield.

treatment of phosphonium bromide 66 with BuLi afforded the corresponding ylide, which was immediately subjected to a Wittig reaction with methyl 4-formylbenzoate 67 to yield methyl esters 68 as a 3:1 mixture of the Z- and E-alkenes. These isomers were then immediately hydrolysed under basic conditions to give acids 69 in excellent (91%) yield. Next, EDCI-mediated esterification of benzyl protected trehalose 31 with acids 69 then gave the protected

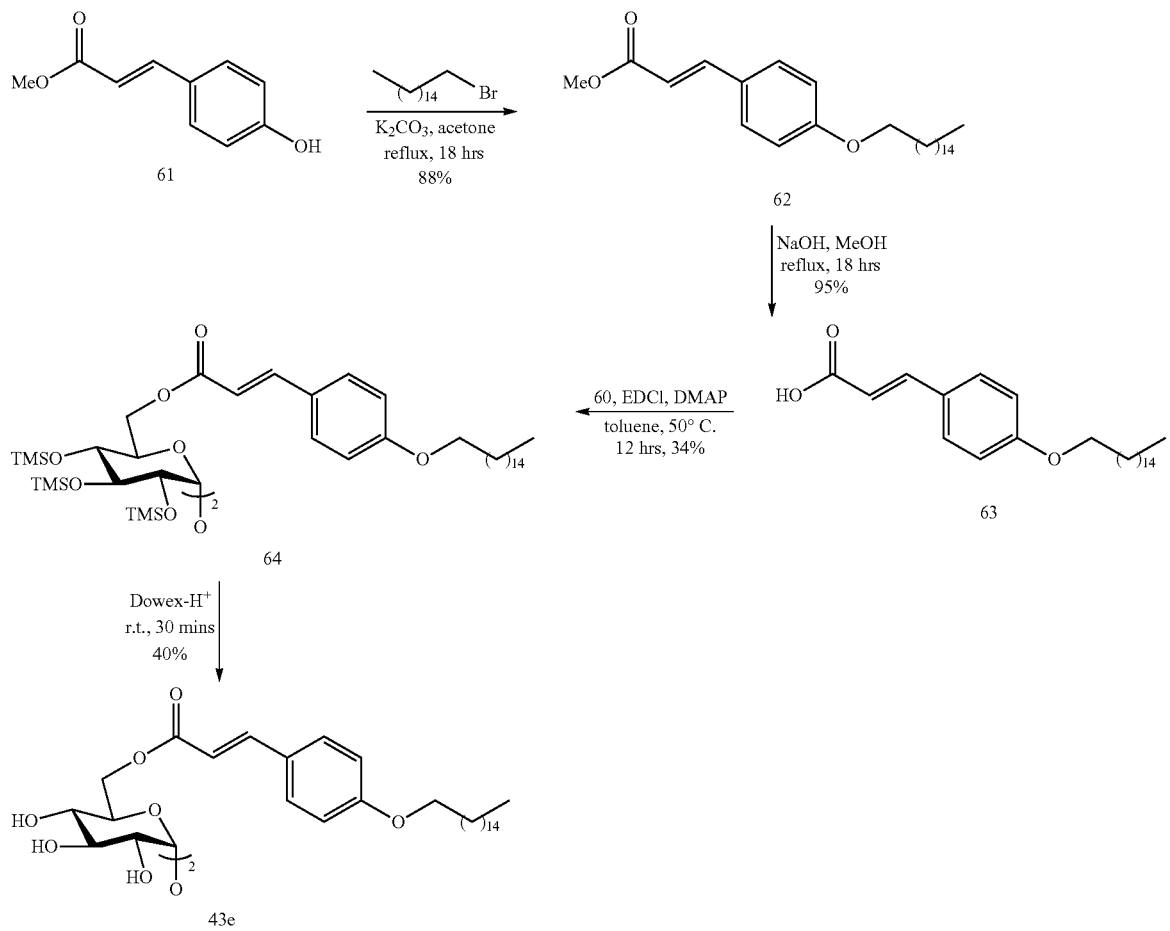

Scheme 7

To synthesise the carbon-linked derivative 43f, 1-bromooctadecane 65 was first reacted with PPh$_3$ to give phosphonium bromide 66 in 57% yield (Scheme 8). Next, glycolipids 70, which was subsequently subjected to Pd(OH)$_2$ and H$_2$ to afford the target carbon-linked glycolipid 43f in 56% yield.

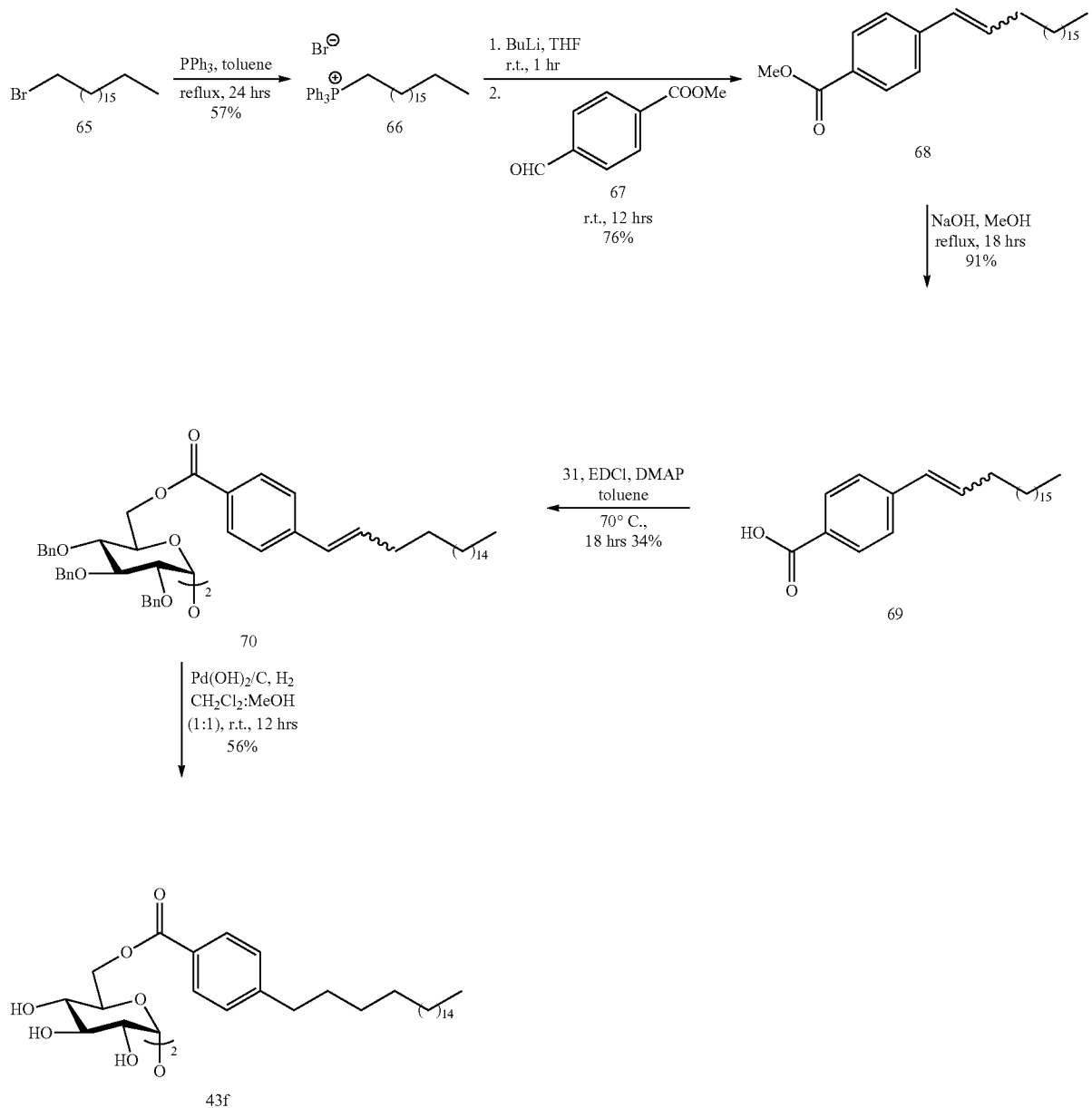

Scheme 8

The synthesis of nitrogen-linked brartemicin derivative 43g commenced with the PCC-mediated oxidation of octadecan-1-ol 71 to give octadecanal (72) in excellent (85%) yield (Scheme 9). Next, reductive amination of octadecanal 72 with ethyl 4-aminobenzoate 73 and sodium triacetoxyborohydride gave secondary amine 74 in moderate (58%) yield. Ethyl ester 74 was then hydrolysed in the presence of NaOH and EtOH to give acid 75 in 99% yield. EDCl-mediated esterification of benzyl protected trehalose 31 with acid 75 then gave the protected nitrogen-linked glycolipid 76 in 38% yield. The modest yield obtained for the esterification reaction was attributed to a loss of material during the purification procedure, whereby size-exclusion chromatography (lipophilic sephadex) was required in order to obtain glycolipid 76 in sufficient purity. With the protected glycolipid 76 in hand, the benzyl protecting groups were removed using Pearlman's catalyst and $H_2$ to give the target nitrogen-linked derivative 43g.

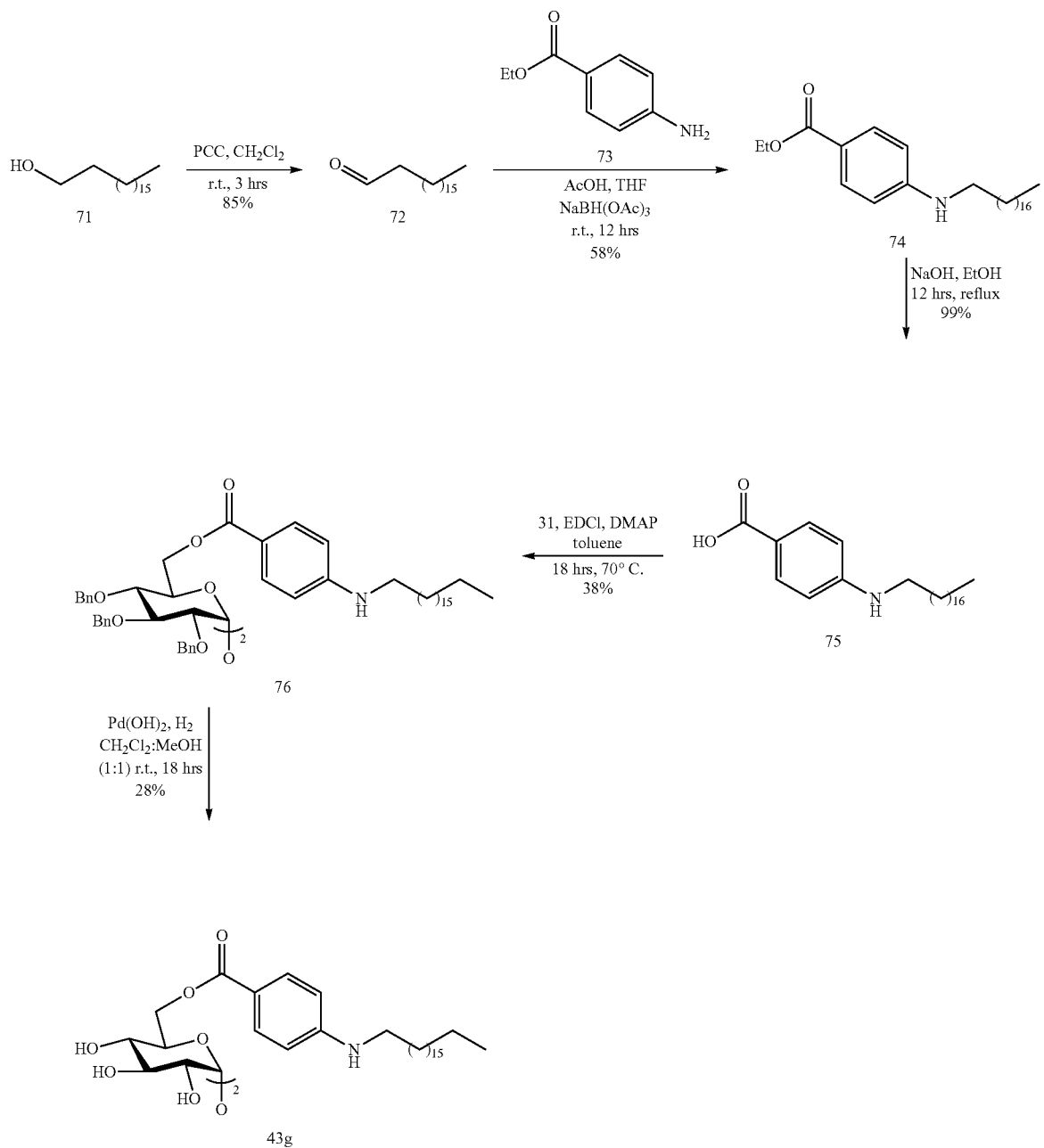

Scheme 9

To synthesise sulfur-linked brartemicin derivative 43h, methyl 4-mercaptobenzoate 77 was alkylated with 1-bromooctadecane to give the corresponding sulphur-linked ester 78 in 39% yield (Scheme 10). Hydrolysis of methyl ester 78 with NaOH then smoothly led to the formation of acid 79, as observed by TLC analysis ($R_f$=0.45 [4:1, pet. ether:EtOAc, v/v]). Acid 79 had relatively low solubility in organic solvents such as EtOAc and $CH_2Cl_2$, which necessitated the use of hot EtOAc to extract the product during work-up. In this way, acid 79 was isolated in an excellent (quant.) yield. Next, TMS protected trehalose 60 was selected as the protected trehalose derivative from which to prepare the sulphur-linked brartemicin derivative 43h. As sulphur-containing compounds can poison Pd-based catalysts,[143] the benzyl protected α,α'-d-trehalose core 31 was avoided in the synthesis of 43h, and thus TMS-protected trehalose 60 was selected for esterification with acid 79 to afford the protected glycolipid 80 in 77% yield. The TMS protecting groups were then removed using Dowex-$H^+$ to give the target sulphur-linked brartemicin derivative 43h in 48% yield Scheme 10

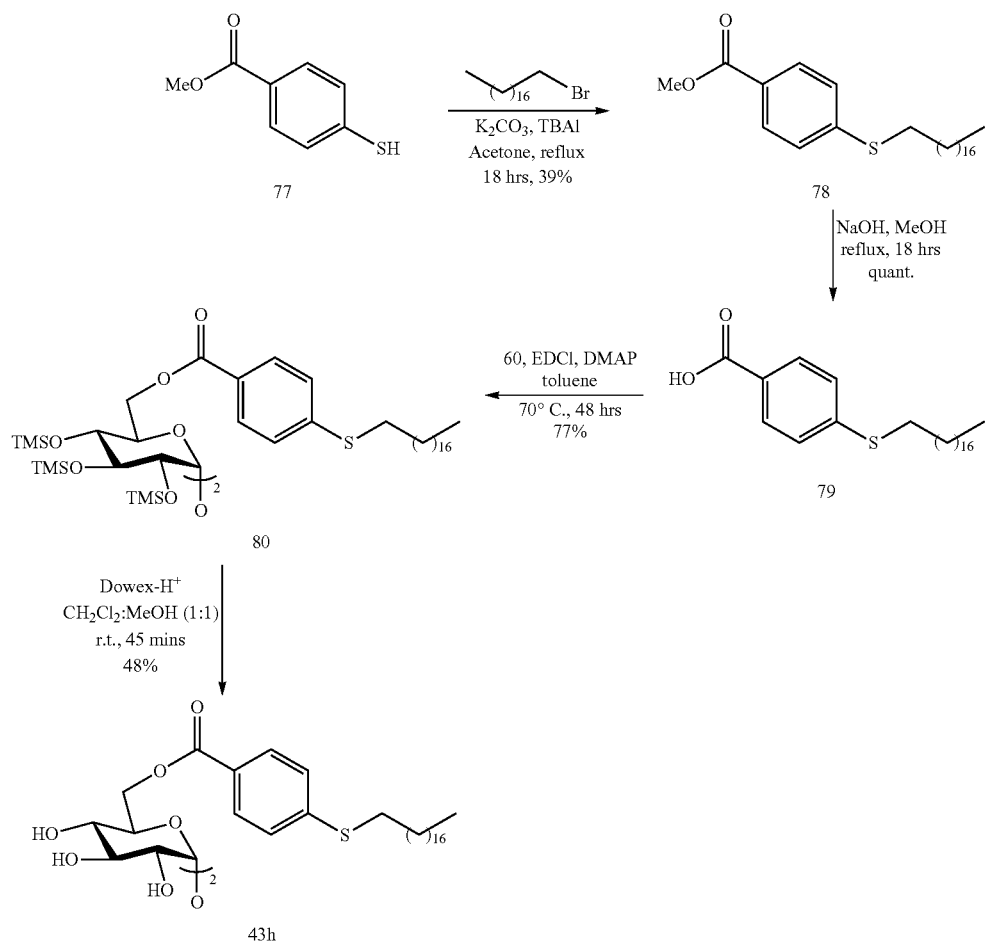

5.3 Uses of the Compounds of the Invention

The compounds of the invention have been shown to bind and activate Mincle PRRs both in vitro and in vivo. The compounds of the invention are derivatives of brartemicin, a natural product isolated from Nonomuraea sp that comprises a doubly esterifiled α,α-trehalose core structure similar to TDM. Brartemicin itself was found not to activate mMincle or hMincle NFAT-GFP reporter cells or BMDMs.

However, the compounds of the invention activate both mMincle and hMincle, with high levels of TNF, IL-6, IL-1β and MIP-2 being produced by the BMDMs upon stimulation by the compounds. When compound 9a was combined with an antigen in vivo, a strong Th1 recall response was observed, greater than that of TDB.

Accordingly, the compounds and compositions of the invention act as immunomodulators that can be used to prevent or treat infections caused by pathogens, as well as cancer and other diseases. The compounds and compositions of the invention, when used in conjunction with antigens, can also function as immunologic adjuvants.

In one aspect, the invention provides a pharmaceutical composition comprising a compound of any of Formula I, Formula Ia, Formula Ib, Formula II or Formula III and one or more pharmaceutical acceptable excipients.

In one embodiment the pharmaceutical composition is a veterinary composition formulated for administration to non-human subjects.

In one embodiment, the pharmaceutical composition additionally comprises an antigen.

In one embodiment, the pharmaceutical composition additionally comprises a Toll-like receptor agonist (TLRA).

In one aspect the invention provides a method of enhancing an immune response in a subject, the method comprising administering to the subject a therapeutically effective amount of a compound of Formula I, Formula Ia, Formula Ib, Formula II or Formula III.

In one aspect the invention provides a method of enhancing an immune response in a subject, the method comprising administering to the subject a therapeutically effective amount of a compound of Formula IV, Formula IVa, Formula IVb, Formula V or Formula VI.

In one aspect the invention provides a method of enhancing an immune response to an antigen in a subject, the method comprising administering to the subject a therapeutically effective amount of a compound of Formula I, Formula Ia, Formula Ib, Formula II or Formula III, in conjunction with the antigen.

In one aspect the invention provides a method of enhancing an immune response to an antigen in a subject, the method comprising administering to the subject a therapeutically effective amount of a compound of Formula IV, Formula IVa, Formula IVb, Formula V or Formula VI.

In one aspect, the invention provides a method of inducing or enhancing Th1-mediated immunity in a subject, the method comprising providing administering to the subject a therapeutically effective amount of a compound of Formula I, Formula Ia, Formula Ib, Formula II or Formula III.

In one aspect, the invention provides a method of inducing or enhancing Th1-mediated immunity in a subject, the method comprising providing administering to the subject a therapeutically effective amount of a compound of Formula IV, Formula IVa, Formula IVb, Formula V or Formula VI.

In one aspect, the invention provides a method of inducing or enhancing Th1-medicated immunity in a subject to an antigen, the method providing administering to the subject a therapeutically effective amount of a compound of Formula I, Formula Ia, Formula Ib, Formula II or Formula III, simultaneously, sequentially or separately with the antigen.

In one aspect, the invention provides a method of inducing or enhancing Th1-medicated immunity in a subject to an antigen, the method providing administering to the subject a therapeutically effective amount of a compound of Formula IV, Formula IVa, Formula IVb, Formula V or Formula VI, simultaneously, sequentially or separately with the antigen.

In one aspect, the invention provides a method of preventing or treating a disease or condition in a subject caused by a pathogen, the method comprising administering to the subject a therapeutically effective amount of a compound of Formula I, Formula Ia, Formula Ib, Formula II or Formula III.

In one aspect, the invention provides a method of preventing or treating a disease or condition in a subject caused by a pathogen, the method comprising administering to the subject a therapeutically effective amount of a compound of Formula IV, Formula IVa, Formula IVb, Formula V or Formula VI.

In the above methods, in one embodiment the subject is a mammal selected from human and non-human mammals. In one embodiment, the subject is a non-human mammal, preferably a companion animal or livestock animal.

In one embodiment the pathogen is selected from the group consisting of human immunodeficiency virus (HIV), tuberculosis, hepatitis A virus, hepatitis B virus, hepatitis C virus, herpes simplex virus (HSV), influenza, pneumonia, meningitis, rotavirus, tetanus, Leishmaniasis, anthrax, human papillomavirus (HPV), measles, rubella, chicken pox, mumps, shingles, polio, pertussis, yellow fever, rabies, tetanus, dengue, typhoid and Japanese encephalitis.

In one embodiment, the pathogen is selected from the group consisting of HIV, tuberculosis, pneumonia, pertussis and meningitis.

In one embodiment the pathogen is selected from the group consisting of viruses, bacteria, protists, and fungi.

In one embodiment the bacteria is selected from the group consisting of *Bacillus, Bartonella, Bordetella, Borrelia, Brucella, Campylobacter, Chlamydia, Chlamydophila, Clostridium, Corynebacterium, Cyptosporidium, Enterococcus, Escherichia, Francisella, Giardia, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio*, and *Yersinia*.

In one embodiment the bacteria is selected from the group consisting of *Bacillus anthracis, Bacillus cereus, Bacillus subtilis, Bacillus thuringiensis, Bartonella henselae, Bartonella quintana, Bordetella pertussis, Borrelia afzelii, Borrelia burgdorferi, Borrelia garinii, Borrelia recurrentis, Brucella abortus, Brucella canis, Brucella melitensis, Brucella suis, Campylobacter coli, Campylobacter fetus, Campylobacter jejuni, Chlamydia pneumoniae, Chlamydia trachomatis, Chlamydophila psittaci, Clostridium botulinum, Clostridium chauvoei, Clostridium difficile, Clostridium haemolyticum, Clostridium perfringens, Clostridium septicum, Clostridium spiroforme, Clostridium tetani, Corynebacterium diphtheriae, Cyptosporidium parvum, Enterococcus avium, Enterococcus casseliflavus, Enterococcus faecalis, Enterococcccus faecium, Enterococcus gallinarum, Enterococcus mundtii, Escherichia coli, Francisella tularensis, Giardia lamblia, Giardia duodenalis, Haemophilus influenzae, Helicobacter pylon, Legionella pneumophila, Leptospira interrogans, Leptospira noguchii, Leptospira santarosai, Leptospira weilii, Listeria monocytogenes, Mycobacterium avium, Mycobacterium bovis, Mycobacterium leprae, Mycobacterium tuberculosis, Mycobacterium uicerans, Mycobacterium paratuberculosis, Mycoplasma pneumoniae, Neisseria gonorrhoeae, Neisseria meningitidis, Pseudomonas aeruginosa, Rickettsia rickettsii, Salmonella dublin, Salmonella* Newport, *Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia enterocolitica, Yersinia pestis*, and *Yersinia pseudotuberculosis*.

In one embodiment the pathogen is selected from the group consisting of *Aphanomyces invadans, Babesia bovis, Babesia bigemina, Anaplasma marginale, Burkhoideria pseudomallei, Calciviridae, Campylobacter hepaticus, Chlamydophila abortus, Coxiella burnetii, Echinococcus, Flaviviridae, Lawsonia intracellularis, Neobenedenia, Paramyxovihdae, Pasteurella multocida, Picornaviridae, Rhabdoviridae, Sparganum mansoni, Streptococcus agalactiae, Streptococcus canis, Streptococcus equi, Streptococcus pneumoniae, Streptococcus suis, Streptococcus uberis, Streptococcus zooepidemicus, Toxocara canis, Toxocara cati, Toxoplasma gondii*, and *Cryptococcus neoformans*.

In one aspect, the invention provides a method of preventing or treating cancer in a subject the method comprising administering to the subject a therapeutically effective amount of a compound Formula I, Formula Ia, Formula Ib, Formula II or Formula III.

In the above aspects:

In one embodiment, the antigen the antigen is selected from the group consisting of a live attenuated microorganism or antigenic parts thereof, an inactivated or dead microorganism or antigenic parts thereof, an inactivated toxin produced by or derived from, viral or bacterial proteins or antigenic fragments thereof, viral or bacterial DNA or antigenic parts thereof, toxoids, and combinations thereof.

In one embodiment, the antigen is selected from the group consisting of an antigen against human immunodeficiency virus (HIV), tuberculosis, hepatitis A virus, hepatitis B virus, hepatitis C virus, herpes simplex virus (HSV), influenza, pneumonia, meningitis, rotavirus, tetanus, Leishmaniasis, anthrax, human papillomavirus (HPV), measles, rubella, chicken pox, mumps, shingles, polio, pertussis, yellow fever, rabies, tetanus, dengue, typhoid and Japanese encephalitis.

In one embodiment, the subject is immune compromised. In one embodiment the immune compromised subject is selected from the group consisting of newborns, infants, children under 12 years of age, the elderly, HIV sufferers and people taking immunosuppresants.

In one embodiment, administration is local or systemic administration. In one embodiment, administration is intranasal, epidermal, and transdermal, oral or parenteral.

In one embodiment oral administration comprises application of a liquid, gel, creme, ointment, lotion or slurry. In one embodiment oral administration comprises delivery of an oral dosage form. In one embodiment the oral dosage form is a solid oral dosage form. In one embodiment the solid oral dosage form comprises a powder, a granule, a tablet, a pill, a capsule or a lozenge or combination thereof.

In one embodiment the oral dosage form is a liquid dosage form. In one embodiment the liquid dosage form is aqueous suspension, an aqueous solution, a non-aqueous suspension or a non-aqueous solution.

In one embodiment the oral dosage from comprises an additional ingredient selected from the group consisting of thickeners, flavoring agents, diluents, emulsifiers, dispersing aids and binders.

In one embodiment, parenteral administration is selected from the group consisting of direct application, systemic, subcutaneous, intraperitoneal or intramuscular injection, intravenous drip or infusion, inhalation, insufflation or intrathecal or intraventricular administration.

In one embodiment, administration is transient administration. In one embodiment transient administration comprises administration of a compound of the invention or a pharmaceutical composition as described herein for a sufficient period of time to provide a treatment or achieve a therapeutic result.

A particular and effective dosage regime according to a method of the invention will be dependent on severity of the disease and/or condition to be treated and on the responsiveness of the treated subject to the course of treatment. An effective treatment may last from several hours to several days to several months or longer, or until an acceptable therapeutic outcome is affected or assured or until an acceptable reduction of the infection is observed.

An optimal dosing schedule (s) may be calculated from drug accumulation as measured in the body of a treated subject. It is believed to be within the skill of persons in the art to be able to easily determine optimum and/or suitable dosages, dosage formulations and dosage regimes. Of course, the optimum dosages may vary depending on the relative potency of the compound of the invention or pharmaceutical composition comprising the compound. In general, dosage is from 0.0001 g to 99 g per kg of body weight, and may be given once or more daily, weekly, monthly or yearly, but not limited thereto.

In one aspect the invention provides the use of a compound of Formula I, Formula Ia, Formula Ib, Formula II, Formula III, Formula IV, Formula IVa, Formula IVb, Formula V or Formula VI in the manufacture of a medicament for enhancing an immune response in a subject.

In one aspect the invention provides the use of a compound of Formula I, Formula Ia, Formula Ib, Formula II, Formula III, Formula IV, Formula IVa, Formula IVb, Formula V or Formula VI and an antigen in the manufacture of a medicament for enhancing an immune response to the antigen in a subject.

In one aspect the invention provides the use of a compound of Formula I, Formula Ia, Formula Ib, Formula II, Formula III, Formula IV, Formula IVa, Formula IVb, Formula V or Formula VI in the manufacture of a medicament for inducing or enhancing Th1-mediated immunity in a subject.

In one aspect the invention provides the use of a compound of Formula I, Formula Ia, Formula Ib, Formula II, Formula III, Formula IV, Formula IVa, Formula IVb, Formula V or Formula VI and an antigen in the manufacture of a medicament for inducing or enhancing Th1-mediated immunity in a subject to an antigen, wherein the medicament is formulated for the administration of the compound of Formula I or Formula II simultaneously, sequentially or separately with the antigen.

In one aspect, the invention provides for the use of a compound of Formula I, Formula Ia, Formula Ib, Formula II, Formula III, Formula IV, Formula IVa, Formula IVb, Formula V or Formula VI in the manufacture of a medicament for preventing or treating a disease or condition in a subject caused by a pathogen.

In one aspect the invention provides for a composition comprising a compound of Formula I, Formula Ia, Formula Ib, Formula II, Formula III, Formula IV, Formula IVa, Formula IVb, Formula V or Formula VI for use for enhancing an immune response in a subject.

In one aspect the invention provides a composition comprising a compound of Formula I, Formula Ia, Formula Ib, Formula II, Formula III, Formula IV, Formula IVa, Formula IVb, Formula V or Formula VI and an antigen for use for enhancing an immune response to the antigen in a subject.

In one aspect the invention provides a composition comprising a compound of Formula I, Formula Ia, Formula Ib, Formula II, Formula III, Formula IV, Formula IVa, Formula IVb, Formula V or Formula VI for use for inducing or enhancing Th1-mediated immunity in a subject.

In one aspect the invention provides a composition comprising a compound of Formula I, Formula Ia, Formula Ib, Formula II, Formula III, Formula IV, Formula IVa, Formula IVb, Formula V or Formula VI and an antigen for inducing or enhancing Th1-mediated immunity in a subject to an antigen, wherein the composition is formulated for the administration of the compound of Formula I or Formula II simultaneously, sequentially or separately with the antigen.

In one aspect the invention provides a composition comprising a compound of Formula I, Formula Ia, Formula Ib, Formula II, Formula III, Formula IV, Formula IVa, Formula IVb, Formula V or Formula VI for use for preventing or treating a disease or condition in a subject caused by a pathogen.

In one embodiment the composition comprises a therapeutically effective amount of a compound of Formula I, Formula Ia, Formula Ib, Formula II, Formula III, Formula IV, Formula IVa, Formula IVb, Formula V or Formula VI.

Specifically contemplated as embodiments of the above aspects of the invention related to uses of the compounds of the invention in the manufacture of medicaments, and to compositions for use are all of the embodiments encompassed herein by the method of treatment aspects set out above.

The compounds of the invention described as having been prepared in the Examples are specifically contemplated for use in the methods of treatment, manufacture of medicaments and compositions for use in said methods.

Additionally, the following embodiments of the invention are also contemplated for the aspects of the invention above that are the uses of the compounds of the invention in the manufacture of medicaments, and the compositions for use.

In one embodiment the medicament is formulated for administration, or is in a form for administration, to a subject in need thereof. In one embodiment the medicament is in a form for, or is formulated for topical, intranasal, epidermal, transdermal, oral or parenteral administration. In one embodiment parenteral administration is selected from the group consisting of direct application, systemic, subcutaneous, intraperitoneal or intramuscular injection, intravenous drip or infusion, inhalation, insufflation or intrathecal or intraventricular administration. In one embodiment the medicament is formulated for topical administration, or is in the form of a topical composition, or when administered, is administered topically.

In one embodiment the medicament is in a form for, or is formulated for, parenteral administration in any appropriate solution, preferably in a sterile aqueous solution which may also contain buffers, diluents and other suitable additives.

In one embodiment the medicament formulated for, or is in a form for oral administration selected from the group consisting of a powder, a granule, an aqueous suspension, an aqueous solution, a non-aqueous suspension, a non-aqueous solution, a gel, a slurry, an ointment, a creme, a spray, a capsule, a pill, a lozenge, and a tablet.

When administered orally, the addition of one or more of the following may be desirable: thickeners, flavoring agents, diluents, emulsifiers, dispersing aids or binders.

In one embodiment the medicament is formulated for, or is in a form for topical or direct administration selected from the group consisting of transdermal patches, subdermal implants, ointments, lotions, creams, gels, drops, pastes, suppositories, sprays, liquids and powders. Conventional carriers, particularly pharmaceutical carriers, aqueous, powder or oily bases, thickeners and the like may be used as required or desired in this embodiment.

In one embodiment, the direct administration is direct application or local application. In one embodiment direct or local application comprises application of the medicament in combination with a delivery reagent or additional active agent.

A person skilled in the art will be able to choose the appropriate mode of administration of the medicament with reference to the literature and as described herein. By way of non-limiting example, a topical application would be preferred for the treatment and prevention of atopic dermatitis.

In one embodiment the medicament is for, is formulated for, or is in a form for administration separately, simultaneously or sequentially with an additional active agent.

By way of non-limiting example, one additional active agent that may be included in the composition of, or for use in the invention, is an antibiotic that is, or is suspected of being effective against desired disease or condition.

In one embodiment the medicament is formulated for application to an animal or part thereof. In one embodiment the medicament is in a form for application to an animal or part thereof. In one embodiment the medicament is formulated for administration to an animal. In one embodiment the medicament is in a form for administration to an animal.

In one embodiment the animal is a mammal. In one embodiment the mammal is a non-human mammal. In one embodiment the mammal is a human.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents; or such sources of information, in any jurisdiction, are prior art, or form part of the common general knowledge in the art.

The invention will now be illustrated in a non-limiting way by reference to the following examples.

6. EXAMPLES

General Methods

Chemistry: Unless otherwise stated, all reactions were performed under an atmosphere of argon. Acetone, methyl iodide, 1-iodoheptane and 1-iodobutane were distilled and stored over molecular sieves (4 Å). Methyl 2,4-dihydroxy benzoate (BDH), methyl 4-hydroxybenzoate (BDH), 1-bromooctadecane (Aldrich), TBAI (Riedel-de Haen), benzyl bromide (Aldrich), methanol (Fischer Scientific), sodium hydroxide (Vickers), $K_2CO_3$ (Panreac) ethanol (Fischer Scientific), EDCI (Chem Impex), DMAP (Lab Supply), Toluene (ROMIL), $Pd(OH)_2$ (Aldrich), $CH_2Cl_2$ (Fischer Scientific), pyridine (ROMIL), $C_5D_5N$ (Apollo), $CDCl_3$ (Aldrich), $CD_3OD$ (Cambridge Isotopes Laboratories Inc.), $H_2$ (BOC), EtOAc (Pure Science), and petroleum ether (Pure Science) were used as received. 2,2',3,3',4,4'-Hexa-O-benzyl-α,α'-D-trehalose was prepared according to a literature procedure (Khan et al. 2011).

Methyl 2,4-dihydroxy benzoate (Carta et al 2013) and ethyl 2,4-dihydroxy-6-methylbenzoate (Baird et al. 2009) were prepared according to adapted literature procedures. All solvents were removed by evaporation under reduced pressure. Reactions were monitored by TLC-analysis on Macherey-Nagel silica gel coated plastic sheets (0.20 mm with fluorescent indicator UV254) via detection by UV-absorption (254 nm), dipping in 10% $H_2SO_4$ in EtOH followed by charring, dipping in $KMnO_4$ solution (2% in $H_2O$), or dipping in ceric ammonium molybdate solution. Column chromatography was performed using Pure Science silica gel (40-63 μm), and size exclusion chromatography was performed using lipophilic Sephadex (25-100 μm, Sigma). High resolution mass spectra were recorded on an Agilent 6530 Q-TOF mass spectrometer utilising a Jet-Stream electrospray ionisation source in positive and negative mode. Optical rotation were recorded on a Autopol II or IV (Rudolph Research Analytical) at 589 nm (sodium d-line). Infrared spectra were recorded as thin films using a Bruker Platinum ATR and are reported in wave numbers ($cm^{-1}$). Nuclear magnetic resonance spectra were recorded at 20° C. in $C_5D_5N$, $CD_3OD$, or $CDCl_3$ using a varian INOVA operating at 500 or 600 MHz. Chemical shifts are given in ppm (δ) relative to residual solvent peaks. NMR peak assignments were made using COSY, HSQC, and HMBC 2D experiments. Melting points were obtained using a Gallenkamp Melting Point Apparatus.

Mice: C57BL/6 wild-type, Mincle−/− and OT-II mice were bred and housed in a conventional animal facility at the Malaghan Institute of Medical Research, New Zealand, or Kyushu University, Japan. All mice used for experiments were aged between 8-12 weeks and experimental procedures were approved by the Victoria University Animal Ethics Committee or the committee of Ethics on Animal Experiments, Faculty of Medical Sciences, Kyushu University.

Endotoxin testing: All synthesised glycolipids were confirmed to be endotoxin free at a sensitivity of ≤0.1 EU/mL by using the Pierce Limulus amebocyte lysate (LAL) chromogenic Endotoxin Quantitation kit (Thermo Scientific).

Preparation of ligand-coated plates: Brartemicin analogues 9a-9i, TDM (Carbosynth, Sigma Aldrich), and TDB[14] were dissolved in $CHCl_3$:MeOH (2:1, 1 mM), diluted in isopropanol (0.05 mM) and added to 96-well plates (20 μL/well). The solvents were evaporated and the coated plates were used immediately.

In vitro Mincle binding assay: The preparation of mMincle- and hMincle-Ig fusion proteins have been previously described. Plate-coated glycolipids 9a-i, TDB, and TDM were incubated with hMincle-Ig, mMincle-Ig, or hIgG1-Fc (Ig) [3 µg/mL in binding buffer (20 mM Tris-HCl, 150 mM NaCl, 1 mM $CaCl_2$), 2 mM $MgCl_2$, pH 7.0)]. Detection of bound protein was achieved via incubation with anti-hIgG-HRP followed by the addition of a colorimetric substrate and measurement of OD at 450 nm. Background was accounted for by subtracting the hIgG1-Fc $OD_{450}$ values from fusion protein $OD_{450}$ values 2B4-NFAT-GFP reporter cells: 2B4-NFAT-GFP reporter cells expressing mMincle+FcRγ, hMincle+FcRγ, or FcRγ only have been previously described. NFAT-GFP 2B4 reporter cells were incubated with ligand-coated plates (0.01, 0.1, or 1 nmol/well) for 18 hours. The reporter cells were harvested, stained with propidium iodide, and analysed for NFAT-GFP expression using flow cytometry (FACS Calibur).

Murine bone-marrow derived macrophages: For the preparation of murine bone-marrow derived macrophages, bone marrow cells were collected from the tibias and femurs of C57BL/6 mice and cultured (250,000 cells/mL) in complete RPMI media [RPMI-1640 (Gibco) with 10% heat inactivated fetal bovine serum (Gibco), 100 unit/mL penicillin-streptomycin (Gibco) and 2 mM Glutamax (Gibco)] supplemented with 50 ng/mL GM-CSF (clone X63/GM-CSF murine cells). Cells were incubated at 37° C. (5% $CO_2$) for 8 days (cells fed by replacing half the media on days 3 and 6). On day 8, all media was removed and the cells were washed with Dulbecco's Phosphate-Buffered Saline (DPBS, Gibco) to remove any loosely-adherent cells. The BMDMs were harvested with StemPro Acutase (1 mL/well, 15 minutes at room temperature, Gibco) and seeded onto a pre-coated 96-well plate. The supernatant was collected and analysed for cytokine/chemokine production after 24 hours.

Cytokine analysis: IL-1β, IFN-γ, IL-6, TNF-α (BD Biosciences), IL-17, and MIP-2 (R&D) levels were determined via sandwich ELISA according to the manufacturer's instructions.

Site-directed mutagenesis: Site-directed mutagenesis was performed using a QuikChange™ Site-Directed Mutagenesis Kit, codon-modified primers and the template plasmid, pMX-IRES-hCD8-hMincle. The primer sets used were 5'-GGACTGTGCCACCATGGCAGACTCTTCAAACC-CAA-3' and 5'-TTGGGTTTGAAGAGTCTGC-CATGGTGGCACAGTCC-3' for amino acid mutations at position 183. PCR amplification was performed with Pfu-Turbo DNA polymerase for 18 cycles of 30 s at 95° C., 1 min at 55° C. and 7 min at 68° C. The successful introduction of this mutation was corroborated by DNA sequencing. The mutated genes were transfected into phoenix cells using Polyethylenimine (Polysciences), and then introduced into FcRγ-only expressing NFAT-GFP 2B4 cells using retrovirus-mediated infection.

Antibodies. Mincle expression was analysed by flow cytometry (FACS Calibur) using anti-human Mincle antibody [(13D10-H11), Biotin-labelling kit (DOJINDO)] and SA-PE (BioLegend).

BMDC-OT-II T-cell co-cuture: A mixture of OT-II cells ($1\times10^5$ cells/100 µL) and BMDCs ($1\times10^4$ cells/100 µL) were stimulated with plate coated glycolipd (0.1 nmol/well) or iPrOH only (20 µL/well) and increasing concentrations of OVA (0, 0.1, or 1 µM). After 48 or 72 hours, the supernatant was collected and ELISA was employed to determine the levels of IFN-γ and IL-17.

Delayed-type hypersensitivity: Mice were sensitised by subcutaneous injection with oil-in-water emulsions (mineral oil/Tween-80/PBS, 9:1:90, v/v/v) containing OVA only (200 µg), OVA+TDB (OVA=200 µg, TDB=0.3 µmol), OVA+9a (OVA=200 µg, 9a=0.3 µmol) or no OVA. After seven days, the mice were challenged with OVA (100 µg/footpad) and after a further seven days, the mice were sacrificed and their spleens harvested. For in vitro restimulation, splenocytes were restimulated with OVA and analysed for spenocyte number (measured at 450 nm after 3 hours, Cell Count Reagent SF, Nacalai Tesque Inc.), IFN-γ production, and IL-17 production. Footpad swelling was measured using a venier caliper pre-challenge, 24 hours post-challenge, and 48 hours post-challenge. Sera were collected from each mouse on days 0, 7, and 14 and analysed for OVA-specific antibody titers by ELISA using HRP coupled goat anti-mouse IgG (GE Health-care), IgG1, IgG2b, IgG2c, and IgG3 (SouthernBiotec). $EC_{50}$ were defined by plotting the absorbance at 450 nm against log of serum concentration. Antibody titration curves were plotted using GraphPad Prism7 (GraphPad Software).

Statistics: Two-way ANOVA was used for all statistical analyses (Prism7)

Example 1: Preparation of Compounds of the Invention

Preparation of Starting Materials

General procedure for the synthesis of 4-O-alkyl-benzoates: To a solution of benzoate (1 equiv.) in acetone (20 mL) was added $K_2CO_3$ (1.4-2 equiv.), alkyl halide (1.2-1.5 equiv.) and TBAI (for 4-O-octadecyloxy-benzoates only, 0.05-0.1 equiv.) The mixture was heated at reflux until the reaction was completed (as gauged by TLC analysis, 18-48 hrs). The reaction mixture was cooled to room temperature and concentrated under reduced pressure. The resulting residue was purified using gradient silica-gel flash column chromatography (petroleum ether to petroleum ether: EtOAc; 9:1; v/v).

Methyl 2-hydroxy-4-methoxybenzoate. By subjecting methyl 2,4-dihydroxybenzoate (400 mg, 2.39 mmol), methyl-iodide (0.19 mL, 3.12 mmol), and $K_2CO_3$ (528 mg, 3.82 mmol) to the general procedure for the synthesis of 4-O-alkyl-benzoates, the title compound was obtained as a clear oil (390 mg, 2.14 mmol, 90%).

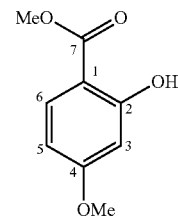 [SMILES: COC(=O)c1ccc(OC)cc1O]

Methyl 4-butoxy-2-hydroxybenzoate. By subjecting methyl 2,4-dihydroxybenzoate (205 mg, 1.22 mmol), 1-iodobutane (0.20 mL, 1.55 mmol), and $K_2CO_3$ (291 mg, 2.11 mmol) to the general procedure for the synthesis of 4-O-alkyl-benzoates, the title compound was obtained as a clear oil (248 mg, 1.10 mmol, 90%).

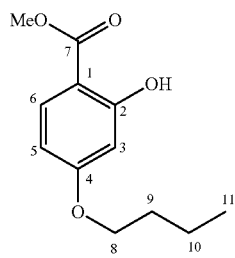

Methyl 4-(heptyloxy)-2-hydroxybenzoate. By subjecting methyl 2,4-dihydroxybenzoate (310 mg, 1.84 mmol), $K_2CO_3$ (395 mg, 2.86 mmol), and 1-iodoheptane (0.38 mL, 2.31 mmol) to the general procedure for the synthesis of 4-O-alkyl-benzoates, the title compound was obtained as a colourless oil (479 mg, 1.80 mmol, 98%).

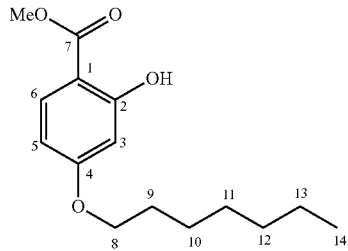 [SMILES: CCCCCCCOc1ccc(C(=O)OC)c(O)c1]

Methyl 2-hydroxy-4-(octadecyloxy)benzoate. By subjecting methyl 2,4-dihydroxybenzoate (357 mg, 2.12 mmol), $K_2CO_3$ (429 mg, 3.10 mmol), 1-bromooctadecane (836 mg, 2.50 mmol), and TBAI (71 mg, 0.19 mmol) to the general procedure for the synthesis of 4-O-alkyl-benzoates, the title compound was obtained as an amorphous off-white solid (695 mg, 1.65 mmol, 78%).

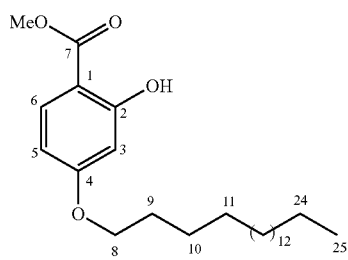

Methyl 4-(heptyloxy)-benzoate By subjecting methyl 4-hydroxybenzoate (550 mg, 3.62 mmol), $K_2CO_3$ (1.01 g, 7.33 mmol), and 1-iodoheptane (0.77 mL, 4.70 mmol) to the general procedure for the synthesis of 4-O-alkyl-benzoates, the title compound was obtained as an amorphous white solid (853 mg, 3.41 mmol, 94%).

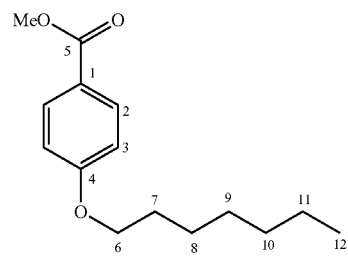 [SMILES: CCCCCCCOc1ccc(C(=O)OC)cc1]

Methyl 4-(octadecyloxy)benzoate. By subjecting methyl 4-hydroxybenzoate (406 mg, 2.67 mmol), $K_2CO_3$ (565, 4.09 mmol), 1-bromooctadecane (1.31 g, 3.92 mmol), and TBAI (101 mg, 0.27 mmol) to the general procedure for the synthesis of 4-O-alkyl benzoates, the title compound was obtained as an amorphous white solid (968 mg, 2.39 mmol, 90%).

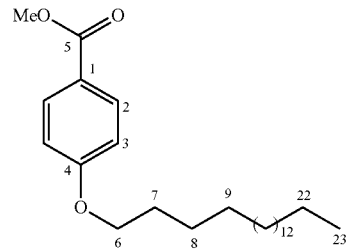

Methyl 2-hydroxy-6-methyl-4-(octadecyloxy)benzoate. By subjecting ethyl 2,4-dihydroxy-6-methylbenzoate (500 mg, 2.55 mmol), $K_2CO_3$ (478 mg, 3.46 mmol), 1-bromooctadecane (1.047, 3.14 mmol), and TBAI (50 mg, 0.14 mmol) to the general procedure for the synthesis of 4-O-alkyl-benzoates, the title compound was obtained as an amorphous pale yellow solid (1.13 g, 2.52 mmol, 99%).

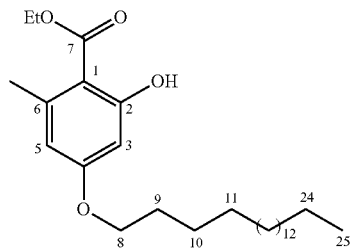

General benzylation procedure: To a solution of benzoate (1 equiv.) in acetone (20 mL) was added $K_2CO_3$ (1.2-3 equiv.), benzyl bromide (1.2-3 equiv.), and TBAI (0.03-0.1 equiv.). The resulting mixture was refluxed for 18 hours, cooled to room temperature, and concentrated in vacuo. The residue was then purified using silica-gel flash column chromatography (petroleum ether to petroleum ether: EtOAc, 4:1, v/v).

Methyl 2,4-bis(benzyloxy)benzoate. By subjecting methyl 2,4-dihydroxybenzoate (178 mg, 1.15 mmol), benzyl bromide (0.41 mL, 3.46 mmol), $K_2CO_3$ (478 mg, 3.46 mmol), and TBAI (43 mg, 0.12 mmol) to the general procedure for benzylation, the title compound was obtained as an amorphous yellow solid (378 mg, 1.08 mmol, 94%).

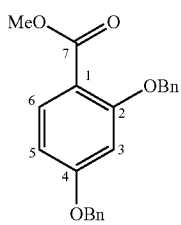

Ethyl 2,4-bis(benzyloxy)-6-methylbenzoate. By subjecting ethyl 2,4-dihydroxy-6-methylbenzoate (300 mg, 1.53 mmol), K$_2$CO$_3$ (517 mg, 3.74 mmol), benzyl bromide (0.47 mL, 3.82 mmol) to the general procedure for benzylation, the title compound was obtained as an amorphous white solid (566 mg, 1.50 mmol, 98%).

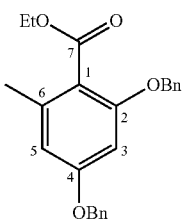

Methyl 2-(benzyloxy)-4-methoxybenzoate. By subjecting methyl 2-hydroxy-4-methoxybenzoate (290 mg, 1.59 mmol), benzyl bromide (0.26 mL, 2.07 mmol), K$_2$CO$_3$ (297 mg, 2.15 mmol), and TBAI (55 mg, 0.15 mmol) to the general procedure for benzylation, the title compound was obtained as a pale yellow oil (422 mg, 1.55 mmol, 97%).

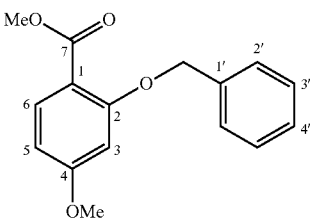 [SMILES: COC(=O)c1ccc(OC)cc1OCc1ccccc1]

Methyl 2-(benzyloxy)-4-butoxybenzoate. By subjecting methyl 4-butoxy-2-hydroxybenzoate (243 mg, 1.08 mmol), K$_2$CO$_3$ (240 mg, 1.73 mmol), benzyl bromide (0.21 mmol, 1.73 mmol), and TBAI (13 mg, 0.04 mmol) to the general procedure for benzylation, the title compound was obtained as a white crystalline solid (312 mg, 0.99 mmol, 92%).

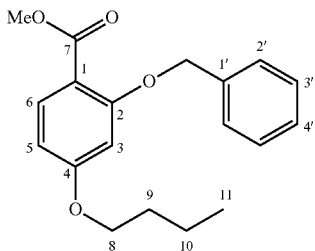 [SMILES: CCCCOc1ccc(C(=O)OC)c(OCc2ccccc2)c1]

Methyl 2-(benzyloxy)-4-heptyloxybenzoate. By subjecting methyl 4-(heptyloxy)-2-hydroxybenzoate (270 mg, 1.01 mmol), benzyl bromide (0.15 mL, 1.21 mmol), K$_2$CO$_3$ (167 mg, 1.21 mmol), and TBAI (28 mg, 0.08 mmol) to the general procedure for benzylation, the title compound was isolated as a colourless oil (318 mg, 0.89 mmol, 88%).

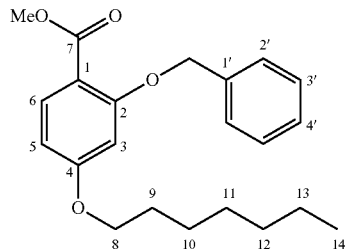 [SMILES: CCCCCCCOc1ccc(C(=O)OC)c(OCc2ccccc2)c1]

Methyl 2-(benzyloxy)-4-(octadecyloxy)benzoate. By subjecting methyl 2-hydroxy-4-(octadecyloxy)benzoate (250 mg, 0.59 mmol), benzyl bromide (0.12 mL, 0.95 mmol), K$_2$CO$_3$ (139 mg, 0.95 mmol), and TBAI (22 mg, 0.059 mmol) to the general procedure for benzylation, the title compound was isolated as an amorphous off-white solid (296 mg, 0.58 mmol, 98%).

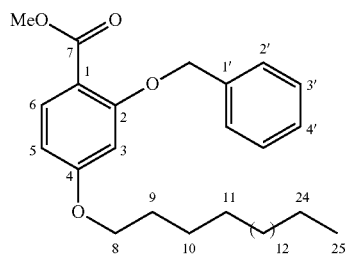

Ethyl 2-(benzyloxy)-6-methyl-4-(octadecyloxy)benzoate. By subjecting ethyl 2-hydroxy-6-methyl-4-(octadecyloxy) benzoate (0.95 g, 2.12 mmol), benzyl bromide (0.38 mL, 3.18 mmol), K$_2$CO$_3$ (480 mg, 3.47 mmol), and TBAI (80 mg, 0.21 mmol) to the general procedure for benzylation, the title compound was isolated as an amorphous solid (622 mg, 1.15 mmol, 54%).

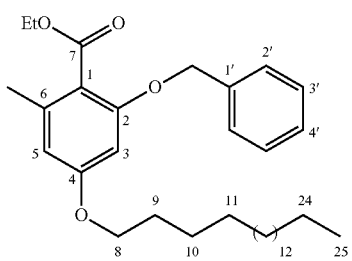

General procedure for ester hydrolysis: To a solution of benzoate in MeOH (20 mL) was added NaOH (5M, 5 mL) and the resulting solution was refluxed overnight. Upon reaction completion (as gauged by TLC) the excess MeOH was removed in vacuo. The resulting suspension was diluted with water, acidified with conc. HCl, extracted with EtOAc, dried with MgSO$_4$, filtered, and concentrated in vacuo.

2-(Benzyloxy)-4-(octadecyloxy)benzoic acid (4a). By subjecting methyl 2-(benzyloxy)-4-(octadecyloxy)benzoate (267 mg, 0.52 mmol) to the general procedure for the hydrolysis benzoates, the title compound was obtained as an amorphous pale orange solid (171 mg, 0.34 mmol, 65%).

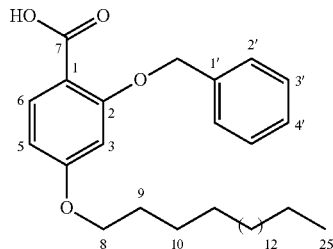

2-(Benzyloxy)-4-(heptyloxy)benzoic acid (4b). By subjecting methyl 2-(benzyloxy)-4-(heptyloxy)benzoate (500 mg, 0.98 mmol) to the general procedure for the hydrolysis of benzoates, the title compound was obtained as an amorphous pale yellow solid (430 mg, 0.87 mmol, 89%).

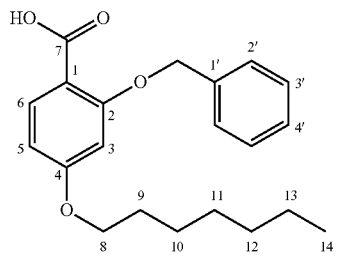 [SMILES: CCCCCCCOc1ccc(C(=O)O)c(OCc2ccccc2)c1]

2-(Benzyloxy)-4-butoxybenzoic acid (4c). By subjecting methyl 2-bis(benzyloxy)-4-butoxybenzoate (320 mg, 1.02 mmol) to the general procedure for the hydrolysis of benzoates, the title compound was obtained as an amorphous white solid (267 mg, 0.89 mmol, 87%).

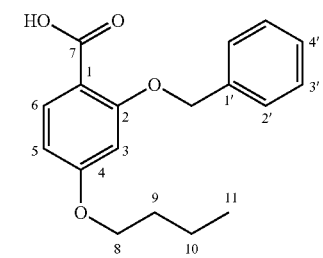 [SMILES: CCCCOc1ccc(C(=O)O)c(OCc2ccccc2)c1]

2-(Benzyloxy)-4-methoxybenzoic acid (4d). By subjecting methyl 2-bis(benzyloxy)-4-methoxybenzoate (511 mg, 1.88 mmol) to the general procedure for the hydrolysis of benzoates, the title compound was obtained as a pale yellow solid (450 mg, 1.74 mmol, 93%).

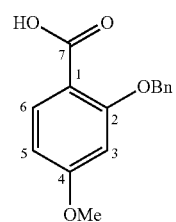

2,4-Bis(benzyloxy)benzoic acid (4e). By subjecting methyl 2,4-bis(benzyloxy)benzoate (431 mg, 1.24 mmol) to the general procedure for the hydrolysis of benzoates, the title compound was obtained as an amorphous off-white solid (384 mg, 1.15 mmol, 93%.

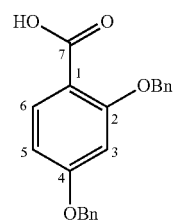

4-(Octadecyloxy)benzoic acid (5a). By subjecting methyl 4-(octadecyloxy)benzoate (962 mg, 2.38 mmol) to the general procedure for the hydrolysis of benzoates, the title compound was obtained as an amorphous white solid (638 mg, 1.63 mmol, 69%).

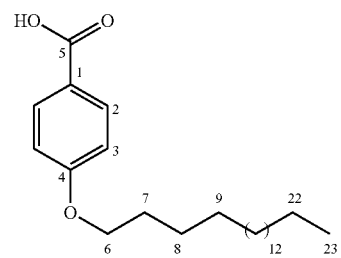

4-(Heptyloxy)benzoic acid (5b). By subjecting methyl 4-(heptyloxy)benzoate (353 mg, 1.41 mmol) to the general procedure for the hydrolysis of benzoates, the title compound was obtained as an amorphous white solid (280 mg, 1.19 mmol, 84%).

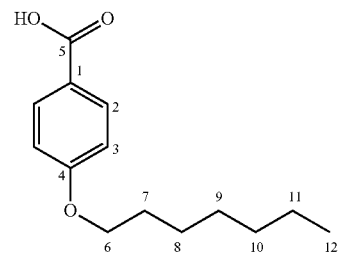 [SMILES: CCCCCCCOc1ccc(C(=O)O)cc1]

2-(Benzyloxy)-6-methyl-4-(octadecyloxy)benzoic acid (6a). By subjecting ethyl 2-(benzyloxy)-6-methyl-4-(octadecyloxy)benzoate (598 mg, 1.11 mmol) to the general procedure for the hydrolysis of benzoates, the title compound was obtained as an amorphous off-white solid (494 mg, 0.97 mmol, 87%).

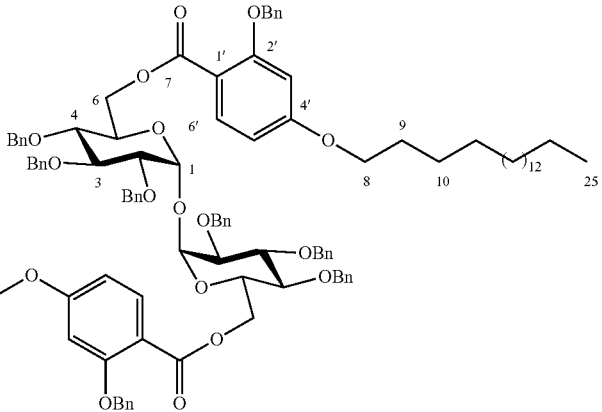

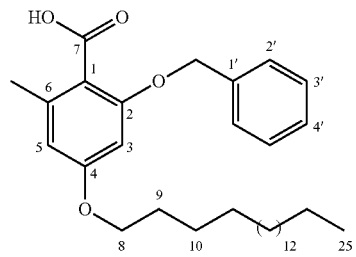

2,4-Bis(benzyloxy)-6-methylbenzoic acid (6b). By subjecting ethyl 2,4-bis(benzyloxy)benzoate (590 mg, 1.57 mmol) to the general procedure for the hydrolysis of benzoates, the title compound was obtained as an amorphous off-white solid (517 mg, 1.48 mmol, 94%).

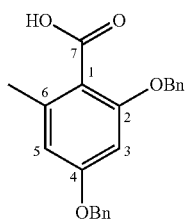 [SMILES: Cc1cc(OCc2ccccc2)cc(OCc2ccccc2)c1C(=O)O]

Preparation of Compounds of the Invention

General procedure for esterification: Diol 7 (1 equiv.) and carboxylic acid (4.5 equiv.) were co-evaporated with toluene (2×20-40 mL/mmol) and then dissolved in dry toluene (10-20 mL/mmol). EDCI (6.5-6.6 equiv.) and DMAP (1 equiv.) were added and the reaction mixture was stirred at 60° C. overnight. Additional reagents were added where necessary and are detailed in the individual procedures. Upon reaction completion (as gauged by TLC analysis) the reaction mixture was diluted with EtOAc, washed with water and brine, dried over $MgSO_4$, filtered, and concentrated in vacuo.

2,2',3,3',4,4'-Hexa-O-benzyl-6,6'-di-O-(2-benzyloxy-4-octadecyloxybenzoyl)-α,α'-D-trehalose (8a). Diol 7 (55 mg, 0.062 mmol), acid 4a (136 mg, 0.274 mmol), EDCI (64 mg, 0.33 mmol), DMAP (11 mg, 0.090 mmol), and toluene (2 mL) were subjected to the conditions described in the general procedure for esterification. After 18 hours, an additional portion of 4a (21 mg, 0.042 mmol) was added before continuing with the general procedure. The resulting residue was purified by gradient silica gel flash column chromatography (petroleum ether:EtOAc, 19:1-9:1, v/v) to give the title compound as a colourless oil (75 mg, 0.041 mmol, 66%). $R_f$=0.56 (petroleum ether:EtOAc, 7:3, v/v); $[α]^{72}_D$=+59.6 (c=1.0, $CH_2Cl_2$); $^1$H NMR (500 MHz, $CDCl_3$) 7.85 (d, $J_{6',5'}$=8.5 Hz, 2H, H-6'), 7.47 (d, J=7.6 Hz, 4H, $CH_{arom}$), 7.24-7.36 (m, 36H, $CH_{arom}$), 6.45-6.48 (m, 4H, H-3' & H-5'), 5.20 (d, $J_{1,2}$=3.3 Hz, 2H, H-1), 5.15 (s, 4H, $CH_2$Ph), 5.01 (d, $J_{a,b}$=10.9 Hz, 2H, $CH_a$ 3-O-Bn), 4.88 (d, $J_{a,b}$=11.1 Hz, 2H, $CH_b$ 3-O-Bn), 4.83 (d, $J_{a,b}$=11.1 Hz, 2H, $CH_a$ 4-O-Bn), 4.64 (s, 4H, $CH_2$ 2-O-Bn), 4.58 (d, $J_{a,b}$=10.7 Hz, 2H, $CH_b$ 4-O-Bn), 4.40 (dd, $J_{6a,6b}$=12.2 Hz, $J_{6a,5}$=3.0 Hz, 2H, H-6a), 4.31-4.35 (m, 4H, H-6b & H-5), 4.07 (t, $J_{3,2}$=$J_{3,4}$=9.2 Hz, 2H, H-3), 3.92 (t, $J_{8,9}$=6.7 Hz, 4H, $CH_2$-8), 3.51 (dd, $J_{2,3}$=9.6 Hz, $J_{2,1}$=3.2 Hz, 2H, H-2), 1.75 (p, $J_{9,8}$=$J_{9,10}$=7.5 Hz, 4H, $CH_2$-9), 1.40-1.46 (m, 4H, $CH_2$-10), 1.25-1.36 (m, 56H, $CH_2$-11-$CH_2$-24), 0.89 (t, $J_{25,24}$=6.8 Hz, 6H, $CH_3$-25); $^{13}$C NMR (125 MHz, $CDCl_3$) δ 165.2 (C-7), 163.8 (C-4'), 160.4 (C-2'), 138.9 ($C_i$, 3-O-Bn), 138.1 ($C_i$, 4-O-Bn), 137.9 ($C_i$, 2-O-Bn), 136.8 ($C_i$, $CH_2$Ph), 133.9 (C-6'), 128.7, 128.6, 128.54, 128.50, 128.3, 128.04, 127.95, 127.82, 127.81, 127.7, 127.6, 126.8 ($CH_{arom}$), 112.5 (C-1'), 105.8 (C-5'), 101.0 (C-3'), 94.0 (C-1), 81.7 (C-3), 79.4 (C-2), 77.9 (C-4), 75.8 ($CH_2$, 3-O—Bn), 75.4 ($CH_2$, 4-O—Bn), 72.9 ($CH_2$, 2-O—Bn), 70.4 ($CH_2$, $CH_2$Ph), 69.5 (C-5), 68.4 (C-8), 62.8 (C-6), 32.1, 29.83, 29.80, 29.79, 29.74, 29.70, 29.51, 29.50, 29.2, 26.1, 22.8 (C-9-C-24), 14.3 (C-25); IR (film): 2922, 2852, 1723, 1606, 1454, 1244, 1069, 1028, 997, 732, 696 $cm^{-1}$; HRMS (ESI) calcd. for $[C_{118}H_{150}O_{17}$+$NH_4]^+$: 1857.1211; obsd.: 1857.1223.

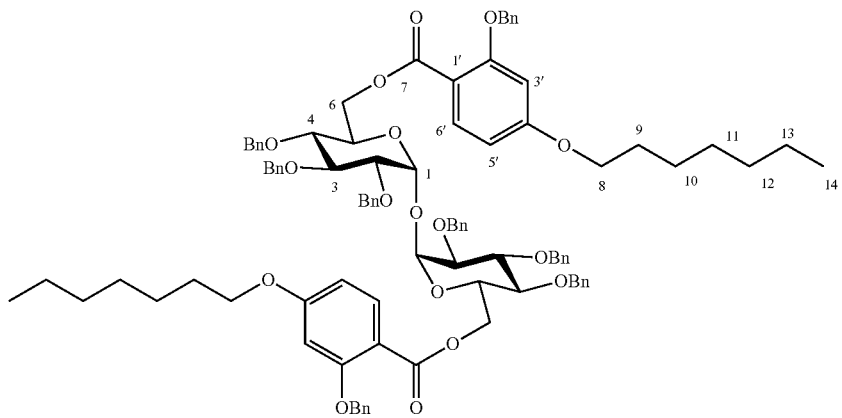

2,2',3,3',4,4'-Hexa-O-benzyl-6,6'-di-O-(2-benzyloxy-4-heptyloxybenzoate)-α,α'-D-trehalose (8b). Diol 7 (114 mg, 0.129 mmol), acid 4b (199 mg, 0.581 mmol), EDCI (161 mg, 0.839 mmol), DMAP (16 mg, 0.129 mmol) and toluene (3 mL) were subjected to the conditions described in the general procedure for esterification. The resulting oil was purified by gradient silica gel flash column chromatography (petroleum ether:EtOAc, 9:1-5:1, v/v) to give the title compound as a colourless oil (138 mg, 0.103 mmol, 70%). $R_f$=0.36 (petroleum ether:EtOAc, 4:1, v/v); $[\alpha]^{21.1}_D$=+74.6 (c=1.0, $CH_2Cl_2$); $^1$H NMR (500 MHz, $CDCl_3$) δ 7.80 (d, $J_{6',5'}$=8.4 Hz, 2H, H-6'), 7.24-7.48 (m, 40H, $CH_{arom}$), 6.43-6.47 (m, 4H, H-3' & H-5'), 5.20 (d, $J_{1,2}$=3.7 Hz, 2H, H-1), 5.15 (s, 4H, $CH_2Ph$), 5.01 (d, $J_{a,b}$=10.6 Hz, 2H, $CH_a$ 3-O—Bn), 4.88 (d, $J_{a,b}$=11.0 Hz, 2H, $CH_b$ 3-O—Bn), 4.83 (d, $J_{a,b}$=10.4 Hz, 2H, $CH_a$ 4-O—Bn), 4.64 (s, 4H, $CH_2$ 2-O—Bn), 4.57 (d, $J_{a,b}$=10.5 Hz, 2H, $CH_b$ 4-O—Bn), 4.40 (dd, $J_{6a,6b}$=12.5 Hz, $J_{6a,5}$=3.5 Hz, 2H, H-6a), 4.31-4.36 (m, 4H, H-5 & H-6b), 4.07 (t, $J_{3,2}$=$J_{3,4}$=9.3 Hz, 2H, H-3), 3.92 (t, $J_{8,9}$=6.7 Hz, 4H, $CH_2$-8), 3.72 (t, $J_{4,3}$=$J_{4,5}$=9.5 Hz, 2H, H-4), 3.51 (dd, $J_{2,3}$=9.6 Hz, $J_{2,1}$=3.4 Hz, 2H, H-2), 1.75 (p, $J_{9,8}$=$J_{9,10}$=6.8 Hz, 4H, $CH_2$-9), 1.40-1.48 (m, 4H, $CH_2$-10), 1.29-1.39 (m, 12H, $CH_2$-11-$CH_2$-13), 0.90 (t, $J_{14,13}$=6.3 Hz, 6H, $CH_3$-14); $^{13}$C NMR δ 165.1 (C-7), 163.7 (C-4'), 160.4 (C-2'), 138.8 (C-i, 3-O—Bn), 138.0 (C-i, 4-O—Bn), 137.8 (C-i, 2-O-n), 136.7 (C-i, $CH_2Ph$), 133.8 (C-6'), 128.6, 128.44, 128.40, 128.2, 127.9, 127.85, 127.72, 127.70, 127.6, 127.5, 126.7 ($CH_{arom}$), 112.4 (C-1'), 105.7 (C-5'), 100.9 (C-3'), 93.9 (C-1), 81.6 (C-3), 79.3 (C-2), 77.8 (C-4), 75.7 ($CH_2$, 3-O—Bn), 75.3 ($CH_2$, 4-O—Bn), 72.8 ($CH_2$, 2-O—Bn), 70.3 ($CH_2Ph$), 69.4 (C-5), 68.2 (C-8), 62.7 (C-6), 31.8, 29.05, 29.02, 25.9, 22.6 (C-9-C-13), 14.1 (C-14); IR (film): 3031, 2928, 2857, 1722, 1606, 1574, 1524, 1498, 1454, 1432, 1378, 1243, 1070, 1070, 997, 734, 696 cm$^{-1}$; HRMS (ESI) calcd. for $[C_{96}H_{106}O_{17}+NH_4]^+$: 1548.7774; obsd.: 1548.7782.

2,2',3,3',4,4'-Hexa-O-benzyl-6,6'-di-O-(2-benzyloxy-4-butoxybenzoyl)-α,α-D-trehalose (8c). Diol 7 (103 mg, 0.117 mmol), acid 4c (158 mg, 0.527 mmol), EDCI (150 mg, 0.782 mmol), DMAP (14.3 mg, 0.117 mmol) and toluene (2.5 mL) were subjected to the conditions described in the general procedure for esterification. The resulting residue was purified by gradient silica gel flash column chromatography (petroleum ether:EtOAc, 9:1-17:3, v/v) to give the title compound as a clear oil (103 mg, 0.071 mmol, 61%). $R_f$=0.67 ($CH_2Cl_2$:EtOAc, 19:1, v/v); $[\alpha]^{16}_D$=+75 (c=1.0, $CH_2Cl_2$); $^1$H NMR (500 MHz, $CDCl_3$) δ 7.83 (d, $J_{6',5'}$=8.4 Hz, 2H, H-6'), 7.25-7.38 (m, 40H, $CH_{arom}$), 6.44-6.47 (m, 4H, H-5' & H-6'), 5.23 (d, $J_{1,2}$=3.4 Hz, 2H, H-1), 5.17 (s, 4H, $CH_2Ph$), 5.03 (d, $J_{a,b}$=10.8 Hz, 2H, $CH_a$ 3-O-n), 4.90 (d, $J_{a,b}$=10.8 Hz, 2H, $CH_b$ 3-O—Bn), 4.85 (d, $J_{a,b}$=10.4 Hz, 2H, $CH_a$ 4-O—Bn), 4.66 (s, 4H, $CH_2$ 2-O—Bn), 4.59 (d, $J_{a,b}$=10.4 Hz, 2H, $CH_b$ 4-O—Bn), 4.42 (dd, $J_{6a,6b}$=12.6 Hz, $J_{6a,5}$=3.3 Hz, 2H, H-6a), 4.31-4.36 (m, 4H, H-5 & H-6b), 4.10 (t, $J_{3,2}$=$J_{3,4}$=9.4 Hz, 2H, H-3), 3.95 (t, $J_{8,9}$=6.4 Hz, 4H, $CH_2$-8), 3.74 (t, $J_{4,3}$=$J_{4,5}$=9.5 Hz, 2H, H-4), 3.54 (dd, $J_{2,3}$=9.6 Hz, $J_{2,1}$=3.5 Hz, 2H, H-2), 1.75 (p, $J_{9,8}$=$J_{9,10}$=6.9 Hz, 4H, $CH_2$-9), 1.49 (sext, $J_{10,9}$=$J_{10,11}$=7.4 Hz, 4H, $CH_2$-10), 0.99 (t, $J_{11,10}$=7.3 Hz, 6H, $CH_3$-11); $^{13}$C NMR (125 MHz, $CDCl_3$) δ 165.2 (C-7), 163.8 (C-4'), 160.4 (C-2'), 138.8 (C-i, 3-O—Bn), 138.0 (C-i, 4-O—Bn), 137.8 (C-i, 2-O-n), 136.7 (C-i, $CH_2Ph$), 133.8 (C-6'), 128.6, 128.5, 128.4, 128.3, 128.0, 127.9, 127.74, 127.72, 127.6, 127.5, 126.7 ($CH_{arom}$), 112.4 (C-1'), 105.8, 101.0 (C-3', C-5), 93.9 (C-1), 81.7 (C-3), 79.3 (C-2), 77.9 (C-4), 75.7 ($CH_2$, 3-O—Bn), 75.3 ($CH_2$, 4-O—Bn), 72.8 ($CH_2$, 2-O-n), 70.3 ($CH_2$, $CH_2Ph$), 69.4 (C-5), 67.9 (C-8), 62.7 (C-6), 31.1 (C-9), 19.2 (C-10), 13.9 (C-11); IR (film): 2932, 2872, 1722, 1606, 1498, 1454, 1433, 1070, 697 cm$^{-1}$; HRMS(ESI) m/z calcd. for $[C_{90}H_{94}O_{17}+H]^+$: 1447.6564; obsd.: 1447.6592.

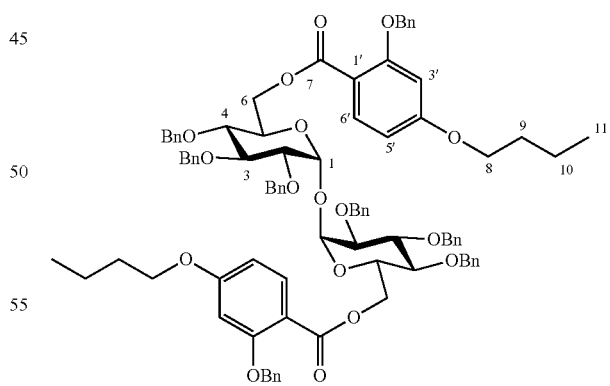

2,2',3,3',4,4'-Hexa-O-benzyl-6,6'-di-O-(2-benzyloxy-4-methoxybenzoyl)-α,α'-D-trehalose (8d). Diol 7 (149 mg, 0.169 mmol), acid 4d (196 mg, 0.760 mmol), EDCI (186 mg, 0.970 mmol), and DMAP (21 mg, 0.172 mmol) were subjected to the conditions described in the general procedure for esterification. After 18 hours, additional portions of 4d (20 mg, 0.077 mmol), EDCI (22 mg, 0.11 mmol), and DMAP (10 mg, 0.082 mmol) were added before continuing with the general procedure. The resulting residue was purified using silica gel flash column chromatography (petroleum ether:EtOAc, 9:1-3:1, v/v) and lipophilic sephadex (CH$_2$Cl$_2$:MeOH, 1:1, v/v) to give the title compound as a colourless oil (150 mg, 0.110 mmol, 65%). R$_f$=0.60 (petroleum ether:EtOAc, 1:1, v/v); [α]$^{18}$$_D$=+79 (c=1.0, CH$_2$Cl$_2$); $^1$H NMR (500 MHz, CDCl$_3$) δ 7.83 (d, J$_{6',5}$=9.2 Hz, 2H, H-6'), 7.47 (d, J=7.7 Hz, 2H, CH$_{arom}$), 7.38-7.25 (m, 38H, CH$_{arom}$), 6.47 (m, 4H, H-5' & H-3'), 5.21 (d, J$_{1,2}$=3.6 Hz, 2H, H-1), 5.16 (s, 4H, CH$_2$Ph), 5.03 (d, J$_{a,b}$=10.9 Hz, 2H, CH$_a$ 3-O—Bn), 4.89 (d, J$_{a,b}$=10.9 Hz, 2H, CH$_b$ 3-O—Bn), 4.84 (d, J$_{a,b}$=10.6 Hz, 2H, CH$_a$ 4-O—Bn), 4.65 (s, 4H, 2-O—Bn), 4.59 (d, J$_{a,b}$=10.5 Hz, CH$_b$ 4-O—Bn), 4.41 (dd, J$_{6a,6b}$=12.5 Hz, J$_{6a,5}$=3.5 Hz, 2H, H-6a), 4.36-4.32 (m, 4H, H-5 & H-6b), 4.09 (t, J$_{3,2}$=J$_{3,4}$=9.3 Hz, 2H, H-3), 3.79 (s, 6H, OMe), 3.73 (t, J$_{4,3}$=J$_{4,5}$=9.4 Hz, 2H, H-4), 3.53 (dd, J$_{2,3}$=9.7 Hz, J$_{2,1}$=3.5 Hz, 2H, H-2); $^{13}$C NMR (125 MHz, CDCl$_3$) δ 165.2 (C-7), 164.2 (C-4'), 160.4 (C-2'), 138.9 (C$_i$, 3-O—Bn), 138.1 (C$_i$, 4-O—Bn), 137.9 (C$_i$, 2-O—Bn), 136.7 (C$_i$, CH$_2$Ph), 134.0 (C-6'), 128.7, 128.57, 128.52, 128.3, 128.1, 127.99, 127.88, 127.83, 127.7, 127.6, 126.8 (CH$_{arom}$), 112.8 (C-1'), 105.2, 100.7 (C-3', C-5'), 94.1 (C-1), 81.7 (C-3), 79.4 (C-2), 77.9 (C-4), 75.8 (CH$_2$, 3-O—Bn), 75.4 (CH$_2$, 4-O-n), 72.9 (CH$_2$, 2-O-n), 70.5 (CH$_2$Ph), 69.5 (C-5), 62.9 (C-6), 55.6 (OMe); IR (film): 3031, 2934, 1722, 1608, 1575, 1498, 1443, 1430, 1380, 1327, 1248, 1147, 1028, 735 cm$^{-1}$; HRMS (ESI) m/z calcd. For [C$_{84}$H$_{82}$O$_{17}$+NH$_4$]$^+$: 1380.5890; obsd.: 1380.5946.

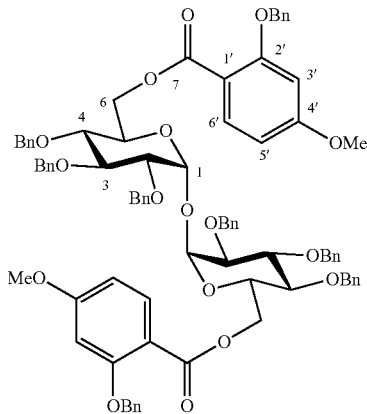

2,2',3,3',4,4'-Hexa-O-benzyl-6,6'-di-O-(2,4-bis(benzyloxy)benzoyl)-α,α'-D-trehalose (8e). Diol 7 (136 mg, 0.154 mmol), acid 4e (231 mg, 0.691 mmol), EDCI (195 mg, 1.02 mmol), DMAP (19 mg, 0.154 mmol), and toluene (2 mL) were subjected to the conditions described in the general procedure for esterification. The residue was purified by gradient silica gel flash column chromatography (petroleum ether to petroleum ether:EtOAc, 17:3, v/v) and lipophilic sephadex (CH$_2$Cl$_2$:MeOH, 1:1, v/v) to give the title compound as a colourless oil (136 mg, 0.090 mmol, 58%). R$_f$=0.63 (petroleum ether:EtOAc, 24:1, v/v); [α]$^{18.4}$$_D$=+55.8 (c=1.0, CH$_2$Cl$_2$); $^1$H NMR (500 MHz, CDCl$_3$) δ 7.82 (d, J$_{6',5}$=8.3 Hz, 2H, H-6'), 7.23-7.46 (m, 50H, CH$_{arom}$), 6.53-6.55 (m, 4H, H-3' & H-5'), 5.22 (d, J$_{1,2}$=3.5 Hz, 2H, H-1), 5.14 (s, 4H, CH$_2$Ph), 5.04 (s, 4H, CH$_2$Ph), 5.04-5.02 (m, 2H, CH$_a$ 3-O—Bn), 4.89 (d, J$_{a,b}$=10.8 Hz, 2H, CH$_b$ 3-O—Bn), 4.85 (d, J$_{a,b}$=10.6 Hz, 2H, CH$_a$ 4-O-n), 4.65 (s, 4H, CH$_2$ 2-O—Bn), 4.59 (d, J$_{a,b}$=10.6 Hz, 2H, CH$_b$ 4-O—Bn), 4.42 (dd, J$_{6a,6b}$=12.4 Hz, J$_{6a,5}$=3.4 Hz, 2H, H-6a), 4.31-4.36 (m, 4H, H-5 & H-6b), 4.09 (t, J$_{3,2}$=J$_{3,4}$=9.3 Hz, 2H, H-3), 3.73 (t, J$_{4,3}$=J$_{4,5}$=9.6 Hz, 2H, H-4), 3.53 (dd, J$_{2,3}$=9.6 Hz, J$_{2,1}$=3.5 Hz, 2H, H-2); $^{13}$C NMR (125 MHz, CDCl$_3$) δ 165.1 (C-7), 163.2, 160.4 (C-2, C-4), 138.8 (Ci, 3-O—Bn), 138.0 (Ci, 4-O-n), 137.9 (Ci, 2-O-n), 136.6 (Ci, CH$_2$Ph), 136.2 (Ci, CH$_2$Ph), 133.9 (C-6'), 128.8, 128.7, 128.5, 128.5, 128.3, 128.3, 128.0, 127.9, 127.9, 127.8, 127.7, 127.6, 127.6, 126.8 (CH$_{arom}$), 113.0 (C-1'), 106.1 (C-3'), 101.5 (C-5), 94.0 (C-1), 81.7 (C-3), 79.3 (C-2), 77.9 (C-4), 75.7 (CH$_{2,3}$-O—Bn), 75.3 (CH$_{2,4}$-O—Bn), 72.8 (CH$_2$, 2-O—Bn), 70.4 (CH$_2$Ph), 70.3 (CH$_2$Ph), 69.5 (C-5), 62.8 (C-6); IR (film): 3030, 2870, 1721, 1606, 1575, 1498, 1454, 1243, 1213, 1175, 1070, 1027, 997, 836, 734, 696 cm$^{-1}$; HRMS(ESI) m/z calcd. For [C$_{96}$H$_{90}$O$_{17}$+NH$_4$]$^+$: 1532.6516; obsd.: 1532.6579.

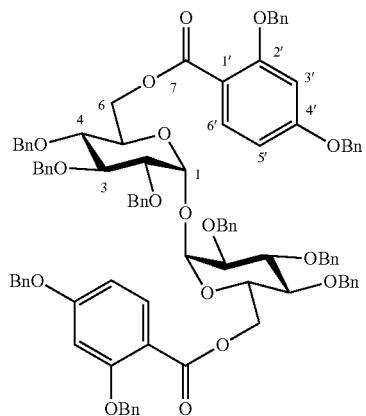

2,2',3,3',4,4'-Hexa-O-benzyl-6,6'-di-O-(4-octadecyloxybenzoyl)-α,α'-D-trehalose (8f). Diol 7 (300 mg, 0.340 mmol), acid 5a (598 mg, 1.53 mmol), EDCI (456 mg, 2.38 mmol), DMAP (42 mg, 0.340 mmol), and toluene (3 mL) were subjected to the conditions described in the general procedure for esterification. The resulting residue was purified by gradient silica gel flash column chromatography (petroleum ether:EtOAc, 19:1, v/v) to give the title compound as a pale yellow oil (442 mg, 0.272 mmol, 80%). R$_f$=0.7 (petroleum ether:EtOAc, 9:1, v/v); [α]$^{23}$$_D$=+55 (c=1.0, CH$_2$Cl$_2$); $^1$H NMR (500 MHz, CDCl$_3$) δ 7.91 (d, J$_{2',3'}$=8.3 Hz, 2H, H-2'), 7.39-7.24 (m, 30H, CH$_{arom}$), 6.85 (d, J$_{3',2'}$=8.3 Hz, 2H, H-3'), 5.23 (d, J$_{1,2}$=3.5 Hz, 2H, H-1), 5.03 (d, J$_{a,b}$=10.7 Hz, 2H, CH$_a$ 3-O—Bn), 4.90 (d, J$_{a,b}$=9.4 Hz, 2H, CH$_b$ 3-O—Bn), 4.88 (d, J$_{a,b}$=9.7 Hz, 2H, CH$_a$ 4-O—Bn), 4.73 (d, J$_{a,b}$=11.9 Hz, 2H, CH$_a$ 2-O—Bn), 4.69 (d, J$_{a,b}$=11.9 Hz, 2H, CH$_b$ 2-O—Bn), 4.57 (d, J$_{a,b}$=10.7 Hz, 2H, CH$_b$ 4-O—Bn), 4.29-4.34 (m, 4H, H-5 & H-6a), 1.46 (dd, J$_{6a,6b}$=12.4 Hz, J$_{6b,5}$=3.2 Hz, 2H, H-6b), 4.11 (t, J$_{3,2}$=J$_{3,4}$=9.4 Hz, 2H, H-3), 3.98 (t, J$_{8,9}$=6.5 Hz, 4H, CH$_2$-8), 3.68 (t, J$_{4,3}$=J$_{4,5}$=9.6 Hz, 2H, H-4), 3.62 (dd, J$_{2,3}$=9.5 Hz, J$_{2,1}$=3.2 Hz, 2H, H-2), 1.79 (p, J$_{9,8}$=J$_{9,10}$=6.9 Hz, 4H, CH$_2$-9), 1.40-1.48 (m, 2H, CH$_2$-10), 1.38-1.24 (m, 56H, CH$_2$-11-CH$_2$-24), 0.90 (t, J$_{25,24}$=6.5 Hz, 3H, CH$_3$-25); $^{13}$C NMR (125 MHz, CDCl$_3$) δ 166.1 (C-7), 163.2 (C-4'), 138.7 (Ci, 3-O—B3n), 138.0 (Ci, 4-O—B3n), 137.9 (C$_i$, 2-O—Bn), 131.8 (C-2'), 128.64, 128.63, 128.62, 128.3, 128.25, 128.1, 127.92, 127.90, 127.6 (CH$_{arom}$), 122.1 (C-1'), 114.2 (C-3'), 94.1 (C-1), 81.9 (C-3), 79.7 (C-2), 77.9 (C-4), 76.1 (CH$_2$, 3-O—Bn), 75.5 (CH$_2$, 4-O—Bn), 73.1 (CH$_2$, 2-O—Bn), 69.5 (C-5), 68.4 (C-8), 62.9 (C-6), 32.1, 31.7, 29.85, 29.83, 29.83, 29.76, 29.72, 29.54, 29.52, 29.3 27.1, 26.2 (C-9-C-24), 22.9 (C-25); IR (film): 2922, 2852, 1716, 1605, 1454, 1273, 1166, 1096, 1070, 996, 695 cm$^{-1}$; HRMS (ESI) calcd. for [C$_{104}$H$_{138}$O$_{17}$+NH$_4$]$^+$: 1645.0374; obsd.: 1645.0373.

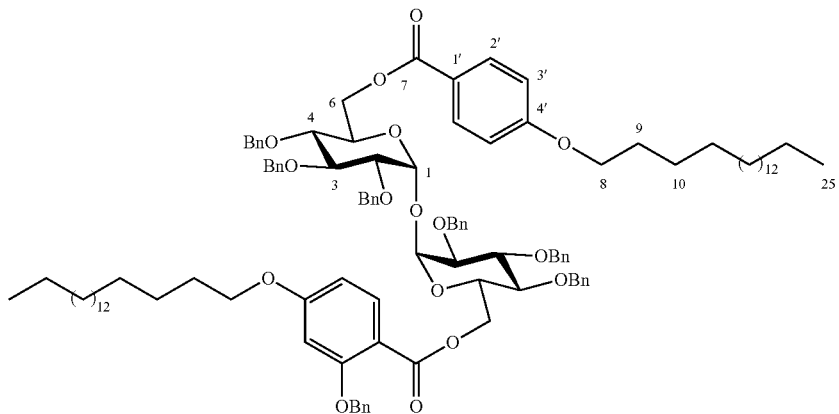

2,2',3,3',4,4'-Hexa-O-benzyl-6,6'-di-O-(4-heptyloxybenzoyl)-α,α'-D-trehalose (8g). Diol 7 (89 mg, 0.10 mmol), acid 5b (106 mg, 0.45 mmol), EDCI (125 mg, 0.65 mmol), DMAP (12 mg, 0.10 mmol), and toluene (2 mL) were subjected to the conditions described in the general procedure for esterification. The resulting residue was purified using gradient silica gel flash column chromatography (petroleum ether:EtOAc, 1:0-17:3, v/v) to give the title compound as a colourless oil (109 mg, 0.083 mmol, 83%). $R_f$=0.5 (petroleum ether:EtOAc, 4:1, v/v); $[\alpha]^{23}_D$=+67 (c=1.0, $CH_2Cl_2$); $^1$H-NMR (500 MHz, $CDCl_3$) δ 7.93 (d, $J_{2',3'}$=7.8 Hz, 4H, H-2'), 7.40-7.26 (m, 30H, $CH_{arom}$), 6.87 (d, $J_{3',2'}$=8.1 Hz, 4H, H-3'), 5.25 (d, $J_{1,2}$=3.0 Hz, 2H, H-1), 5.05 (d, $J_{a,b}$=10.5 Hz, 2H, $CH_a$ 3-O—Bn), 4.91 (d, $J_{a,b}$=9.3 Hz, 2H, $CH_b$ 3-O—Bn), 4.91 (d, $J_{a,b}$=9.3 Hz, 2H, $CH_a$ 4-O—Bn), 4.75 (d, $J_{a,b}$=11.8 Hz, 2H, $CH_a$ 2-O—Bn), 4.71 (d, $J_{a,b}$=11.7 Hz, 2H, $CH_b$ 2-O—Bn), 4.58 (d, $J_{a,b}$=10.8 Hz, 2H, $CH_b$ 4-O—Bn), 4.35-4.26 (m, 6H, $CH_2$-6 & H-5), 4.13 (t, $J_{3,2}$=$J_{3,4}$=9.4 Hz, 2H, H-3), 4.00 (t, $J_{8,9}$=6.4 Hz, 4H, $CH_2$-8), 3.70 (t, $J_{4,3}$=$J_{4,5}$=9.5 Hz, 2H, H-4), 3.64 (dd, $J_{2,3}$=9.5 Hz, $J_{2,1}$=2.7 Hz, 2H, H-2), 1.80 (p, $J_{9,8}$=$J_{9,10}$=6.9 Hz, 4H, $CH_2$-9), 1.47 (p, $J_{10,9}$=$J_{10,11}$=7.5 Hz, 4H, $CH_2$-10), 1.40-1.32 (m, 12H, $CH_2$-11-$CH_2$-13), 0.91 (t, $J_{14,13}$=6.4 Hz, 6H, $CH_3$-14); $^{13}$C NMR (125 MHz, $CDCl_3$) δ 166.0 (C-7), 163.1 (C-4') 138.5 ($C_i$, 3-O—Bn), 137.8 ($C_i$, 4-O—Bn), 137.8 ($C_i$, 2-O—Bn), 131.7 (C-2'), 128.5, 128.5, 128.2, 128.1, 128.0, 127.8, 127.8, 127.4 ($CH_{arom}$), 122.0 (C-1'), 114.1 (C-3'), 94.0 (C-1), 81.7 (C-3), 79.5 (C-2), 77.7 (C-4), 75.9 ($CH_2$, 3-O-n), 75.3 ($CH_2$, 4-O-n), 73.0 ($CH_2$, 2-O-n), 69.4 (C-5), 68.2 (C-8), 62.7 (C-6), 31.8, 22.6, 29.1, 25.9 (C-9-C-13), 29.0 (C-10), 14.1 (C-14); IR (film): 3064, 3031, 2927, 2856, 1715, 1605, 1510, 1454, 1252, 1166, 846, 734, 696 $cm^{-1}$; HRMS (ESI) calcd. for $[C_{82}H_{95}NO_{15}]^+$: 1336.6931; obsd.: 1336.6870.

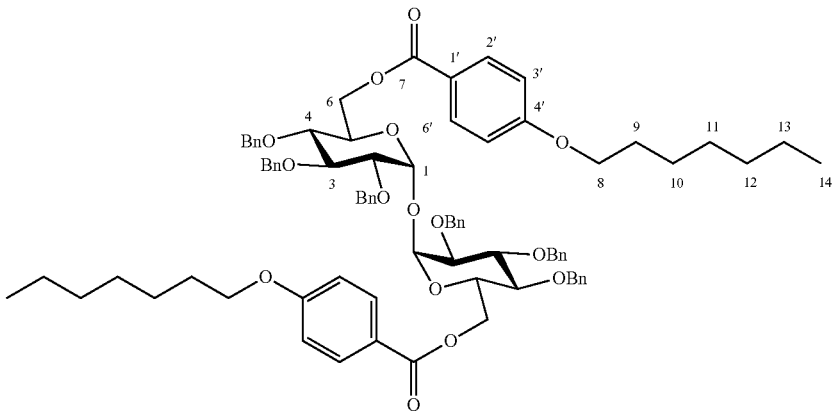

2,2',3,3',4,4'-Hexa-O-benzyl-6,6'-di-O-(2-benzyloxy-6-methyl-4-octadecyloxybenzoyl)-α,α'-D-trehalose (8h). Diol 7 (115 mg, 0.13 mmol), acid 6a (290 mg, 0.568 mmol), EDCI (139 mg, 0.73 mmol), DMAP (17 mg, 0.139 mmol), and toluene (3 mL) were subjected to the conditions described in the general procedure for esterification. After 18 hours, additional portions of 8h (83 mg, 0.16 mmol) and EDCI (25 mg, 0.13 mmol) were added before continuing with the general procedure. The resulting residue was purified using gradient silica gel flash column chromatography (petroleum ether:EtOAc, 19:1-9:1, v/v) to give the title compound as colourless oil (166 mg, 0.089 mmol, 68%). $R_f$=0.83 ($CH_2Cl_2$); $[\alpha]^{22.4}_D$+47.5 (c=1.0, $CH_2Cl_2$); $^1$H NMR (500 MHz, $CDCl_3$) δ 7.30-7.10 (m, 40H, $CH_{arom}$), 6.25 (s, 2H, H-5), 6.22 (s, 2H, H-3'), 5.07 (d, $J_{1,2}$=3.2 Hz, 2H, H-1), 4.97 (s, 4H, $CH_2Ph$), 4.94 (d, $J_{a,b}$=10.6 Hz, 2H, $CH_a$ 3-O—Bn), 4.79 (d, $J_{a,b}$=10.9 Hz, 2H, $CH_b$ 3-O-n), 4.73 (d, $J_{a,b}$=10.5 Hz, 2H, $CH_a$ 4-O—Bn), 4.55-4.46 (m, 8H, H-6a, $CH_b$ 4-O—Bn, $CH_2$ 2-O—Bn), 4.24 (d, $J_{6a,6b}$=10.5 Hz, 4H, H-5 & H-6b), 3.98 (t, $J_{3,2}$=$J_{3,4}$=9.2 Hz, 2H, H-3), 3.83 (t, $J_{8,9}$=6.5 Hz, 4H, $CH_2$-8), 3.57 (t, $J_{4,3}$=$J_{4,5}$=9.3 Hz, 2H, H-4), 3.41 (dd, $J_{2,3}$=9.6 Hz, $J_{2,1}$=3.2 Hz, 2H, H-2), 2.23 (s, 6H, 6-Me), 1.70 (p, $J_{9,8}$=$J_{9,10}$=6.8 Hz, 4H, CH$_2$-9), 1.38-1.45 (m, 2H, CH$_2$-10), 1.32-1.22 (m, CH$_2$-11-CH$_2$-24), 0.86 (t, $J_{25,24}$=6.9 Hz, 6H, CH$_3$-25); $^{13}$C NMR (125 MHz, CDCl$_3$) δ 168.2 (C-7), 160.9 (C-4'), 157.2 (C-2'), 139.0 (C$_i$, 3-O—Bn), 138.4 (C-6'), 138.2 (C$_i$, 4-O-n), 138.0 (C$_i$, 2-O-n), 136.9 (C$_i$, CH$_2$Ph), 128.6, 128.5, 128.45, 128.43, 128.3, 127.9, 127.8, 127.79, 127.7, 127.6, 127.6, 126.8 (CH$_{arom}$), 116.7 (C-1'), 107.9 (C-5'), 98.1 (C-3'), 93.7 (C-1), 81.5 (C-3), 79.2 (C-2), 78.0 (C-4), 75.6 (CH$_2$, 3-O-n), 75.3 (CH$_2$, 4-O-n), 72.6 (CH$_2$, 2-O—Bn), 70.2 (CH$_2$, CH$_2$Ph), 69.4 (C-5), 68.2 (C-8), 63.2 (C-6), 32.1, 29.86, 29.81, 29.78, 29.74, 29.55, 29.52, 22.9 (C-11-C-24), 29.3 (C-9), 26.2 (C-10), 20.2 (6-Me), 14.3 (C-25); IR (film): 2923, 2853, 1728, 1604, 149997, 1375, 1327, 1262, 1164, 1093, 1071, 998, 734, 696 cm$^{-1}$; HRMS (ESI) calcd for [C$_{120}$H$_{154}$O$_{17}$+H]$^+$: 1868.1259; obsd.: 1868.1275.

4.26 (m, 4H, H-6b & H-5), 4.00 (t, $J_{3,2}$=$J_{3,4}$=9.3 Hz, 2H, H-3), 3.59 (t, $J_{4,3}$=$J_{4,5}$=9.4 Hz, 2H, H-4), 3.43 (dd, $J_{2,3}$=9.6 Hz, $J_{2,1}$=3.5 Hz, 2H, H-2), 2.25 (s, 6H, 6-Me); $^{13}$C NMR (125 MHz, CDCl$_3$) δ 168.1 (C-7), 160.5 (C-4'), 157.2 (C-2'), 139.0 (C$_i$, 3-O-n), 138.4 (C-6'), 138.2 (C, 4-O-n), 138.0 (C, 2-O-n), 136.74 (C$_i$, CH$_2$Ph), 136.65 (C$_i$, CH$_2$Ph), 117.2 (C-1'), 108.2 (C-5'), 98.5 (C-3'), 93.8 (C-1), 81.5 (C-3), 79.2 (C-2), 77.9 (C-4), 75.6 (CH$_2$, 3-O—Bn), 75.4 (CH$_2$, 4-O—Bn), 72.7 (CH$_2$Ph), 69.5 (C-5), 63.3 (C-6), 20.2 (6-Me), 20.2 (6-Me); IR (film): 3031, 2926, 2871, 1727, 1603, 1497, 1454, 1372, 1326, 1264, 1159, 1092, 1071, 997, 735, 697 cm$^{-1}$; HRMS (ESI) calcd. for [C$_{95}$H$_{94}$O$_{17}$+NH$_4$]$^+$: 1560.6829; obsd.: 1560.6894.

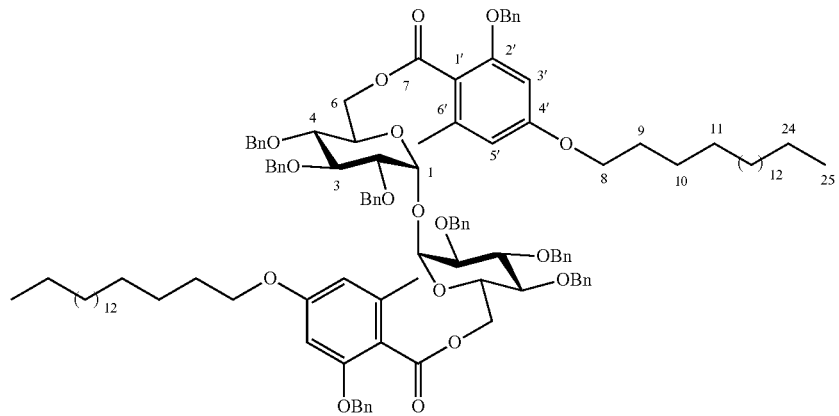

2,2',3,3',4,4'-Hexa-O-benzyl-6,6'-di-O-(2,4-benzyloxy-6-methylbenzoyl)-α,α'-D-trehalose (8i). Diol 7 (166 mg, 0.188 mmol), acid 6b (295 mg, 0.847 mmol), EDCI (190 mg, 0.991 mmol), DMAP (23 mg, 0.188 mmol), and toluene (2.5 mL) were subjected to the conditions described in the general procedure for esterification. After 18 hours, additional portions of 6b (70 mg, 0.20 mmol) and EDCI (36 mg, 0.188 mmol) were added. After a further 18 hours, 6b (52 mg, 0.15 mmol), EDCI (35 mg, 0.18 mmol), and DMAP (20 mg, 0.16 mmol) were added before continuing with the general procedure. The resulting residue was purified by gradient silica gel flash column chromatography (petroleum ether:EtOAc, 1:0-4:1, v/v) to give the title compound as a colourless oil (150 mg, 0.097 mmol, 52%). $R_f$=0.76 (petroleum ether:EtOAc, 1:1, v/v); [α]$^{23}_D$=+67.8 (c=1.0, CH$_2$Cl$_2$); $^1$H NMR (500 MHz, CDCl$_3$) δ 7.40-7.14 (m, 50H, CH$_{arom}$), 6.36 (d, $J_{5',3'}$=1.8 Hz, 2H, H-5'), 6.31 (d, $J_{3',5'}$=1.9 Hz, 2H, H-3'), 5.10 (d, $J_{1,2}$=3.5 Hz, 2H, H-1), 4.90-4.99 (m, 8H, CH$_2$Ph, CH$_a$ 4'-O—Bn & CH$_a$ 3-O—Bn), 4.82 (d, $J_{a,b}$=11.1 Hz, 2H, CH$_b$ 3-O—Bn), 4.75 (d, $J_{a,b}$=10.3 Hz, 2H, CH$_a$ 4-O—Bn), 4.57-4.49 (m, 8H, CH$_b$ 4-O-n, CH$_2$Ph, H-6a),

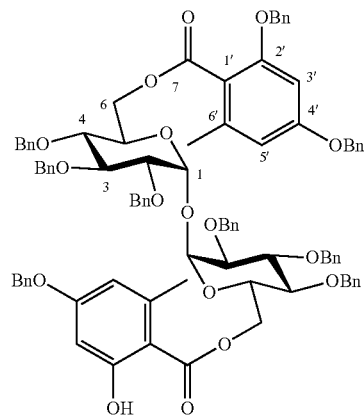

General procedure for debenzylation: To a solution of benzyl-protected trehalose diester (1 equiv.) dissolved in MeOH:CH$_2$Cl$_2$ (5 mL, 1:1, v/v) was added Pd(OH)$_2$/C. H$_2$-gas was allowed to bubble through the reaction mixture overnight. Following reaction completion (as gauged by TLC) the suspension was diluted in pyridine and filtered over celite.

6,6'-Di-O-(2-hydroxy-4-octabenzyloxybenzoyl)-α,α'-D-trehalose (9a). Benzyl protected trehalose 8a (140 mg, 0.076 mmol) and Pd(OH)$_2$/C were subjected to the conditions described in the general procedure for debenzylation. The resulting OH residue was purified using gradient silica gel flash column chromatography (EtOAc:MeOH, 1:0-9:1, v/v) and lipophilic sephadex (CH$_2$Cl$_2$:MeOH, 1:1, v/v) to give the title compound as an amorphous white solid (58 mg, 0.052 mmol, 68%). R$_f$=0.37 (EtOAc); [α]$^{21.6}_D$=+52 (c=0.1, pyridine); $^1$H NMR (500 MHz, C$_5$D$_5$N) δ 11.41 (s, 2H, OH), 8.06 (d, J$_{6',5'}$=8.7 Hz, 2H, H-6'), 6.71 (d, J$_{3',5'}$=1.7 Hz, 2H, H-3'), 6.47 (dd, J$_{5',6'}$=8.9 Hz, J$_{5',3'}$=2.0 Hz, 2H, H-5'), 5.91 (d, J$_{1,2}$ 25=3.4 Hz, 2H, H-1), 5.12-5.15 (m, 4H, H-5 & H-6a), 4.99 (dd, J$_{6b,6a}$=11.6 Hz, J$_{6b,5}$=5.5 Hz, 2H, H-6b), 4.80 (t, J$_{3,2}$=J$_{3,4}$=9.1 Hz, 2H, H-3), 4.37 (dd, J$_{2,3}$=9.6 Hz, J$_{2,1}$=3.6 Hz, 2H, H-2), 4.23 (t, J$_{4,3}$=J$_{4,5}$=9.3 Hz, 2H, H-4), 3.91 (t, J$_{8,9}$=6.5 Hz, 4H, CH$_2$-8), 1.71 (p, J$_{9,8}$=J$_{9,10}$=7.3 Hz, 4H, CH$_2$-9), 1.38-1.43 (m, 4H, CH$_2$-10), 1.24-35 (m, 56H, CH$_2$-11-CH$_2$-24), 0.87 (t, J$_{25,24}$=6.8 Hz, 6H, CH$_3$-25); $^{13}$C NMR (125 MHz, C$_5$D$_5$N) δ 170.7 (C-7), 166.0 (C-4'), 164.6 (C-2'), 132.4 (C-6'), 108.5 (C-5'), 106.5 (C-1'), 102.2 (C-3'), 96.5 (C-1), 75.4 (C-3), 73.7 (C-2), 72.4 (C-4), 71.8 (C-5), 68.9 (C-8), 65.6 (C-6), 32.5, 30.4, 3.37, 30.36, 30.34, 30.29, 30.26, 30.22 29.98, 23.3 (C-11-C-24), 29.6 (C-9), 26.6 (C-10), 14.7 (C-25); IR (film): 3403, 2917, 2849, 1698, 1662, 1504,1395, 1252, 1151, 1095, 1075, 1017, 987, 804, 770, 672 cm$^{-1}$; HRMS (ESI) calcd. For [C$_{62}$H$_{103}$O$_{17}$+H]$^+$: 1119.7190; obsd. 1119.7169.

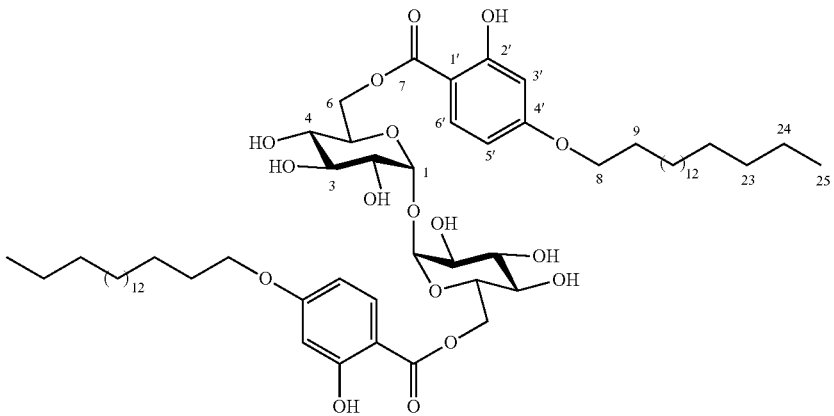

6,6'-Di-O-(4-heptyloxy-2-hydroxybenzoyl)-α,α'-D-trehalose (9b). Benzyl protected trehalose 8b (138 mg, 0.090 mmol) and Pd(OH)$_2$/C (83 mg) were subjected to the conditions described in the general procedure for debenzylation. The resulting residue was purified using gradient silica gel flash column chromatography (EtOAc:petroleum ether-EtOAc:MeOH, 4:1-9:1, v/v) to give the title compound as an amorphous white solid (61 mg, 0.075 mmol, 83%). R$_f$=0.76 (EtOAc:MeOH, 4:1, v/v); [α]$^{20}_D$=+46.0 (c=0.1, pyridine); $^1$H NMR (500 MHz, C$_5$D$_5$N) δ 11.44 (s, 2H, OH), 8.06 (d, J$_{6',5'}$=8.9 Hz, 2H, H-6'), 6.72 (d, J$_{3',5'}$=2.4 Hz, 2H, H-3'), 6.47 (dd, J$_{5',6'}$=8.9 Hz, J$_{5',3'}$=2.4 Hz, 2H, H-5), 5.93 (d, J$_{1,2}$=3.7 Hz, 2H, H-1), 5.23-5.27 (m, 2H, H-5), 5.12 (d, J$_{6a,6b}$=11.5 Hz, 2H, H-6a), 5.01 (dd, J$_{6b,6a}$=11.7 Hz, J$_{6b,5}$=5.6 Hz, 2H, H-6b), 4.80 (t, J$_{3,2}$=J$_{3,4}$=9.2 Hz, 2H, H-3), 4.37 (dd, J$_{2,3}$=9.7 Hz, J$_{2,1}$=3.8 Hz, 2H, H-2), 4.24 (t, J$_{4,3}$=J$_{4,5}$=9.4 Hz, 2H, H-4), 3.89 (t, J$_{8,9}$=6.5 Hz, 4H, CH$_2$-8), 1.67 (p, J$_{9,8}$=J$_{9,10}$=6.8 Hz, 4H, CH$_2$-9), 1.31-1.38 (m, 4H, CH$_2$-10), 1.16-1.26 (m, 12H, CH$_2$-11-CH$_2$-13), 0.85 (t, J$_{14,13}$=7.1 Hz, 6H, CH$_3$-14); $^{13}$C NMR (500 MHz, C$_5$D$_5$N) δ 170.6 (C-7), 165.9 (C-4'), 164.6 (C-2'), 132.4 (C-6'), 108.4 (C-5), 106.5 (C-1'), 102.2 (C-3'), 96.4 (C-1), 75.4 (C-3), 73.7 (C-2), 72.4 (C-4), 71.8 (C-5), 68.9 (C-8), 65.6 (C-6), 32.3, 29.6, 29.5, 26.5, 23.2 (C-9-C-13), 14.6 (C-14); IR (film): 3340, 2926, 2856, 1668, 1152, 991, 777 cm$^{-1}$; HRMS (ESI) calcd. For [C$_{40}$H$_{58}$O$_{17}$+H]$^+$: 811.3747; obsd. 811.3761.

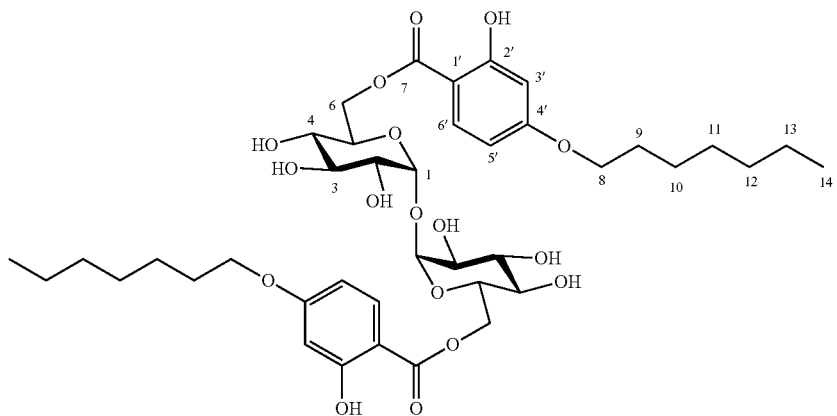

6,6'-Di-O-(2-hydroxy-4-butoxybenzoyl)-α,α'-D-trehalose (9c). Benzyl protected trehalose 8c (82 mg, 0.056 mmol) and Pd(OH)$_2$/C (49 mg) were subjected to the conditions described in the general procedure for debenzylation. The crude material was purified by gradient silica gel flash column chromatography (petroleum ether:EtOAc-EtOAc:MeOH, 1:1-17:3, v/v) and the title compound was obtained as an amorphous white solid (35 mg, 0.048 mmol, 86%). R$_f$=0.26 (EtOAc); [α]$^{20}{}_D$=+69.8 (c=1, pyridine); $^1$H NMR (500 MHz, C$_5$D$_5$N) δ 11.44 (s, 2H, OH), 8.05 (d, J$_{6',5'}$=8.8 Hz, 2H, H-6'), 6.68 (d, J$_{3',4'}$=2.5 Hz, 2H, H-3'), 6.43 (dd, J$_{5',6'}$=8.9 Hz, J$_{5',3'}$=2.5 Hz, 2H, H-5'), 5.94 (d, J$_{1,2}$=3.7 Hz, 2H, H-1) 5.26 (ddd, J$_{5,4}$=10.0 Hz, J$_{5,6a}$=5.3 Hz, J$_{5,6b}$=1.8 Hz, 2H, H-5), 5.13 (dd, J$_{6a,6b}$=11.7 Hz, J$_{6b,5}$=2.0 Hz, 2H, H-6b), 5.01 (dd, J$_{6a,6b}$=11.7 Hz, J$_{6a,5}$=5.5 Hz, H-6a), 4.81 (t, J$_{3,2}$=J$_{3,4}$=9.2 Hz, 2H, H-3), 4.38 (dd, J$_{2,3}$=9.6 Hz, J$_{2,1}$=3.8 Hz, 2H, H-2), 4.24 (t, J$_{4,3}$=J$_{4,5}$=9.6 Hz, 2H, H-4), 3.85 (t, J$_{8,9}$=6.5 Hz, 4H, CH$_2$-8), 1.62 (pent, J$_{9,8}$=J$_{9,10}$=7.7 Hz, 4H, CH$_2$-9), 1.35 (sext, J$_{10,9}$=J$_{10,11}$=7.5 Hz, 4H, CH$_2$-10), 0.84 (t, J$_{11,10}$=7.4 Hz, 6H, CH$_3$-11); $^{13}$C NMR (125 MHz, C$_5$D$_5$N) δ 170.7 (C-7), 165.9 (C-4'), 164.6 (C-2'), 132.4 (C-6'), 108.4 (C-5'), 106.5 (C-1'), 102.2 (C-3'), 96.5 (C-1), 75.4 (C-3), 73.7 (C-2), 72.4 (C-4), 71.8 (C-5), 68.5 (C-8), 65.6 (C-6), 31.5 (C-9), 19.7 (C-10), 14.2 (C-11); IR (film): 3293, 2959, 1668, 1622, 1580, 1504, 1351, 1249, 1151, 1084, 991, 776 cm$^{-1}$; HRMS (ESI) calcd for [C$_{43}$H$_{46}$O$_7$+H]$^-$: 727.2813; obsd.: 727.2813.

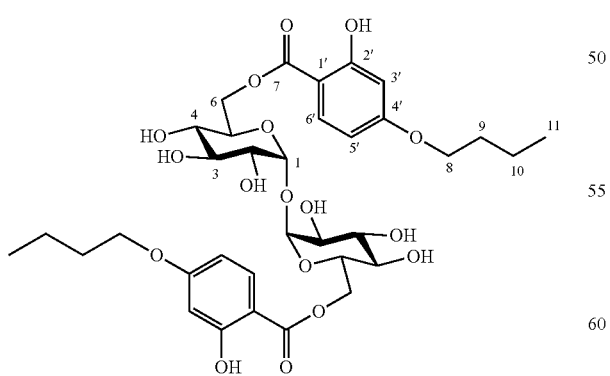

6,6'-Di-O-(2-hydroxy-4-methoxybenzoyl)-α,α'-D-trehalose (9d). Benzyl protected trehalose 8d (86 mg, 0.068 mmol) and Pd(OH)$_2$/C (52 mg) were subjected to the general procedure for debenzylation. The resulting residue was purified by gradient silica gel flash column chromatography (EtOAc:MeOH, 1:0-9:1, v/v) and the title was obtained as an amorphous white solid (27 mg, 0.042 mmol, 62%). R$_f$=0.66 (EtOAc:MeOH, 4:1, v/v); [α]$^{20}{}_D$=+103.6 (c=1, MeOH); $^1$H NMR (500 MHz, C$_5$D$_5$N) δ 11.42 (s, 2H, OH), 8.02 (d, J$_{6',5'}$=8.9 Hz, 2H, H-6'), 6.65 (d, J$_{3',5}$=2.5 Hz, 2H, H-3'), 6.38 (dd, J$_{5',6'}$=8.9 Hz, J$_{5',3}$=2.5 Hz, 2H, H-5'), 5.93 (d, J$_{1,2}$=3.7 Hz, 2H, H-1), 5.26 (ddd, J$_{5,4}$=10.0 Hz, J$_{5,6a}$=5.4 Hz, J$_{5,6b}$=1.9 Hz, 2H, H-5), 5.12 (dd, J$_{6a,6b}$=11.6 Hz, J$_{6a,5}$=2.0 Hz, 2H, H-6a), 5.01 (dd, J$_{6a,6b}$=11.6 Hz, J$_{6b,5}$=5.6 Hz, 2H, H-6b), 4.81 (t, J$_{3,2}$=J$_{3,4}$=9.2 Hz, 2H, H-3), 4.38 (dd, J$_{2,3}$=9.6 Hz, J$_{2,1}$=3.7 Hz, 2H, H-2), 4.24 (t, J$_{4,3}$=J$_{4,5}$=9.5 Hz, 2H, H-4), 3.62 (s, 3H, OMe); $^{13}$C NMR (125 MHz, C$_5$D$_5$N) δ 170.6 (C-7), 166.3 (C-4'), 164.6 (C-2'), 132.4 (C-6'), 108.0 (C-5), 106.6 (C-1'), 101.7 (C-3'), 96.5 (C-1), 75.4 (C-3), 73.7 (C-2), 72.4 (C-4), 71.8 (C-5), 65.7 (C-6), 55.8 (OMe); IR (film): 3258, 2919, 1664, 1622, 1504, 1441, 1351, 1249, 1149, 988, 803 cm$^{-1}$; HRMS (ESI) calcd. for [C$_{28}$H$_{34}$O$_{17}$+Na]$^+$: 665.1688; obsd.: 665.1715.

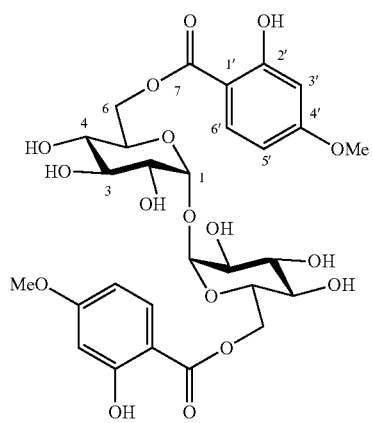

6,6'-Di-O-(2,4-dihydroxybenzoyl)-α,α'-D-trehalose (9e). Benzyl protected trehalose 8e (58.3 mg, 0.038 mmol) and Pd(OH)$_2$/C (35 mg) were subjected to the conditions described in the general procedure for debenzylation. The resulting residue was purified by gradient silica gel flash column chromatography (petroleumether:EtOAc-EtOAc:MeOH, 4:1-4:1, v/v) to give the title compound as an off-white solid (21.8 mg, 0.035 mmol, 92%). R$_f$=0.47 (MeOH:EtOAc, 1:4, v/v); [α]$^{20}{}_D$=+32.8 (c=0.25, pyridine); $^1$H NMR (500 MHz, CD$_3$OD) δ 7.73 (d, J$_{6',5'}$=7.3 Hz, 2H, H-6'), 6.34 (d, $J_{5',6'}$=8.2 Hz, 2H, H-5), 6.29 (s, 2H, H-3'), 5.12 (d, $J_{1,2}$=3.3 Hz, 2H, H-1), 4.55 (bd, $J_{6a,6b}$=11.7 Hz, 2H, H-6a), 4.46 (dd, $J_{6a,6b}$=11.6 Hz, $J_{5,6b}$=4.5 Hz, 2H, H-6b), 4.16-4.22 (m, 2H, H-5), 3.83 (t, $J_{3,2}$=$J_{3,4}$=9.0 Hz, 2H, H-3), 3.53 (dd, $J_{2,3}$=9.5 Hz, $J_{2,1}$=3.1 Hz, 2H, H-2), 3.44 (t, $J_{4,3}$=$J_{4,5}$=9.4 Hz, 2H, H-4); $^{13}$C NMR (125 MHz, CD$_3$OD) δ 171.1 (C-7), 166.4 (C-4'), 164.9 (C-2'), 132.8 (C-6'), 109.5 (C-5), 105.2 (C-1'), 103.6 (C-3'), 95.5 (C-1), 74.6 (C-3), 73.1 (C-2), 71.8 (C-4), 71.5 (C-5), 64.6 (C-6); IR (film): 3232, 2926, 1657, 1622, 1454, 1393, 1340, 1259, 1147, 1094, 1075, 1043, 1018, 977, 772 cm$^{-1}$; HRMS (ESI) calcd for [C$_{26}$H$_{40}$O$_{17}$+NH$_4$]$^+$: 632.1821; obsd.: 632.1822.

[α]$^{20.0}_D$=+67.8 (c=0.1, pyridine); $^1$H NMR (500 MHz, C$_5$D$_5$N) δ 8.29 (d, $J_{2',3}$=8.6 Hz, 4H, H-2'), 6.96 (d, $J_{3',2}$=8.9 Hz, 4H, H-3'), 5.98 (d, $J_{1,2}$=3.7 Hz, 2H, H-1), 5.27-5.31 (m, 2H, H-5), 5.21 (d, $J_{6a,5}$=11.4 Hz, 2H, H-6a), 5.06-5.09 (m, 2H, H-6b), 4.83 (t, $J_{3,2}$=$J_{3,4}$=9.2 Hz, 2H, H-3), 4.40 (dd, $J_{2,3}$=9.6 Hz, $J_{2,1}$=3.6 Hz, 2H, H-2), 4.29 (t, $J_{4,3}$=$J_{4,5}$=9.2 Hz, 2H, H-4), 3.91 (t, $J_{8,9}$=6.6 Hz, 4H, CH$_2$-8), 1.73 (p, $J_{9,10}$=6.8 Hz, 4H, CH$_2$-9), 1.39-1.45 (m, 4H, CH$_2$-10), 1.25-1.34 (m, 56H, CH$_2$-11-CH$_2$-24), 0.88 (t, $J_{25,24}$=6.8 Hz, 6H, CH$_3$-25); $^{13}$C NMR (125 MHz, C$_5$D$_5$N) δ 166.9 (C-7), 163.6 (C-4'), 132.4 (C-2'), 124.2 (C-1') 114.9 (C-3'), 95.8 (C-1), 74.9 (C-3), 73.2 (C-2), 71.9 (C-4), 71.5 (C-5), 68.2 (C-8), 64.7 (C-6), 32.5, 30.4, 30.4, 30.34, 30.33, 30.28, 30.27, 30.23, 30.0, 29.97, 23.3 (C-11-C-24), 29.74 (C-9), 26.6 (C-10), 14.6 (C-25); IR (film): 3428, 2917, 2850, 1710, 1686, 1607, 1511, 1469, 1254, 1168, 1100, 1077, 1052, 1036, 1021, 769 cm$^{-1}$; HRMS (ESI) calcd. For [C$_{62}$H$_{102}$O$_{15}$+Na]$^+$: 1109.7111; obsd.: 1109.7139.

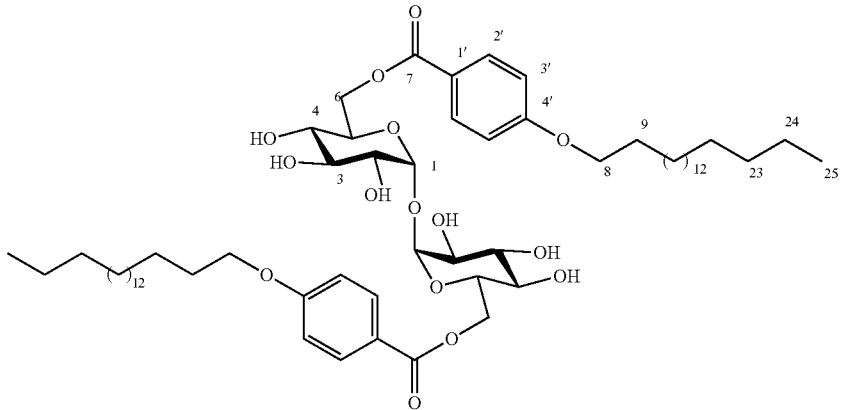

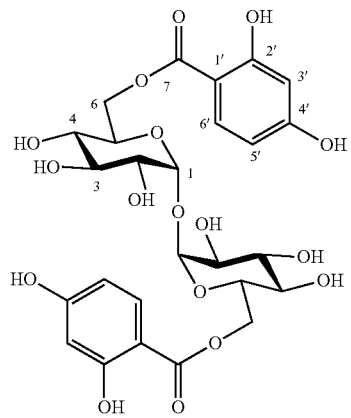

6,6'-Di-O-(4-octadecyloxybenzoyl)-α,α'-D-trehalose (9f). Benzyl protected trehalose 8f (122 mg, 0.075 mmol) and Pd(OH)$_2$/C (73 mg) were subjected to the conditions described in the general procedure for debenzylation. The resulting residue was purified by silica gel flash column chromatography (petroleum ether:EtOAc-EtOAc:MeOH, 1:1-4:1, v/v) to give the title compound as an amorphous off-white solid (42 mg, 0.038 mmol, 51%). R=0.31 (EtOAc)

6,6'-Di-O-(4-heptyloxybenzoyl)-α,α'-D-trehalose (9g). Benzyl protected trehalose 8g (87 mg, 0.066 mmol) and Pd(OH)$_2$/C (59 mg) were subjected to the conditions described in the general procedure for debenzylation. The resulting residue was purified by gradient silica gel flash column chromatography (petroleum ether:EtOAc-EtOAc:MeOH; 1:1-4:1, v/v) to give the title compound as an amorphous white solid (37 mg, 0.048 mmol, 73%). R$_f$=0.58 (EtOAc:MeOH, 4:1, v/v); [α]$^{20.0}_D$=+62.0 (c=0.1, pyridine); $^1$H NMR (500 MHz, C$_5$D$_5$N) δ 8.28 (d, $J_{2',3}$=8.8 Hz, 4H, H-2'), 6.95 (d, $J_{3',2}$=8.9 Hz, 4H, H-3'), 5.98 (d, $J_{1,2}$=3.8 Hz, 2H, H-1), 5.29 (ddd, $J_{5,4}$=10.0 Hz, $J_{5,6a}$=5.4 Hz, $J_{5,6b}$=1.7 Hz, 2H, H-5), 5.19 (dd, $J_{6b,6a}$=11.7 Hz, $J_{6b,5}$=2.0 Hz, 2H, H-6b), 5.05 (dd, $J_{6a,6b}$=11.8 Hz, $J_{6a,5}$=5.7 Hz, 2H, H-6a), 4.83 (t, $J_{3,2}$=$J_{3,4}$=9.3 Hz, 2H, H-3), 4.40 (dd, $J_{2,3}$=9.7 Hz, $J_{2,1}$=3.7 Hz, 2H, H-2), 4.29 (t, $J_{4,3}$=$J_{4,5}$=9.4 Hz, 2H, H-4), 3.89 (t, $J_{8,9}$=6.8 Hz, 4H, CH$_2$-8), 1.69 (p, $J_{9,8}$=$J_{9,10}$=8.0 Hz, 4H, CH$_2$-9), 1.36 (p, $J_{10,9}$=$J_{10,11}$=7.6 Hz, 4H, CH$_2$-10), 1.28-1.18 (m, 12H, CH$_2$-11-CH$_2$-13), 0.85 (t, $J_{14,13}$=6.9 Hz, 6H, CH$_3$-14); $^{13}$C NMR (125 MHz, C$_5$D$_5$N) δ 166.9 (C-7), 163.6 (C-4'), 132.4 (C-2'), 123.5 (C-1'), 114.8 (C-3'), 96.3 (C-1), 75.4 (C-3), 73.8 (C-2), 72.5 (C-4), 72.0 (C-5), 68.7 (C-8), 65.3 (C-6), 32.3, 29.5, 23.1 (C-11-C-13) 29.6 (C-9), 26.5 (C-10), 14.6 (C-14); IR (film): 3327, 2918, 2850, 1714, 1606, 1585, 1467, 1360, 1254, 1149, 1080, 1042, 985, 770 cm$^{-1}$; HRMS (ESI) calcd. for [C$_{40}$H$_{58}$O$_{15}$+NH$_4$]$^+$: 796.4119; obsd.: 796.4134.

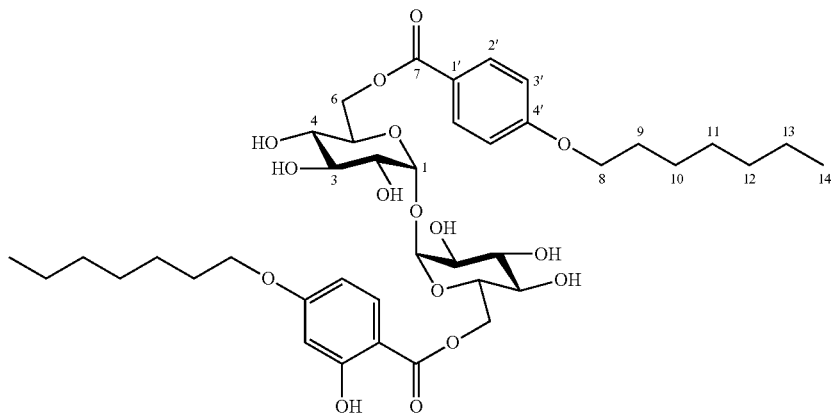

6,6'-Di-O-(4-heptyloxy-2-hydroxy-6-methylbenzoyl)-α,α'-D-trehalose (9h). Benzyl protected trehalose 8h (133 mg, 0.071 mmol) and Pd(OH)$_2$/C (80 mg) were subjected to the conditions described in the general procedure for debenzylation. The resulting residue was purified by silica gel flash column chromatography (petroleum ether:EtOAc-EtOAc: MeOH, 1:1-9:1, v/v) to give the title compound as a white solid (56 mg, 0.049 mmol, 69%). R$_f$=0.15 (EtOAc); $[\alpha]^{20.8}_D$=+39 (c=0.5, pyridine); $^1$H NMR (500 MHz, C$_5$D$_5$N) δ 12.25 (s, 2H, OH) 6.67 (d, J$_{3',5'}$=2.4 Hz, 2H, H-3'), 6.46 (d, J$_{5',3'}$=2.2 Hz, 2H, H-5), 5.93 (d, J$_{1,2}$=3.7 Hz, 2H, H-1), 5.24 (ddd, J$_{5,4}$=9.6 Hz, J$_{5,6a}$=5.2 Hz, J$_{5,6b}$=1.9 Hz, 2H, H-5), 5.16 (dd, J$_{6b,6a}$=11.8 Hz, J$_{6b,5}$=2.0 Hz, 2H, H-6b), 4.98 (dd, J$_{6a,6b}$=11.7 Hz, J$_{6a,5}$=5.5 Hz, 2H, H-6a), 4.81 (t, J$_{3,2}$=J$_{3,4}$=9.2 Hz, 2H, H-3), 4.33 (dd, J$_{2,3}$=9.6 Hz, J$_{2,1}$=3.6 Hz, 2H, H-2), 4.18 (t, J$_{4,3}$=J$_{4,5}$=9.5 Hz, 2H, H-4), 3.95 (t, J$_{8,9}$=6.5 Hz, 4H, CH$_2$-8), 2.76 (s, 6H, 6-Me), 1.74 (p, J$_{9,8}$=J$_{9,10}$=7.2 Hz, 4H, CH$_2$-9), 1.39-1.45 (m, 4H, CH$_2$-10), 1.24-1.34 (m, 56H, CH$_2$-11-CH$_2$-24), 0.88 (t, J$_{25,24}$=7.2 Hz, 6H, CH$_3$-25); $^{13}$C NMR (125 MHz, C$_5$D$_5$N) δ 172.3 (C-7), 166.0 (C-4'), 164.2 (C-2'), 144.0 (C-6'), 111.8 (C-5'), 106.8 (C-1'), 100.4 (C-3'), 96.4 (C-1), 75.1 (C-3), 73.7 (C-2), 72.7 (C-4), 71.6 (C-5), 68.6 (C-8), 66.4 (C-6), 32.5, 30.36, 30.35, 30.33, 30.28, 30.26, 30.23, 30.0, 23.3 (C-11-C-24), 29.7 (C-9), 26.6 (C-10), 24.9 (6-Me), 14.7 (C-25); IR (film): 3390, 2916, 2849, 1626, 1613, 1573, 1468, 1296, 1103, 985, 795, 695, 602 cm$^{-1}$; HRMS (ESI) calcd. For [C$_{64}$H$_{106}$O$_{17}$+H]$^+$: 1147.7503; obsd.: 1147.7497.

Brartemicin (9i). Benzyl protected trehalose 8i (86 mg, 0.056 mmol) and Pd(OH)$_2$/C (50 mg) were subjected to the conditions described in the general procedure for debenzylation. The resulting residue was purified by gradient silica gel flash column chromatography (EtOAc:MeOH:AcOH, 9:1:0.1-17:3:0.1, v/v/v) and lipophilic sephadex (CH$_2$Cl$_2$: MeOH, 1:1, v/v) to give 9i as an amorphous pale yellow solid (32 mg, 0.050 mmol, 89%). R$_f$=0.66 (MeOH:EtOAc, 1:4, v/v); $[\alpha]^{20}_D$=+67 (c=0.1, MeOH); $^1$H NMR (500 MHz, CD$_3$OD) δ 6.21 (s, 2H, H-5), 6.15 (s, 2H, H-3'), 5.13 (d, J$_{1,2}$=3.5 Hz, 2H, H-1), 4.58 (d, J$_{6a,6b}$=11.7 Hz, 2H, H-6a), 4.46 (dd, J$_{6a,6b}$=12.0 Hz, J$_{6b,5}$=4.8 Hz, 2H, H-6b), 4.18-4.22 (m, 2H, H-5), 3.84 (t, J$_{3,2}$=J$_{3,4}$=9.2 Hz, 2H, H-3), 3.50 (dd, J$_{2,3}$=9.6 Hz, J$_{2,1}$=3.6 Hz, 2H, H-2), 3.44 (t, J$_{4,3}$=J$_{4,5}$=9.3 Hz, 2H, H-4), 2.51 (s, CH$_3$, 6-Me); $^{13}$C NMR (125 MHz, CD$_3$OD) δ 172.8 (C-7), 166.3 (C-2'), 163.9 (C-4'), 144.9 (C-6'), 112.5 (C-5'), 105.6 (C-1'), 101.7 (C-3'), 95.6 (C-1), 74.5 (C-3), 73.1 (C-2), 72.2 (C-4), 71.3 (C-5), 65.4 (C-6), 24.9 (6-Me); IR (film): 3363, 2935, 1619, 1504, 1376, 1261, 1205, 1155, 1100, 1076, 1046, 994,798, 696 cm$^{-1}$; HRMS (ESI) calcd for [C$_2$H$_{34}$O$_{17}$+H]$^+$: 643.1869; obsd.: 643.1866.

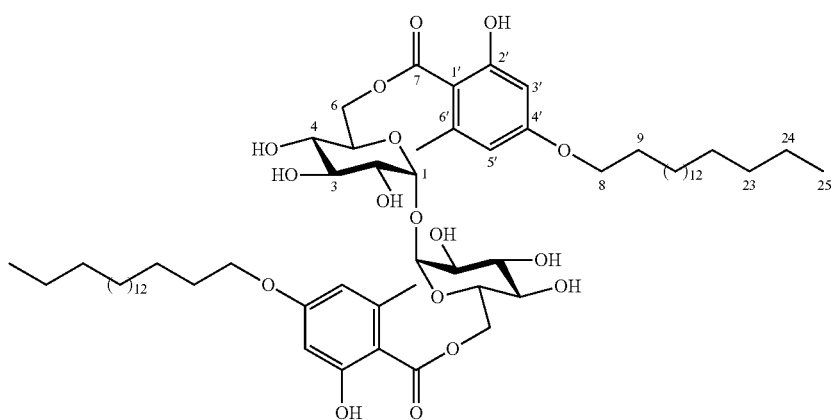

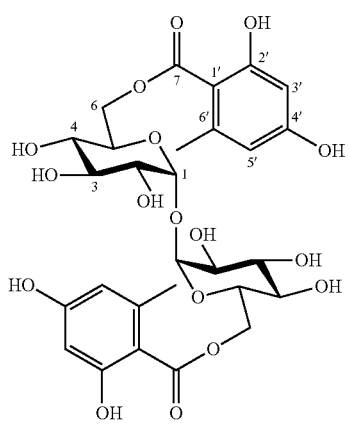

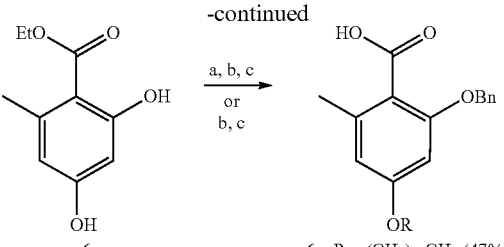

6a: R = (CH$_2$)$_{17}$CH$_3$ (47%)
6b: R = Bn (92%)

Using the above described techniques, a series of 4-O-alkyl, desmethyl and dehydroxy brartemicin derivatives with different lipid lengths were prepared. To vary the length of the 4-O-alkyl group, a series of 4-alkoxy-benzoic acid derivatives was prepared incorporating long (C$_{18}$), medium (C$_7$) and short (C$_4$ or C$_1$) alkyl chains as per Scheme 1 below.

Scheme 1

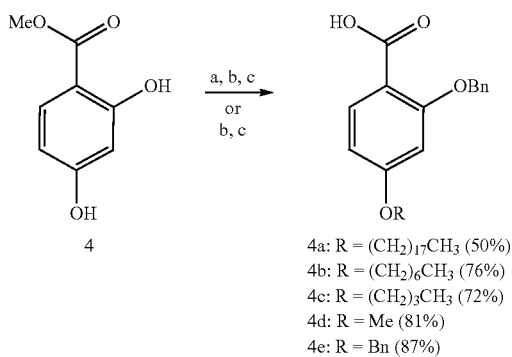

4a: R = (CH$_2$)$_{17}$CH$_3$ (50%)
4b: R = (CH$_2$)$_6$CH$_3$ (76%)
4c: R = (CH$_2$)$_3$CH$_3$ (72%)
4d: R = Me (81%)
4e: R = Bn (87%)

Scheme 1. Reagents and conditions a) CH$_3$(CH$_2$)$_{17}$Br/TBAI, CH$_3$(CH$_2$)$_6$I, CH$_3$(CH$_2$)$_3$I, or MeI, K$_2$CO$_3$, acetone, reflux; b) BnBr, TBAI, K$_2$CO$_3$, acetone, reflux; c) NaOH (5M), MeOH, reflux. The overall yield for each benzoate is reported in parentheses.

To this end, methyl 2,4-dihydroxybenzoate (4) was selectively alkylated at the 4-position, before benzyl protection and ester hydrolysis, to afford benzoic acid derivatives 4a-e in good to excellent yield over the three steps (50-87%). The effect of the substitution pattern on the aromatic ring was then considered via the alkylation of 4-hydroxybenzoic acid 5 with long and medium length alkyl groups, followed by hydrolysis to provide 2-deoxy-derivatives 5a and 5b, again in excellent yield (62-79%). Finally, alkylation of ethyl 2,4-dihydroxy-6-methylbenzoate (6), the core aromatic residue found in brartemicin, followed by benzylation of the 2-position and hydrolysis of the ester group gave the benzyl protected alkoxybenzoate 6a. In addition, 6 was dibenzylated and hydrolysed (→6b) en route to the total synthesis of brartemicin.

The final glycolipids were assembled via esterification of partially protected trehalose 7, prepared in three steps according to literature procedures (Khan et al. 2001), with the aforementioned benzoic acids. The esterification reactions were performed in the presence of 1-ethyl-3-(3-dimethylaminopropyl)carbodiimide (EDCI) and 4-(dimethylamino)pyridine (DMAP) and gave the desired benzyl-protected trehalose diesters 8a-i in good yields (Table 1). Global debenzylation using Pearlman's catalyst and H$_2$ then gave brartemicin (9i) and analogues 9a-h in good to excellent yields.

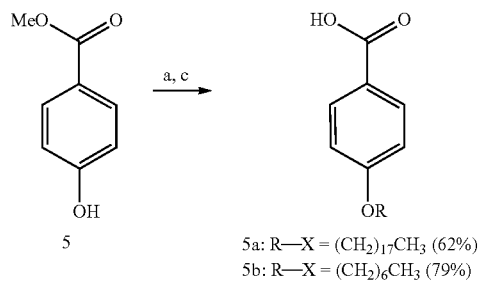

5a: R—X = (CH$_2$)$_{17}$CH$_3$ (62%)
5b: R—X = (CH$_2$)$_6$CH$_3$ (79%)

TABLE 1
Synthesis of brartemicin analogues
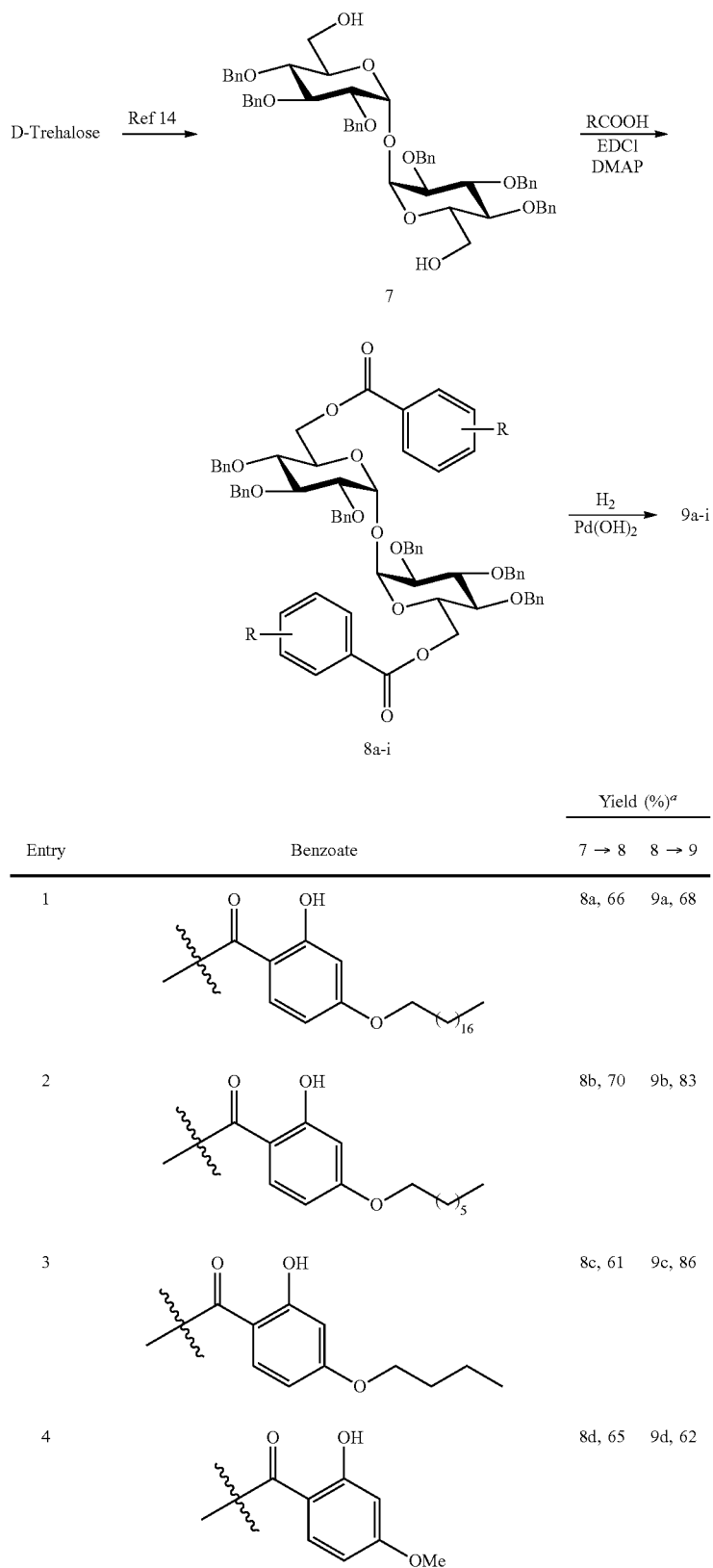
| Entry | Benzoate | Yield (%)[a] 7 → 8 | 8 → 9 |
|---|---|---|---|
| 1 | 2-hydroxy-4-(heptadecyloxy)benzoyl | 8a, 66 | 9a, 68 |
| 2 | 2-hydroxy-4-(hexyloxy)benzoyl | 8b, 70 | 9b, 83 |
| 3 | 2-hydroxy-4-butoxybenzoyl | 8c, 61 | 9c, 86 |
| 4 | 2-hydroxy-4-methoxybenzoyl | 8d, 65 | 9d, 62 |

TABLE 1-continued

| | | | |
|---|---|---|---|
| 5 | 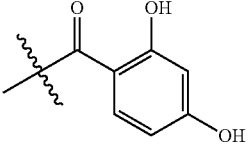 [SMILES: *C(=O)c1ccc(O)cc1O] | 8e, 58 | 9e, 92 |
| 6 | 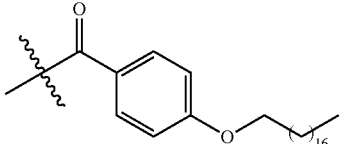 | 8f, 80 | 9f, 51 |
| 7 | 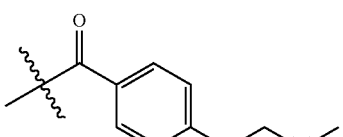 | 8g, 83 | 9g, 73 |
| 8 | 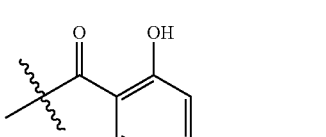 | 8h, 68 | 9h, 69 |
| 9 | 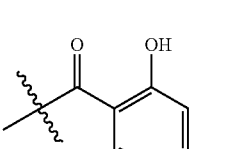 | 8i, 52 | 9i, 89 |

[a] All synthesised compounds were determined to be endotoxin free (≤0.1 EU/mL) by using the limulus amebocyte lysate (LAL) chromogenic assay.

Example 2: Binding and Activation of mMincle and hMincle

The synthesised brartemicin analogues prepared in Example 1 were first tested for their ability to bind to both human and murine Mincle in an enzyme-linked immunosorbent assay (ELISA) using soluble Mincle-Ig fusion-proteins (FIG. 1a).

Here, compounds lacking a lipophilic group, i.e. 4'-O-methyl-desmethyl-brartemicin (9d), desmethyl-brartemicin (9e), and brartemicin (9i), along with 4'-O-butyl-desmethyl-brartemicin (9c), which contains a short lipid, did not bind hMincle- or mMincle-Ig to any great extent. By comparison, the C18 containing analogues 9a, 9f, and 9h and analogues containing C7 lipid tails (9b and 9g) showed good binding for both the human and murine fusion-proteins.

Example 3: Activation of NFAT-Mincle Reporter Cells

To determine whether the Mincle binding observed in Example 1 correlated with cellular activation, nuclear factor of activated T cells (NFAT)-green fluorescent protein (GFP) reporter cells expressing mMincle or hMincle coupled to FcRγ were stimulated using plates coated with TDM, TDB, brartemicin (9i), or analogues 9a-9h.

Activation of the reporter cells was measured through the production of GFP, which was monitored by flow cytometry (FIGS. 1b and 3c).

Compounds of the invention incorporating C18 lipids (9a, 9f, and 9h) strongly activated both murine and human Mincle NFAT-GFP reporter cells in a dose-dependent manner, while the C7 containing analogues (9b and 9g) also activated mMincle and hMincle NFATGFP reporter cells but to a lesser extent than the C18 analogues.

The C4 analogue (9c) was able to activate mMincle and hMincle only at high ligand concentrations, while the non-lipidated analogues 9e and brartemicin (9i) did not significantly activate mMincle, with 9d showing only modest activation of hMincle at a high ligand concentration.

These findings illustrate that ligand binding does not exactly correlate to Mincle activation. The reason for the absence of a direct correlation between ligand binding and Mincle-activation is unclear, though it is possible that the functional receptor undergoes a conformational change upon ligand binding, which might alter the receptor activation state and receptor-ligand affinity.

These findings also demonstrate the subtle species-specific differences between hMincle and mMincle despite the sequence of mMincle and hMincle being highly conserved. Notwithstanding, at all concentrations tested, 9a was best able to activate hMincle.

Example 4: Activation of GM-CSF BMDMs

The capability of the brartemicin analogues prepared in Example 1 to induce APCs to produce inflammatory cytokines was examined to assess the interaction of the receptor with candidate ligands in a more physiological setting.

First, the ability of the compounds to activate GM-CSF BMDMs was determined by monitoring the secretion of the inflammatory cytokines TNF, IL-6, and IL-1β and the chemokine, MIP-2, in a ligand-coated plate assay (FIG. 2).

As illustrated, stimulation of BMDMs with the C18 brartemicin derivatives (9a, 9f and 9h) led to the significant production of all cytokines and MIP-2, as did TDB and TDM. The C7-derivatives (9b and 9g) gave modest production of MIP-2, IL-1β, TNF, and IL-6, while the C4 brartemicin derivative (9c) induced MIP-2 but not TNF, IL-6, and IL-1β.

The non-lipidated derivatives (9d and 9e) and brartemicin itself (9i) did not induce the production of any of the cytokines measured.

In the absence of Mincle, the production of MIP-2, IL-1β, TNF, and IL-6 in response to the synthetic ligands was abolished, suggesting that Mincle is the major receptor involved in mediating BMDM activation by lipophilic brartemicin derivatives.

Example 5: Th1/Th17 Inducing Adjuvant Activity In Vitro

To evaluate the potential of C18dMeBrar (9a) as a Th1/Th17 adjuvant, GM-CSF BMDMs and T-cells from OVA-specific OT-II TCR Tg mice were co-cultured on plates coated with TDM (0.01 nmol/well), TDB (0.01 nmol/well), or C18dMeBrar (9a, 0.01 nmol/well). The cells were stimulated with OVA (0, 0.1, and 1 μM), and after 48 hours, the supernatant was collected. Levels of the key Th1 cytokine IFN-γ, which is indicative of an enhanced host defence response, and the Th17 cytokine IL-17 were measured via ELISA (FIG. 3). The OVA-specific production of IL-17 was significantly augmented by 9a, albeit to a lesser extent than TDM and TDB. Antigen-specific secretion of IFN-γ however, was not enhanced by treatment with 9a.

Example 6: Th1-Stimulating Adjuvant Activity In Vivo

Compound 9a was then evaluated in vivo to confirm its capacity to induce a Th1 antigen-specific response using a delayed-type hypersensitivity immunisation protocol. To this end, four groups of C57BL/6 mice were immunised by subcutaneous injection with oil-in-water emulsions containing either OVA only, OVA+C18dMeBrar (9a), OVA+TDB, or no OVA. After seven days the mice were challenged with OVA (100 μg per footpad) and after a further seven days, the splenocytes were isolated and restimulated with OVA at three concentrations (10, 30, or 100 μg/mL). The immune response was measured by determining footpad swelling, production of IFN-γ and IL-17 (FIG. 7b), T cell proliferation (FIG. 4a), and antibody titres (FIG. 4c). While neither 9a nor TDB induced any footpad swelling or IL-17 production, immunisation of mice using C18dMeBrar (9a) gave rise to a polarised immune response with a distinct Th1 profile. A trend towards increased antigen specific IFN-γ production was observed for all concentrations of OVA when 9a was used as the adjuvant, with significantly enhanced cytokine production when re-stimulating with 100 μg/mL of antigen. In contrast, the Mincle agonist TDB did not lead to a significant increase in IFN-γ at any of the concentrations of OVA tested. A significantly larger number of splenocytes was also observed from mice that received C18dMeBrar (9a), as compared to those that received OVA alone (FIG. 7a). Moreover, at all concentrations of OVA re-stimulation, C18dMeBrar (9a) led to a significant increase in cell count compared to TDB. The limited efficacy of TDB in these in vivo assays was initially surprising, however studies addressing the adjuvanticity of TDB have largely focused on the TDB:DDA (CAF01) liposome system (Gram et al. 2009). Accordingly, the ability of C18dMeBrar (9a) to lead to an enhanced Th1 immune response was even more striking. This overall immune profile was also reflected in the antibody production by immunised mice. While C18dMeBrar (9a) and TDB elevated the production of IgG antibodies, the increase in antibody production was only significant for C18dMeBrar. When looking at the subclasses of antibodies produced, both Th1 associated subclasses IgG2b and IgG2c and Th2 associated IgG1 showed increases for C18dMeBrar and TDB. A high IgG2c:IgG1 ratio is commonly associated with Th1 responses and a lower ratio is associated with Th2 responses. The production of IgG2c in mice immunised with C18dMeBrar increased three-fold as compared to OVA alone, providing evidence that C18dMeBrar induces a Th1-biased immune response. In conclusion, C18dMeBrar (9a) is qualitatively similar to TDB with regard to its ability to enhance antibody production, however C18dMeBrar leads to a stronger Th1 immune response.

Example 7: Preparation of Further Compounds of the Invention

Preparation of Starting Materials

Methyl 2-(octadecyloxy)benzoate: To a solution of Methyl 2-hydroxybenzoate (500 mg, 3.29 mmol), K$_2$CO$_3$ (705 mg, 5.10 mmol), and TBAI (55 mg, 0.17 mmol) in acetone (25 mL) was added 1-bromooctadecane (1.55 g, 4.65 mmol) and the resulting suspension was stirred at reflux overnight. The following morning the reaction mixture was concentrated under reduced pressure and the remaining residue was purified by silica-gel column chromatography (1:0-9:1, Pet. Ether:EtOAc, v/v) to give the title compound as an off-white solid (383 mg, 0.95 mmol, 29%).

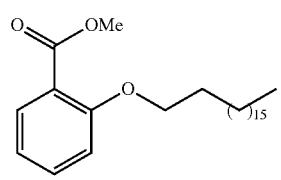

2-(octadecyloxy)benzoic acid: To a solution of Methyl 2-(octadecyloxy)benzoate (383 mg, 0.947 mmol) in MeOH (30 mL) was added NaOH (5 mL, 5 M) and the resulting mixture was refluxed overnight. The following day, the reaction mixture was diluted with water (20 mL), acidified to pH 1 with conc. HCl, and extracted with EtOAc. The organic phase was dried over MgSO$_4$, filtered, and concentrated under reduced pressure to give the title compound as an off-white amorphous solid (338, 0.865 mmol, 91%).

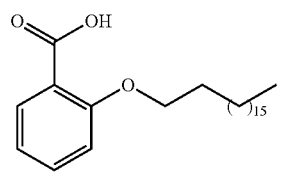

Ethyl 3-(octadecyloxy)benzoate: To a solution of Ethyl 3-hydroxybenzoate (500 mg, 3.01 mmol), TBAI (100 mg, 0.31 mmol), and K₂CO₃ (622 mg, 4.50 mmol) in acetone (25 mL) was added 1-bromooctadecane (1.50 g, 4.50 mmol) and the resulting suspension was refluxed overnight. The reaction mixture was concentrated in vacuo and the remaining residue was purified by silica-gel column chromatography (1:0-17:3, Pet. Ether:EtOAc, v/v) to give the title compound as an off-white solid (1.09 g, 2.60 mmol, 86%).

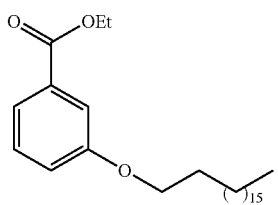

3-Octadecyloxybenzoic acid: To a solution of ethyl 3-(octadecyloxy)benzoate (590 mg, 1.41 mmol) in ethanol (25 mL) was added a solution of NaOH (5 M, 6 mL) and the resulting suspension was refluxed overnight. The reaction mixture was diluted with H₂O (50 mL), acidified to pH 1 with conc. HCl, and extracted with EtOAc (50 mL). The organic phase was dried with MgSO₄, filtered, and concentrated under reduced pressure to give the named compound as an off white solid (503 mg, 1.29 mmol, 91%).

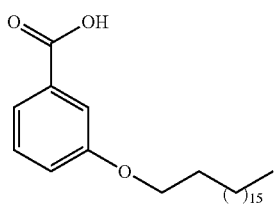

Methyl 3,5-bis(octadecyloxy)benzoate: To a solution of Methyl 3,4-dihydroxybenzoate (208 mg, 1.24 mmol) in acetone (20 mL) was added K₂CO₃ (362 mg, 2.62 mmol), 1-bromooctadecane (880 mg, 2.64 mmol), and TBAI (39 mg, 0.121 mmol) and the resulting suspension was refluxed overnight. The following day, further portions of 1-bromooctadecane (146 mg, 0.438 mmol), K₂CO₃ (100 mg, 0.724 mmol), and TBAI (40 mg, 0.124 mmol) were added and the reaction mixture was left to stir at reflux for a further 12 hours. The reaction mixture was concentrated in vacuo and the resulting residue was purified by silica-gel column chromatography (1:0-9:1, Pet. ether:EtOAc, v/v) to give the title compound as a white solid (413 mg, 0.614 mmol, 50%).

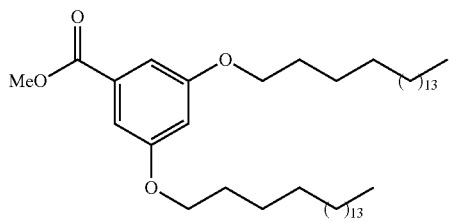

3,5-bis(octadecyloxy)benzoic acid: To a solution of methyl 3,5-bis(octadecyloxy)benzoate (402 mg, 0.60 mmol) in MeOH (20 mL) was added NaOH (5 mL, 5M) and the resulting suspension was refluxed overnight. The reaction mixture was diluted with water, acidified with conc. HCl (to pH 1), and extracted with EtOAc. The organic phase was dried over MgSO₄, filtered, and concentrated in vacuo to give the title compound as an off-white solid (220 mg, 0.335 mmol, 56%).

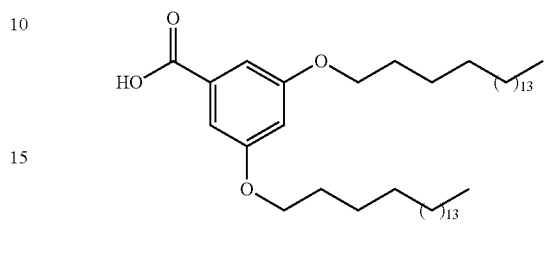

Methyl 3-(4-[hexadecyloxy]phenyl)propanoate: To a solution of methyl 3-(4-hydroxyphenyl)propanoate (300 mg, 1.66 mmol) in acetone (20 mL) was added K₂CO₃ (299 mg, 2.16 mmol), TBAI (54 mg, 0.166 mmol), and 1-bromohexadecane (0.66 mL, 2.16 mmol) and the resulting suspension was refluxed overnight. The following day, additional portions of 1-bromohexadecane (0.1 mL, 0.327 mmol) and TBAI (30 mg, 0.093 mmol) were added and mixture was stirred at reflux for an additional two hours. The reaction mixture was concentrated under reduced pressure and the resulting residue was purified by silica-gel column chromatography (1:0-19:1. Pet. Ether:EtOAc, v/v) to give the title compound as a white solid (457 mg, 1.129 mmol, 68%).

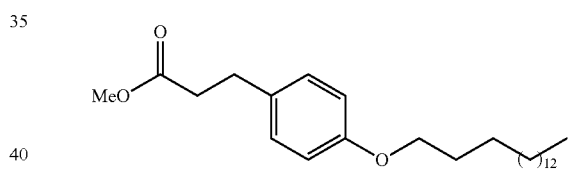

3-(4-[hexadecyloxy]phenyl)propanoic acid: To a solution of Methyl 3-(4-[hexadecyloxy]phenyl)propanoate (450 mg, 1.11 mmol) in MeOH (20 mL) was added NaOH (5.6 mL, 5 M) and the resulting suspension was refluxed overnight. The reaction mixture was diluted with H₂O (50 mL), acidified with conc. HCl (pH 1), extracted with EtOAc, dried over MgSO₄, filtered, and concentrated in vacuo to give the title compound as an off-white solid (403 mg, 1.03 mmol, 93%).

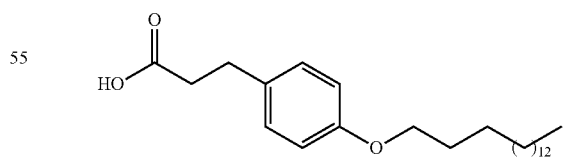

Methyl 4-hexadecyloxycinnamte: To a solution of Methyl 4-hydroxycinnamate (409 mg, 2.30 mmol) in acetone (15 mL) was added K₂CO₃ (472 mg, 3.42 mmol), 1-bromohexadecane (1.05 mL, 3.45 mmol), and TBAI (74 mg, 0.230 mmol) and the resulting solution was stirred at reflux overnight. The reaction mixture was concentrated in vacuo and purified via silica-gel column chromatography (1:0-4:1, Pet. Ether:EtOAc, v/v) to give the title compound as a white solid (817 mg, 2.03 mmol, 88%).

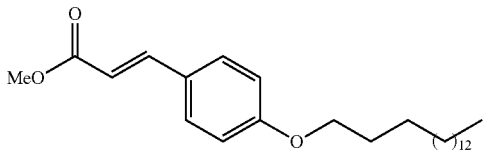

4-Hexadecyloxycinnamic acid: To a solution of Methyl 4-hexadecyloxycinnamte (379 mg, 0.941 mmol) in MeOH (20 mL) was added NaOH (5 mL, 5 M) and the resulting suspension was refluxed overnight. The reaction mixture was diluted with 1 M HCl (50 mL), extracted with EtOAc (50 mL), dried over MgSO$_4$, filtered, and concentrated in vacuo to give the title compound as an off-white solid (291 mg, 0.749 mmol, 80%).

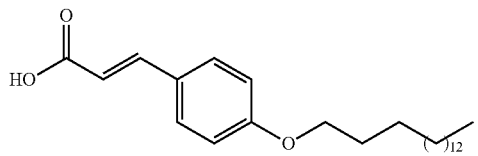

Octadecyltriphenylphosphoniumbromide: A solution of 1-bromooctadecane (5.00 g, 0.015 mol) and PPh$_3$ (3.93 g, 0.015 mmol) in toluene (20 mL) was heated to 120° C. for 24 hours. The reaction mixture was cooled to room temperature and precipitated by the addition of Et$_2$O (50 mL). The precipitate was repeatedly washed with Et$_2$O to give the title compound as a pale brown solid (5.10 g, 8.57 mmol, 57%).

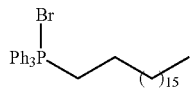

Methyl (Z)-4-(nonadec-1-en-1-yl)benzoate: To a solution of Octadecyltriphenylphosphoniumbromide (543 mg, 0.914 mmol) in freshly distilled THF (5 mL) cooled to 0° C. was added BuLi (0.46 mL, 2 M) dropwise. The reaction mixture was warmed to room temperature and left to stir for 1 hour. To the reaction mixture was added aldehyde methyl 4-formylbenzoate (150 mg, 0.914 mmol) dissolved in dry THF (2 mL) and the resulting solution was left to stir at room temperature for 12 hours. The following day, the reaction was quenched by the addition of acetone (5 mL) and concentrated under reduced pressure. The resulting residue was purified by silica-gel column chromatography (1:0-99:1, pet. ether:EtOAc, v/v) to give the title compound as a white solid (3:1 mixture, Z:E, 276 mg, 0.689 mmol, 76%).

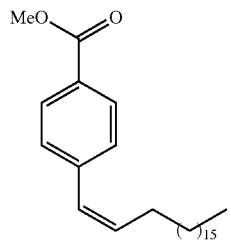

(Z)-4-(Nonadec-1-en-1-yl)benzoic acid: To a solution of benzoate methyl 4-(nonadec-1-en-1-yl)benzoate (273 mg, 0.682 mmol) in MeOH (40 mL) was added NaOH (5 M, 8 mL) and the resulting suspension was refluxed overnight. The reaction mixture was acidified (pH 1) with 1 M HCl, extracted with EtOAc (50 mL), dried over MgSO$_4$, and concentrated under reduced pressure to give the title compound as an amorphous white solid (241 mg, 0.623 mmol, 91%).

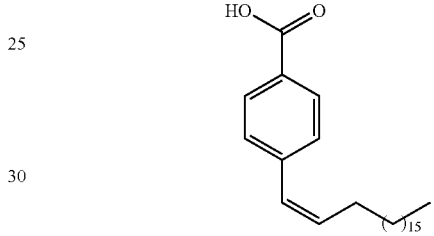

Octadecanal: To a solution of PCC (1.60 g, 7.42 mmol) in dry CH$_2$Cl$_2$ (20 mL) was added octadecanol (1.0 g, 3.70 mmol) and the resulting solution was left to stir at room temperature for 3 hours. The reaction mixture was filtered over silica-gel, concentrated under reduced pressure, and purified by silica-gel column chromatography (1:0-9:1, pet. ether:EtOAc, v/v) to give the title compound as a white solid (847 mg, 3.13 mmol, 85%).

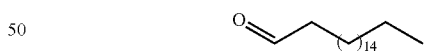

Ethyl 4-(octadecylamino)benzoate: Ethyl 4-aminobenzoate (200 mg, 1.21 mmol), octadecanal (650 mg, 2.42 mmol), and AcOH (0.21 mL, 3.63 mmol) were dissolved in THF (10 mL) and stirred at room temperature for 10 minutes. To the resulting solution was added NaBH(OAc)$_3$ (518 mg, 2.44 mmol) and the reaction was left to stir at room temperature overnight. The reaction mixture was concentrated in vacuo and the residue was purified by silica-gel column chromatography (1:0-9:1, pet. ether:EtOAc, v/v) to give the title compound as a white solid (469 mg, 1.12 mmol, 93%).

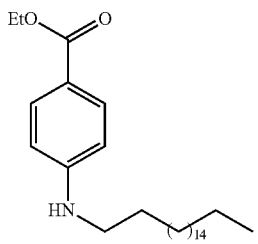

4-(octadecylamino)benzoic acid: To a solution of ethyl benzoate Ethyl 4-(octadecylamino)benzoate (460 mg, 1.10 mmol) in ethanol (20 mL) was added NaOH (5.5 mL, 5 M) and the resulting suspension was refluxed overnight. The reaction mixture was diluted with water (50 mL), acidified with conc. HCl (pH 1), extracted with EtOAc, dried over $MgSO_4$, filtered, and concentrated in vacuo to give the title compound as a beige solid (392 mg, 1.01 mmol, 92%).

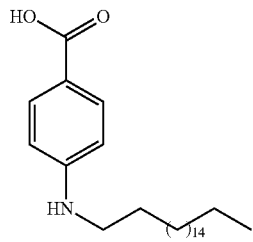

Methyl 4-(octadecylthio)benzoate: To a solution of Methyl 4-mercaptobenzoate (466 mg, 2.77 mmol) in acetone (20 mL) was added $K_2CO_3$ (613 mg, 4.44 mmol) and 1-bromooctadecane (1.48 g, 4.44 mmol), and TBAI (143 mg, 0.44 mmol) and the resulting solution was stirred at reflux overnight. The reaction mixture was concentrated under reduced pressure and purified by silica-gel column chromatography (1:0-3:2, pet. ether:EtOAc, v/v) to give the title compound as a white solid (460 mg, 1.09 mmol, 40%).

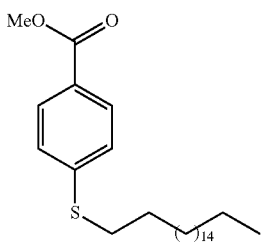

4-(Octadecylthio)benzoic acid: To a solution of methyl benzoate methyl 4-(octadecylthio)benzoate (446 mg, 1.06 mmol) in MeOH (20 mL) was added NaOH (5 mL, 5 M) and the resulting solution was refluxed overnight. The reaction mixture was diluted with 1 M HCl (50 mL), extracted with hot EtOAc, dried over $MgSO_4$, filtered, and concentrated under reduced pressure to give the title compound as a white amorphous solid (434 mg, 1.06, quant.).

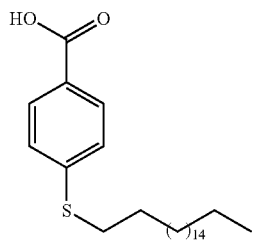

6,6'-Dideoxy-6,6'-diiodo-α,α'-trehalose. α,α'-Trehalose dihydrate (2.01 g, 5.31 mmol) was co-evaporated with DMF (40 mL), then dissolved in DMF (60 mL) and the volume reduced by one third. Triphenylphosphine (6.99 g, 26.6 mmol) and 12 (5.41 g, 21.3 mmol) were added and the resulting solution was stirred at 80° C. for 2 hours. The mixture was concentrated to one third of the volume, diluted with MeOH (80 mL), and the pH was adjusted to 8 with NaOMe. After stirring for 30 min, the mixture was neutralised with Dowex-H$^+$, filtered, and the resin washed with MeOH. The MeOH was removed in vacuo and the resultant sludge poured into vigorously stirred water (80 mL). The solid was removed by filtration over celite and the filtrate extracted with $CH_2Cl_2$ (3×130 mL). The aqueous layer was concentrated to give a yellow residue which was further purified by HP20 chromatography ($H_2O$ to $H_2O$:MeOH, 1:1, v/v) to give the title compound as a white solid (2.25 g, 4.00 mmol, 75%).

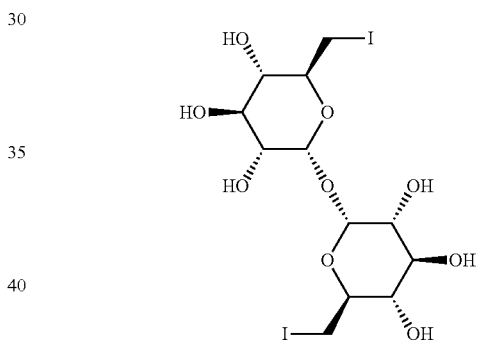

6,6'-Diazido-6,6'-dideoxy-α,α'-trehalose. To a stirred solution of 6,6'-Dideoxy-6,6'-diiodo-α,α'-trehalose (218 mg, 0.39 mmol) in DMF (5.0 mL) was added sodium azide (151 mg, 2.3 mmol). The mixture was stirred at 80° C. for 20 hours and then concentrated. The residue was purified by HP20 chromatography ($H_2O$ to $H_2O$:MeOH, 1:1, v/v) and lyophilised to give the title compound as a white solid (135 mg, 0.34 mmol, 89%).

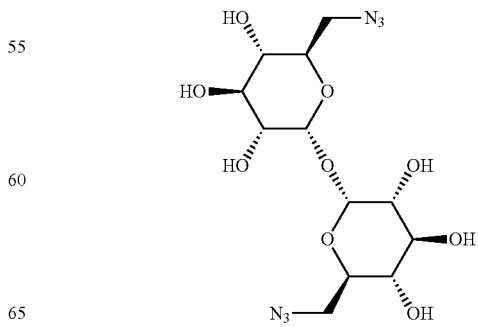

2,2',3,3',4,4'-Hexa-O-trimethylsilyl-α,α'-D-trehalose: α,α'-D-trehalose (5 g, 0.013 mol) was co-evaporated with DMF (2×25 mL) and dissolved in DMF (30 mL). To this solution was added BSA (22.4 mL, 0.13 mmol) and TBAF (1.25 mL, 1.3 mmol) and the resulting solution was stirred at room temperature for two hours. The reaction was quenched with isopropanol (2 mL) and diluted with MeOH (100 mL). $K_2CO_3$ (0.359 g) was added and the reaction was left to stir for a further 2 hours. The reaction mixture was concentrated in vacuo, partitioned between ether and brine, dried over $MgSO_4$, and concentrated under reduced pressure. The residue was purified by silica-gel column chromatography to give the title compound as white crystals (5.02 g, 6.47 mmol, 50%).

Preparation of Compounds of the Invention 2,2',3,3',4,4'-Hexa-O-benzyl-6,6'-di-O-(2-octadecyloxybenzoyl)-α,α'-D-trehalose (50): 2,2',3,3',4,4'-Hexa-O-benzyl-α,α'-D-trehalose (97 mg, 0.110 mmol) and 2-(octadecyloxy)benzoic acid (193 mg, 0.494 mmol) were co-evaporated with toluene (2×5 mL) and then dissolved in dry toluene (4 mL). To the resulting solution was added EDCI (137 mg, 0.714 mmol) and DMAP (13 mg, 0.110 mmol) and the mixture was stirred at 60° C. overnight. The following day, further portions of 2-(octadecyloxy)benzoic acid (60 mg, 0.154 mmol) and EDCI (60 mg, 0.313 mmol) were added and the resulting suspension was stirred for an additional 2 hours. The reaction mixture was diluted with EtOAc (50 mL), washed with $H_2O$ (50 mL) and brine (50 mL), dried over $MgSO_4$, filtered, and concentrated in vacuo. The remaining residue was purified by silica-gel column chromatography (1:0-5:1, pet. ether:EtOAc, v/v) to give the title compound as a clear oil (150 mg, 0.921 mmol, 84%). $R_f$=0.51 (4:1; pet. ether:EtOAc); $[α]^{21.0}_D$=+56 (c=0.1, $CH_2Cl_2$); $^1H$ NMR (500 MHz, $CDCl_3$) δ 7.72 (dd, $J_{6',5'}$=8.0 Hz, $J_{6',4'}$=1.6 Hz, 2H, H-6'), 7.41 (td, $J_{4',3'}$=$J_{4',5'}$=7.9 Hz, $J_{4',6'}$=1.8 Hz, 2H, H-4'), 7.37-7.20 (m, 30H, $CH_{arom}$), 6.91 (m, 2H, H-5', H-3'), 5.22 (d, $J_{1,2}$=3.6 Hz, 2H, H-1), 5.03 (d, $J_{a,b}$=11.0 Hz, 2H, $CH_a$ 3-O—Bn), 4.89 (d, $J_{a,b}$=10.8 Hz, 2H, $CH_b$ 3-O—Bn), 4.86 (d, $J_{a,b}$=10.4 Hz, 2H, $CH_a$ 4-O—Bn), 4.67 (s, 4H, $CH_2$ 2-O—Bn), 4.58 (d, $J_{a,b}$=10.5 Hz, 2H, $CH_b$ 4-O—Bn), 4.42 (dd, $J_{6a,6b}$=12.3 Hz, $J_{6a,5}$=3.4 Hz, 2H, H-6a), 4.33 (m, 2H, H-5), 4.27 (m, 2H, H-6b), 4.08 (t, $J_{3,4}$=$J_{2,3}$=9.4 Hz, 2H, H-3), 3.97 (m, 4H, $CH_2$-8'), 3.71 (t, $J_{3,4}$=14,5=9.5 Hz, 2H, H-4), 3.58 (dd, $J_{2,3}$=9.6 Hz, $J_{1,2}$=3.4 Hz, 2H, H-2), 1.78 (p, $J_{8',9'}$=7.4 Hz, 4H, $CH_2$-9'), 1.37 (m, 4H, $CH_2$-10'), 1.31-1.20 (m, 56H, $CH_2$-11'-$CH_2$-24'), 0.88 (t, $J_{23',24'}$=7.1 Hz, 6H, $CH_3$-25'); $^{13}C$ NMR (150 MHz, $CDCl_3$) δ 165.8 (C-7), 158.7 (C-2'), 138.7 ($C_i$, 3-O—Bn), 137.9, 137.8 ($C_i$, 2-O—Bn, 4-O—Bn), 133.4 (C-4'), 131.7 (C-6'), 128.44, 128.42, 128.37, 128.2, 127.90, 127.86, 127.7, 127.6, 127.4 ($CH_{arom}$), 120.0 (C-1'), 119.9, 113.0 (C-3', C-5), 94.0 (C-1), 81.7 (C-3), 79.4 (C-2), 77.7 (C-4), 75.7 ($CH_2$, 3-O—Bn), 75.3 ($CH_2$, 4-O—Bn), 72.8 ($CH_2$, 2-O—Bn), 69.3 (C-5), 68.9 ($CH_2$-8'), 63.0 (C-6), 31.9, 29.70, 29.68, 29.61, 29.38, 29.35, 29.2, 22.7 ($CH_2$-9', $CH_2$-11'-$CH_2$-24'), 25.8 ($CH_2$-10'), 14.1 ($CH_3$-25'); IR (film): 2922, 2852, 1735, 1453, 1298, 1244, 1071, 998, 753 $cm^{-1}$; HRMS calcd. for $[C_{104}H_{138}O_{15}+NH_4]^+$: 1645.0374; obsd.: 1645.0375.

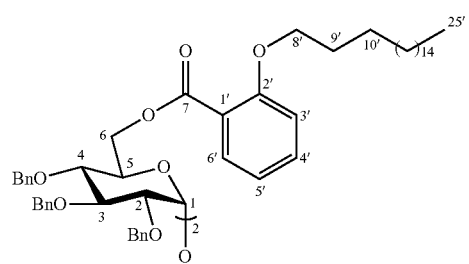

50

6,6'-Di-O-(2-octadecyloxybenzoyl)-α,α'-D-trehalose (43a): To a solution of diester 50 (146 mg, 0.090 mmol) in MeOH:$CH_2Cl_2$ (4 mL, 1:1, v/v) was added $Pd(OH)_2$/C (88 mg). $H_2$-gas was bubbled through the reaction mixture overnight. The following day, the reaction mixture was diluted in pyridine, filtered over celite, and concentrated in vacuo. The resulting residue was purified by silica-gel column chromatography (1:1-9:1, pet. ether:EtOAc-EtOAc:MeOH, v/v) to give the title compound as an off-white amorphous solid (56 mg, 0.051 mmol, 57%). $R_f$=0.63 (9:1, EtOAc:MeOH, v/v); $[α]^{20.3}_D$=+80 (c=0.1, pyridine); $^1H$ NMR (600 MHz, $C_5D_5N$) δ 8.10 (dd, $J_{5',6'}$=7.6 Hz, $J_{6',4}$=1.8 Hz, 2H, H-6'), 7.42 (m, 1H, H-4'), 7.27 (bs, 2H, OH), 7.01 (m, 6H, OH, H-5'), 6.86 (t, $J_{3',4'}$=7.6 Hz, 2H, H-3'), 5.88 (d, $J_{1,2}$=3.7 Hz, 2H, H-1), 5.21 (ddd, $J_{5,4}$=10.0 Hz, $J_{5,6b}$=4.7 Hz, $J_{5,6a}$=1.8 Hz, 2H, H-5), 5.16 (dd, $J_{6a,6b}$=11.9 Hz, $J_{5,6a}$=2.1 Hz, 2H, H-6a), 5.08 (dd, $J_{6a,6b}$=11.8 Hz, $J_{5,6b}$=5.0 Hz, 2H, H-6b), 4.77 (t, $J_{2,3}$=13,4=9.1 Hz, 2H, H-3), 4.28 (m, 4H, H-2, H-4), 3.97 (m, 4H, $CH_2$-8'), 1.83 (m, 4H, $CH_2$-9'), 1.48 (m, 4H, $CH_2$-10'), 1.30-1.20 (m, 56H, $CH_2$-11'-$CH_2$-24'), 0.85 (t, $J_{24',25'}$=7.1 Hz, 6H, $CH_3$-25'); $^{13}C$ NMR ($C_5D_5N$) δ 166.7 (C-7), 159.5 (C-2'), 133.8 (C-4'), 132.3 (C-6'), 122.0 (C-1'), 120.6 (C-3'), 114.2 (C-5), 96.4 (C-1), 75.4 (C-3), 73.8, 72.3 (C-2, C-4), 72.0 (C-5), 69.6 ($CH_2$-8'), 65.2 (C-6), 32.5, 30.4, 30.38, 30.36, 30.33, 30.30, 30.1, 30.0, 29.9, 23.3 ($CH_2$-9', $CH_2$-11'-$CH_2$-24'), 26.6 (C-10'), 14.7 ($CH_3$-25'); IR (3253, 2918, 2850, 1734, 1449, 1238, 1081, 992, 755 $cm^{-1}$; HRMS (ESI) calcd. for $[C_{62}H_{102}O_{15}+NH_4]^+$: 1104.7562; obsd.: 1104.7533.

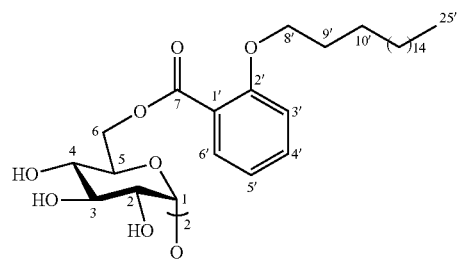

43a 2, 2',3,3',4,4'-Hexa-O-benzyl-6,6'-di-O-(3-octadecyloxybenzoyl)-α,α'-D-trehalose (51): 2,2',3,3',4,4'-Hexa-O-benzyl-α,α'-D-trehalose (107 mg, 0.121 mmol) and 3-octadecyloxybenzoic acid (212 mg, 0.543 mmol) were co-evaporated with toluene (2×5 mL) and then dissolved in dry toluene (7 mL). To the resulting solution was added EDCI (151 mg, 0.787 mmol) and DMAP (15 mg, 0.121 mmol) and the mixture was stirred at 55° C. overnight. The following day, further portions of 3-octadecyloxybenzoic acid (22 mg, 0.056 mmol) and EDCI (37 mg, 0.193 mmol) were added and the resulting suspension was stirred for an additional 2 hours. The reaction mixture was diluted with EtOAc (50 mL), washed with H$_2$O (50 mL) and brine (50 mL), dried over MgSO$_4$, filtered, and concentrated in vacuo. The remaining residue was purified by silica-gel column chromatography (1:0-22:3, pet. ether:EtOAc, v/v) to give the title compound as a clear oil (174 mg, 0.107 mmol, 88%). R$_f$=0.40 (9:1; pet. ether:EtOAc, v/v); $^1$H NMR (500 MHz, CDCl$_3$) δ 7.52 (d, J$_{5',6'}$=7.7 Hz, 2H, H-6'), 7.48 (s, 2H, H-2'), 7.38-7.23 (m, 32H, H-3', CH$_{arom}$), 7.06 (dd, J$_{4'-5'}$=7.9 Hz, J$_{4',6'}$=2.3 Hz, 2H, H-4'), 5.22 (d, J$_{1,2}$=3.6 Hz, 2H, H-1), 5.02 (d, J$_{a,b}$=10.5 Hz, 2H, CH$_a$ 3-O—Bn), 4.90 (d, J$_{a,b}$=10.6 Hz, 2H, CH$_b$ 3-O—Bn), 4.89 (d, J$_{a,b}$=10.7 Hz, 2H, CH$_a$ 4-O—Bn), 4.73 (d, J$_{a,b}$=11.9 Hz, CH$_a$ 2-O—Bn), 4.69 (d, J$_{a,b}$=11.7 Hz, 2H, CH$_b$ 2-O—Bn), 4.58 (d, J$_{a,b}$=10.7 Hz, 2H, CH$_b$ 4-O—Bn), 4.34-4.24 (m, 6H, H-5, H-6), 4.11 (t, J$_{3,4}$=14, 5=9.7 Hz, 2H, H-3), 3.94 (t, J$_{8',9'}$=6.3 Hz, 4H, CH$_2$-8'), 3.66 (t, J$_{3,4}$=14,5=9.4 Hz, 2H, H-4), 3.61 (dd, J$_{2,3}$=9.7 Hz, J$_{1,2}$=3.5 Hz, 2H, H-2), 1.77 (m, 4H, CH$_2$-9'), 1.43 (m, 4H, CH$_2$-10'), 1.36-1.02 (m, 56H, CH$_2$-11'-CH$_2$-24'), 0.88 (t, J$_{24',25'}$=7.0 Hz, 6H, CH$_3$-25'); $^{13}$C NMR (150 MHz, CDCl$_3$) δ 166.3 (C-7), 159.3 (C-3'), 138.7 (C$_i$, 3-O—Bn), 138.0, 137.9 (C$_i$, 2-O—Bn, 4-O—Bn), 131.2 (C-1'), 129.5, 128.6, 128.3, 128.1, 127.5 (CH$_{arom}$, C-5'), 121.9, 115.1 (C-2', C-6'), 120.0 (C-4'), 94.1 (C-1), 81.9 (C-3), 79.7 (C-2), 77.8 (C-4), 76.0 (CH$_2$, 3-O-n), 75.5 (CH$_2$, 4-O-n), 73.2 (CH$_2$, 2-O—Bn), 69.5 (C-5), 68.4 (CH$_2$-8'), 63.2 (C-6), 32.1, 29.9, 29.82, 29.78, 29.74, 29.6, 29.5, 29.3, 22.9 (CH$_2$-9', CH$_2$-11-CH$_2$—CH$_2$-24'), 26.2 (CH$_2$-10'), 14.3 (CH$_3$-25'); IR (film): 2918, 2851, 1723, 1454, 1275, 1097, 1071, 998, 754, 697 cm$^{-1}$; HRMS (ESI) calcd. For [C$_{104}$H$_{138}$O$_{15}$+NH$_4$]$^+$: 1645.0374; obsd.: 1645.0399.

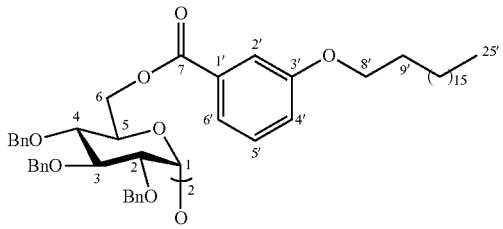

51

6,6'-Di-O-(3-octadecyloxybenzoyl)-α,α'-D-trehalose (43b): To a solution of diester 51 (110 mg, 0.067 mmol) in MeOH:CH$_2$Cl$_2$ (10 mL, 1:1, v/v) was added Pd(OH)$_2$/C (74 mg). H$_2$-gas was bubbled through the reaction mixture overnight. The following day, the reaction mixture was diluted in pyridine and filtered over celite and concentrated in vacuo. The resulting residue was purified by silica-gel column chromatography (1:1-9:1, pet. ether:EtOAc-EtOAc:MeOH, v/v) to give the title compound as an off-white amorphous solid (49 mg, 0.045 mmol, 67%). R$_f$=0.83 (4:1, EtOAc:MeOH, v/v); [α]$^{20}$$_D$=+80 (c=0.1, pyridine); $^1$H NMR (500 MHz, C$_5$D$_5$N) δ 7.93 (m, 2H, H-6', H-2'), 7.47 (d, J=5.6 Hz, 2H, OH), 7.30 (t, J$_{4',5'}$=J$_{5',6'}$=7.8 Hz, 2H, H-5'), 7.20 (dd, J$_{2',4'}$=2.6 Hz, 12',6'=0.9 Hz, 2H, H-4'), 7.15 (m, 2H, OH), 5.98 (d, J$_{1,2}$=3.7 Hz, 2H, H-1), 5.29 (ddd, J$_{4,5}$=10.1 Hz, J$_{5,6b}$=5.6 Hz, J$_{5,6a}$=1.7 Hz, 2H, H-5), 5.24 (dd, J$_{6a,6b}$=11.7 Hz, J$_{6a,5}$=1.9 Hz, 2H, H-6a), 5.05 (dd, J$_{6b,6a}$=11.8 Hz, J$_{6b,5}$=5.9 Hz, 2H, H-6b), 4.81 (t, J$_{2,3}$=13,4=9.41 Hz, 2H, H-3), 4.36 (m, 2H, H-2), 4.25 (td, J$_{4,5}$=9.8 Hz, J$_{4,3}$=5.1 Hz, 2H, H-4), 3.94 (t, 4H, CH$_2$-8'), 1.73 (p, J$_{8',9'}$=J$_{9',10'}$=6.7 Hz, 4H, CH$_2$-9'), 1.43 (m, 4H, CH$_2$-10'), 1.34-1.23 (m, 56H, CH$_2$-11'-CH$_2$-24'), 0.88 (t, J$_{24',25'}$=7.1 Hz, 6H, CH$_3$-25'); $^{13}$C NMR (150 MHz, C$_5$D$_5$N) δ 166.4 (C-7), 159.4 (C-3'), 132.2 (C-1'), 129.6 (C-5'), 121.9, 114.9 (C-6', C-2'), 119.9 (C-4'), 95.7 (C-1), 74.8 (C-3), 73.2 (C-2), 72.0 (C-4), 71.4 (C-5), 68.0 (CH$_2$-8'), 65.3 (C-6), 31.9, 29.8, 29.70, 29.67, 29.46, 29.39, 29.3, 29.1, 22.7 (CH$_2$-9', CH$_2$-11'-CH$_2$-24'), 26.1 (CH$_2$-10'), 14.1 (CH$_3$-25'); IR (film): 3331, 2916, 2849, 1696, 1490, 1279, 942, 754 cm$^{-1}$; HRMS (ESI) calcd. For [C$_{62}$H$_{102}$O$_{15}$+NH$_4$]$^+$: 1104.7557; obsd.: 1104.7555

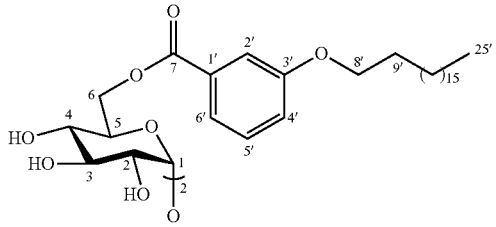

43b 2,2',3,3',4,4'-Hexa-O-benzyl-6,6'-di-O-(3,5-bis(octadecyloxy)benzoate)-α,α'-D-trehalose (55): 2,2',3,3',4,4'-Hexa-O-benzyl-α,α'-D-trehalose (97 mg, 0.110 mmol) and 3,5-bis(octadecyloxy)benzoic acid (472 mg, 0.716 mmol) were co-evaporated with toluene (2×5 mL) and then dissolved in dry toluene (3 mL). To the resulting solution was added EDCI (194 mg, 1.012 mmol) and DMAP (24 mg, 0.196 mmol) and the mixture was stirred at 55° C. overnight. The following day, the reaction mixture was diluted with EtOAc (50 mL), washed with H$_2$O (50 mL) and brine (50 mL), dried over MgSO$_4$, filtered, and concentrated in vacuo. The resulting residue was purified by silica-gel column chromatography (1:0-22:3, pet. ether:EtOAc, v/v) to give the title compound as a clear oil (146 mg, 0.067 mmol, 61%). R$_f$=0.69 (4:1, pet. Ether:EtOAc, v/v); [α]$^{24.7}$$_D$=+58 (c=0.1, CH$_2$Cl$_2$); $^1$H NMR (500 MHz, CDCl$_3$) δ 7.39-7.26 (m, 30H, CH$_{arom}$), 7.09 (d, J$_{2',4'}$=2.3 Hz, 4H, H-2'), 6.61 (t, J$_{2',4'}$=2.3 Hz, 2H, H-4'), 5.23 (d, J$_{1,2}$=3.6 Hz, 2H, H-1), 5.03 (d, J$_{a,b}$=10.8 Hz, 2H, CH$_a$ 3-O—Bn), 4.90 (d, J$_{a,b}$=10.7 Hz, 2H, CH$_b$ 3-O—Bn), 4.89 (d, J$_{a,b}$=10.6 Hz, 2H, CH$_a$ 4-O—Bn), 4.74 (d, J$_{a,b}$=11.9 Hz, 2H, CH$_a$ 2-O—Bn), 4.70 (d, J$_{a,b}$=11.9 Hz, 2H, CH$_b$ 2-O—Bn), 4.58 (d, J$_{a,b}$=10.6 Hz, 2H, CH$_b$ 4-O—Bn), 4.30 (m, 6H, H-5, H-6), 4.10 (t, J$_{2,3}$=J$_{3,4}$=9.4 Hz, 2H, H-3), 3.92 (t, J$_{6',7'}$=6.6 Hz, 4H, CH$_2$-6'), 3.65 (t, J$_{3,4}$=14, 5=9.3 Hz, 2H, H-4), 3.62 (dd, J$_{2,3}$=9.6 Hz, J$_{1,2}$=3.6 Hz, 2H, H-2), 1.76 (p, J$_{6',7'}$=6.7 Hz, 8H, CH$_2$-7'), 1.43 (m, 8H, CH$_2$-8'), 1.37-1.23 (m, 112H, CH$_2$-9'-CH$_2$-22'), 0.89 (t, J$_{22',23'}$=7.1 Hz, 12H, CH$_3$-23'); $^{13}$C NMR (125 MHz, CDCl$_3$) δ 166.3 (C-7), 160.3 (C-3'), 138.7 (C$_i$, 3-O—Bn), 138.0 (C$_i$ 4-O-n), 138.0 (C$_i$ 2-O-n), 131.7 (C-1'), 128.6, 129.3, 128.2, 128.1, 127.9, 127.8, 127.6 (CH$_{arom}$), 108.0 (C-2'), 106.3 (C-4'), 94.1 (C-1), 81.9 (C-3), 79.7 (C-2), 77.9 (C-4), 76.0 (CH$_2$, 3-O—Bn), 75.5 (CH$_2$, 4-O—Bn), 73.2 (CH$_2$, 2-O—Bn), 69.5 (C-5), 68.5 (CH$_2$-6'), 63.3 (C-6), 32.1, 29.9, 29.82, 29.80, 29.75, 29.6, 29.5, 29.3, 22.9 (CH$_2$-7', CH$_2$-9'-CH$_2$-22'), 26.2 (CH$_2$-8'), 14.3 (CH$_3$-23'); IR (film): 2921, 2851, 1724, 1595, 1453, 1163, 1069, 998, 732 cm$^{-1}$; MALDI-TOF/TOF MS calcd. for [C$_{140}$H$_{210}$O$_{17}$+Na]$^+$: 2186.5460; obsd.: 2186.5471.

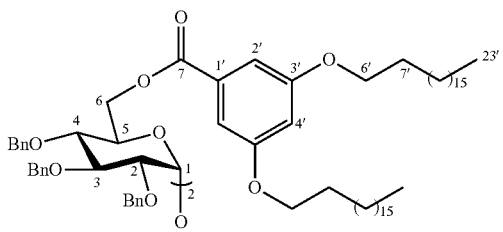

55

6,6'-di-O-(3,5-bis(octadecyloxy)benzoate)-α,α'-D-trehalose (43c): To a solution of 55 (154 mg, 0.071 mmol) in CH$_2$Cl$_2$:MeOH (1:1, 5 mL) was added Pd(OH)$_2$/C (87 mg) and the resulting suspension was bubbled with H$_2$ overnight. The following day, the reaction mixture was diluted with pyridine (50 mL), filtered over celite, and concentrated under reduced pressure. The residue was purified by silica-gel column chromatography (1:0-9:1, EtOAc:MeOH, v/v) to give the title compound as a white solid (62 mg, 0.038 mmol, 54%). R$_f$=0.60 (4:1, EtOAc:MeOH, v/v); [α]$^{21.4}_D$=+60 (c=0.1, pyridine); $^1$H NMR (600 MHz, C$_5$D$_5$N) δ 7.67 (d, J$_{2',4'}$=2.3 Hz, 4H, H-2'), 7.46 (d, J=5.4 Hz, 2H, OH), 7.16-7.10 (m, 4H, OH), 7.0 (t, J$_{2',4'=2.3}$ Hz, 2H, H-4'), 6.03 (d, J$_{1,2}$=3.7 Hz, 2H, H-1), 5.31 (m, 4H, H-5, H-6a), 5.03 (dd, J$_{6a,6b}$=12.1 Hz, J$_{5,6b}$=6.9 Hz, 2H, H-6b), 4.80 (t, J$_{3,4}$=J$_{2,3}$=9.3 Hz, 2H, H-3), 4.35 (m, 2H, H-2), 4.21 (m, 2H, H-4), 4.01 (m, 4H, CH$_2$-6'), 1.78 (p, J$_{6',7'}$=J$_{7',8'}$=6.6 Hz, 4H, CH$_2$-7'), 1.47 (m, 4H, CH$_2$-8'), 1.36-1.24 (m, 4H, 112H, CH$_2$-9'-CH$_2$-22'), 0.90 (t, J$_{22',23'}$=7.0 Hz, 12H, CH$_3$-23'); $^{13}$C NMR (150 MHz, C$_5$D$_5$N) δ 168.0 (C-7), 162.1 (C-3'), 134.1 (C-1'), 109.4 (C-2'), 108.3 (C-3'), 97.0 (C-1), 76.3 (C-3), 74.8 (C-2), 73.7 (C-4), 72.9 (C-5), 69.7 (CH$_2$-6'), 67.1 (C-6), 33.4, 31.3, 31.2, 31.0, 30.9, 30.8, 24.2 (CH$_2$-7', CH$_2$-9'-CH$_2$-22'), 27.7 (C-8'), 15.6 (CH$_3$-23'); IR (film): 3340, 2916, 2849, 1718, 1595, 1466, 1160, 987, 764 cm$^{-1}$; HRMS (ESI) calcd. For [C$_{98}$H$_{174}$O$_{17}$+NH$_4$]$^+$: 1641.3089; obsd.: 1641.3112.

43c

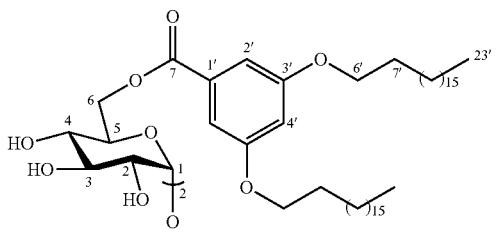

2,2',3,3',4,4'-Hexa-O-benzyl-6,6'-di-O-(3-[4-(hexadecyloxy)phenyl]propanoate)-α,α'-D-trehalose (59): 2,2',3,3',4,4'-Hexa-O-benzyl-α,α'-D-trehalose (130 mg, 0.147 mmol) and 3-(4-[hexadecyloxy]phenyl)propanoic acid (258 mg, 0.661 mmol) was co-evaporated with toluene (2×5 mL) and then re-dissolved in dry toluene (7 mL). To the resulting solution was added EDCI (187 mg, 0.975 mmol) and DMAP (18 mg, 0.147 mmol) and the mixture was stirred at 60° C. overnight. The reaction mixture was diluted with EtOAc (50 mL), washed with water and brine, dried over MgSO$_4$, filtered, and concentrated under reduced pressure. The resulting residue was purified by silica-gel column chromatography (1:0-9:1, pet. ether:EtOAc, v/v) and lipophilic size exclusion (1:1, CH$_2$Cl$_2$:MeOH, v/v) to give the title compound as a clear oil (102 mg, 0.065 mmol, 44%). R$_f$=0.38 (4:1, pet. ether:EtOAc, v/v); [α]$^{21}_D$=+56 (c=1.0, CH$_2$Cl$_2$); $^1$H NMR (500 MHz, CDCl$_3$) δ 7.36-7.20 (m, 30H, CH$_{arom}$), 7.03 (d, J$_{2'',3''}$=8.5 Hz, 4H, H-2''), 6.75 (d, J$_{2'',3}$=8.5 Hz, 4H, H-3''), 5.15 (d, J$_{1,2}$=3.6 Hz, 2H, H-1), 4.99 (d, J$_{a,b}$=10.8 Hz, 2H, CH$_2$Ph, CH$_a$ 3-O—Bn), 4.85 (d, J$_{a,b}$=10.9 Hz, 2H, CH$_2$Ph, CH$_b$ 3-O—Bn), 4.78 (d, J$_{a,b}$=10.7 Hz, 2H, CH$_2$Ph, CH$_a$ 4-O—Bn), 4.71 (d, J$_{a,b}$=11.9 Hz, 2H, CH$_2$Ph, CH$_a$ 2-O—Bn), 4.66 (d, J$_{a,b}$=12.0 Hz, 2H, CH$_2$Ph, CH$_b$ 2-O—Bn), 4.39 (d, J$_{a,b}$=10.6 Hz, 2H, CH$_2$Ph, CH$_b$ 4-O—Bn), 4.20 (m, 2H, H-5), 4.14 (dd, J$_{6a,6b}$=12.3 Hz, J$_{5,6a}$=3.6 Hz, 2H, H-6a), 4.02 (m, 4H, H-6b, H-3), 3.83 (t, J$_{5'',6''}$=6.6 Hz, 4H, CH$_2$-5''), 3.54 (dd, J$_{2,3}$=9.6 Hz, J1,2=3.5 Hz, 2H, H-2), 3.47 (t, J$_{3,4}$=14,5=9.6 Hz, 2H, H-4), 2.82 (m, 4H, CH$_2$-1'), 2.53 (m, 4H, CH$_2$-2'), 1.71 (m, 4H, CH$_2$-6''), 1.40 (m, 4H, CH$_2$-7''), 1.35-1.24 (m, 48H, CH$_2$-8''-CH$_2$-19''), 0.88 (t, J$_{19'',20''}$=7.2 Hz, 6H, CH$_3$-20''); $^{13}$C NMR (125 MHz, CDCl$_3$) δ 172.7 (C-3'), 157.7 (C-4''), 138.7 (C$_i$, 3-O—Bn), 138.0 (C$_i$, 4-O—Bn), 137.9 (C$_i$, 2-O—Bn), 132.2 (C-1''), 129.2 (C-2''), 128.64, 128.60, 128.58, 128.3, 128.1, 128.0, 127.8, 127.6 (CH$_{arom}$), 114.6 (C-3''), 94.3 (C-1), 81.7 (C-3), 79.4 (C-2), 77.5 (C-4), 75.8 (CH$_2$,3-O—Bn), 75.3 (CH$_2$, 4-O—Bn), 73.1 (CH$_2$, 2-O—Bn), 69.3 (C-5), 68.1 (CH$_2$-5''), 62.8 (C-6), 36.0 (CH$_2$-2'), 30.0, 29.9, 29.84, 29.83, 29.82, 29.77, 29.75, 29.6, 29.5, 29.46, 22.9 (CH$_2$-1', CH$_2$-6'', CH$_2$-8''-CH$_2$-19'') 26.2 (CH$_2$-7''), 14.3 (CH$_3$-20''); IR (film): 2923, 2853, 1735, 1512, 1245, 1106, 1096, 1071, 733, 697 cm$^{-1}$; HRMS (ESI) calcd. For [C$_{106}$H$_{142}$O$_{15}$+NH$_4$]$^+$: 1645.0380; obsd.: 1645.0407.

59

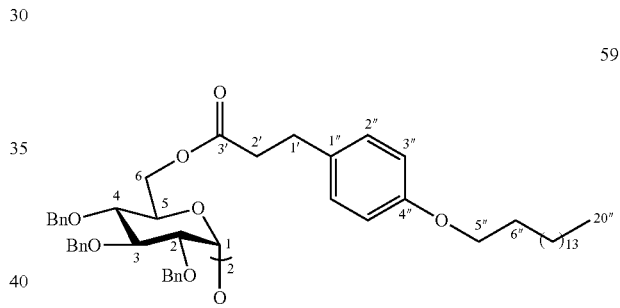

6,6'-di-O-(3-[4-(hexadecyloxy)phenyl]propanoate)-α,α'-D-trehalose (43d): To a solution of diester 59 (103 mg, 0.066 mmol) in MeOH:CH$_2$Cl$_2$ (3 mL, 1:1, v/v) was added Pd(OH)$_2$/C (50 mg). H$_2$-gas was bubbled through the reaction mixture overnight. The following day, the reaction mixture was diluted in pyridine and filtered over celite and concentrated in vacuo. The resulting residue was purified by silica-gel column chromatography (1:0-9:1, EtOAc:MeOH, v/v) to give the title compound as an off-white amorphous solid (43 mg, 0.042 mmol, 64%). R$_f$=0.56 (4:1, EtOAc:MeOH, v/v); [α]$^{27.7}_D$=+50.6 (c=0.1, pyridine); $^1$H NMR (500 MHz, C$_5$D$_5$N) δ 7.18 (d, J$_{2'',3''}$=8.5 Hz, 4H, H-2''), 6.99 (d, J$_{2'',3''}$=8.5 Hz, 4H, H-3''), 5.92 (d, J$_{1,2}$=3.7 Hz, 2H, H-1), 5.13 (ddd, J$_{4,5}$=10.1 Hz, J$_{5,6b}$=5.4 Hz, J$_{5,6a}$=1.6 Hz, 2H, H-5), 5.02 (m, 2H, H-6a), 4.83 (dd, J$_{6a,6b}$=11.7 Hz, J$_{6b,5}$=5.6 Hz, 2H, H-6b), 4.76 (t, J$_{3,4}$=J$_{2,3}$=9.1 Hz, 2H, H-3), 4.33 (dd, J$_{2,3}$=9.6 Hz, J$_{2,1}$=3.7 Hz, 2H, H-2), 4.18 (t, J$_{3,4}$=14,5=9.4 Hz, 2H, H-4), 3.92 (t, J$_{5'',6''}$=6.5 Hz, 4H, CH$_2$-6''), 2.96 (t, J$_{1,2'}$=7.8 Hz, 4H, CH$_2$-1'), 2.67 (m, 4H, CH$_2$-2'), 1.76 (p, J$_{5'',6''}$=J$_{6'',7''}$=6.6 Hz, 4H, CH$_2$-7''), 1.44 (m, 4H, CH$_2$-7''), 1.34-1.23 (m, 48H, CH$_2$-8''-CH$_2$-19''), 0.88 (t, J$_{19'',20''}$=7.1 Hz, 6H, CH$_3$-20''); $^{13}$C NMR (150 MHz, C$_5$D$_5$N) δ 173.3 (C-3'), 158.5 (C-4''), 133.4 (C-1''), 130.1 (C-2''), 115.3 (C-3''), 96.3 (C-1), 75.3 (C-3), 73.8 (C-2), 72.4 (C-4), 72.0 (C-5), 68.5 (CH$_2$-5''), 65.0 (C-6), 36.8 (CH$_2$-2'), 32.5, 30.8, 30.4, 30.3, 30.1, 30.05, 30.0, 23.3 (CH$_2$-1", CH$_2$-6", CH$_2$-8"-CH$_2$-19"), 26.8 (CH$_2$-7"), 14.7 (CH$_3$-20"); IR (film) 3360, 2916, 2849, 1718, 1297, 990, 721 cm$^{-1}$; HRMS (ESI) calcd. for [C$_{62}$H$_{102}$O$_{15}$+NH$_4$]$^+$: 1104.7557; obsd.: 1104.7604.

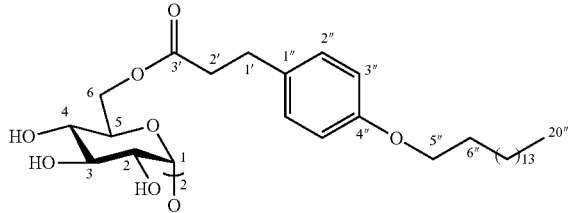

43d 2,2',3,3',4,4'-Hexa-O-trimethylsilyl-6,6'-di-O-(4-hexadecyloxycinnamate)-α,α'-D-trehalose (64): 2,2',3,3',4,4'-Hexa-O-trimethylsilyl-α,α'-D-trehalose (150 mg, 0.193 mmol) and 4-hexadecyloxycinnamic acid (388 mg, 0.871 mmol) were co-evaporated with toluene (2×5 mL) and then re-dissolved in dry toluene (6 mL). To the resulting solution was added EDCI (258 mg, 1.35 mmol) and DMAP (38 mg, 0.311 mmol) and the mixture was stirred at 50° C. overnight. The following day, additional portions of 4-hexadecyloxycinnamic acid (43 mg, 0.111 mmol) and EDCI (42 mg, 0.219 mmol) and the mixture was left to stir for a further 2 hours. The reaction mixture was diluted with EtOAc (50 mL), washed with water and brine, dried over MgSO$_4$, filtered, and concentrated under reduced pressure. The resulting residue was purified by silica-gel column chromatography (1:0-3:2, pet. ether:EtOAc, v/v) and lipophilic size exclusion (1:1, CH$_2$Cl$_2$:MeOH, v/v) to give the title compound as a clear oil (117 mg, 0.077 mmol, 34%). R$_f$=0.77 (4:1, pet. ether:EtOAc, v/v); $^1$H NMR (500 MHz, CDCl$_3$) δ 7.66 (d, J$_{1,2}$=15.9 Hz, 2H, H-1'), 7.47 (d, J$_{2",3"}$=8.8 Hz, 4H, H-2"), 6.89 (d, J$_{2",3"}$=8.8 Hz, 4H, H-3"), 6.35 (d, J$_{1,2}$=15.9 Hz, 2H, H-2'), 4.99 (d, J$_{1,2}$=3.1 Hz, 2H, H-1), 4.39 (dd, J$_{6a,6b}$=12.1 Hz, J$_{6a,5}$=2.2 Hz, 2H, H-6a), 4.20 (dd, J$_{6a,6b}$=12.1 Hz, J$_{6b,5}$=4.3 Hz, 2H, H-6b), 4.08 (m, 2H, H-5), 3.96 (m, 6H, H-3, CH$_2$-5"), 3.57 (t, J$_{3,4}$=14,5=9.0 Hz, 2H, H-4), 3.51 (dd, J$_{2,3}$=9.3 Hz, J$_{1,2}$=3.1 Hz, 2H, H-2), 1.78 (p, J$_{5",6"}$=J$_{6",7"}$=6.6 Hz, 4H, CH$_2$-6"), 1.44 (m, 4H, CH$_2$-7"), 1.39-1.21 (m, 48H, CH$_2$-8"-CH$_2$-19"), 0.88 (t, J$_{9",20"}$=7.1 Hz, 6H, CH$_3$-20'), 0.17 (s, 18H, CH$_3$-TMS), 0.16 (s, 18H, CH$_3$-TMS), 0.14 (s, 18H, CH$_3$-TMS); $^{13}$C NMR (125 MHz, CDCl$_3$) δ 167.5 (C-3'), 161.2 (C-4"), 145.1 (C-1'), 129.9 (C-2"), 127.0 (C-1"), 115.1 (C-2'), 115.0 (C-3"), 94.7 (C-1), 73.7 (C-3), 72.8 (C-2), 72.1 (C-4), 71.0 (C-5), 68.3 (CH$_2$-5"), 63.6 (C-6), 32.1, 29.9, 29.83, 29.81, 29.75, 29.72, 29.53, 29.52, 29.3, 22.9 (CH$_2$-6", CH$_2$-8"-CH$_2$-9"), 26.2 (C-7"), 14.3 (CH$_3$-20'), 1.24, 1.1, 0.4 (CH$_3$-TMS); IR (film): 2920, 2851, 1719, 1603, 1250, 1171, 1046, 840 cm$^{-1}$; HRMS (ESI) calcd. for [C$_{80}$H$_{146}$O$_5$Si$_6$+NH$_4$]$^+$: 1532.9616; obsd.: 1532.9610.

64

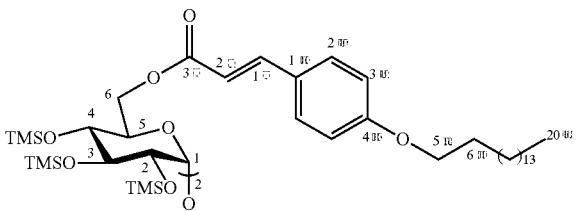

6,6'-Di-O-(4-hexadecyloxycinnamate)-α,α'-D-trehalose (43e): To a solution of diester 64 (116 mg, 0.076 mmol) in CH$_2$Cl$_2$:MeOH (1:1, 10 mL), was added Dowex-H$^+$ (35 mg) and the resulting suspension was left to stir at room temperature for 30 minutes. The reaction mixture was filtered, concentrated under reduced pressure, and purified by silica-gel column chromatography (1:0-4:1, EtOAc:MeOH, v/v) to give the title compound as a white amorphous solid (32 mg, 0.030 mmol, 40%). R$_f$=0.71 (4:1, EtOAc:MeOH, v/v); [α]$^{27.6}_D$=+42.8 (c=0.1, pyridine); $^1$H NMR (500 MHz, C$_5$D$_5$N) δ 7.94 (d, J$_{1,2}$=15.9 Hz, 2H, H-1'), 7.49 (d, J$_{2",3"}$=8.7 Hz, 4H, H-2"), 7.44 (m, 1H, OH), 7.17 (m, 2H, OH), 7.00 (d, J$_{2",3"}$=8.8 Hz, 2H, H-3"), 6.60 (d, J$_{1,2}$=15.9 Hz, 2H, H-2'), 5.99 (d, J$_{1,2}$=3.8 Hz, 2H, H-1), 5.23 (ddd, J$_{4,5}$=9.9 Hz, J$_{5,6b}$=4.9 Hz, J$_{5,6a}$=1.8 Hz, 2H, H-5), 5.11 (dd, J$_{6a,6b}$=11.8 Hz, J$_{6a,5}$=1.9 Hz, 2H, H-6a), 5.02 (dd, J$_{6a,6b}$=11.8 Hz, J$_{6b,5}$=5.3 Hz, 2H, H-6b), 4.82 (t, J$_{3,4}$=J$_{2,3}$=9.3 Hz, 2H, H-3), 4.38 (m, 2H, H-2), 4.27 (td, J$_{3,4}$=14, 5=9.5 Hz, J=3.9 Hz, 2H, H-4), 3.93 (t, J$_{5",6"}$=6.52, 4H, CH$_2$-5"), 1.75 (p, J$_{5",6"}$=J$_{6",7"}$=6.5 Hz, 4H, CH$_2$-6"), 1.43 (m, 4H, CH$_2$-7"), 1.31-1.23 (m, 48H, CH$_2$-8"-CH$_2$-19"), 0.87 (t, J$_{19",20"}$=7.1 Hz, 6H, CH$_3$-20"); $^{13}$C NMR (150 MHz, C$_5$D$_5$N) δ 167.8 (C-3'), 161.8 (C-4"), 145.1 (C-1'), 130.7 (C-2"), 127.8 (C-1"), 116.6 (C-2'), 115.6 (C-3"), 96.5 (C-1), 75.3 (C-3), 73.8 (C-2), 72.4 (C-4), 72.1 (C-5), 68.7 (CH$_2$-5"), 65.0 (C-6), 32.5, 30.4, 30.34, 30.30, 30.27, 30.25, 30.03, 29.99, 29.85, 23.3 (CH$_2$-6", CH$_2$-8"-CH$_2$-19"), 26.7 (C-7"), 14.7 (CH$_3$-20"); IR (film): 3342, 2917, 2850, 1700, 1603, 1250, 1172, 1017, 825 cm$^{-1}$; HRMS (ESI) calcd. For [C$_{62}$H$_{98}$O$_{15}$+H]$^+$: 1083.6983; obsd.: 1083.6981.

43e

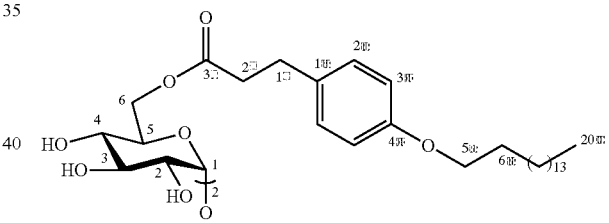

2,2',3,3',4,4'-Hexa-O-benzyl-6,6'-di-O-[4-(nonadec-1-en-1-yl)benzoate]-α,α'-D-trehalose (70): 2,2',3,3',4,4'-Hexa-O-benzyl-α,α'-D-trehalose (105 mg, 0.119 mmol) and 4-(Nonadec-1-en-1-yl)benzoic acid (207 mg, 0.535 mmol) were co-evaporated with toluene (2×5 mL) and then re-dissolved in dry toluene (3 mL). To the resulting solution was added EDCI (157 mg, 0.819 mmol) and DMAP (18 mg, 0.147 mmol) and the mixture was stirred at 70° C. overnight. The following day, the reaction mixture was diluted with EtOAc (50 mL), washed with water and brine, dried over MgSO$_4$, filtered, and concentrated under reduced pressure. The resulting residue was purified by silica-gel column chromatography (1:0-23:2, pet. ether:EtOAc, v/v) to give the title compound as a clear oil (65 mg, 0.040 mmol, 34%). R$_f$=0.50 (4:1, pet. Ether:EtOAc, v/v); [α]$^{21}_D$=+64 (c=1.0, CH$_2$Cl$_2$); $^1$H NMR (500 MHz, CDCl$_3$) δ 7.92 (d, J$_{2,3'}$=8.3 Hz, 4H, H-2'), 7.39-7.21 (m, 34H, CH$_{arom}$, H-3'), 6.42-6.33 (m, 2H, H-5), 5.77 (dt, J$_{5,6}$=11.7 Hz, J$_{6,7}$=7.3 Hz, 2H, H-6'), 5.23 (d, J$_{1,2}$=3.5 Hz, 2H, H-1), 5.04 (d, J$_{a,b}$=10.7 Hz, 2H, CH$_a$ 3-O—Bn), 4.91 (m, 4H, CH$_b$ 3-O—Bn, CH$_a$ 4-O—Bn), 7.74 (d, J$_{a,b}$=11.9 Hz, 2H, CH$_a$ 2-O—Bn), 4.70 (d, J$_{a,b}$=11.9 Hz, 2H, CH$_b$ 2-O—Bn), 4.59 (d, J$_{a,b}$=10.7 Hz, 2H, CH$_b$ 4-O—Bn), 4.37-4.24 (m, 6H, H-6, H-5), 4.11 (t, J$_{2,3}$=J$_3$, 4=9.3 Hz, 2H, H-3), 3.69 (t, $J_{3,4}$=14,5=9.5 Hz, 2H, H-4), 3.63 (dd, $J_{2,3}$=9.7 Hz, $J_{1,2}$=3.5 Hz, 2H, H-2), 2.31 (m, 4H, $CH_2$-7'), 1.45 (m, 4H, $CH_2$-8'), 1.35-1.19 (m, 56H, $CH_2$-9'-$CH_2$-22'), 0.87 (t, $J_{22',23'}$=7.0 Hz, 6H, $CH_3$-23'); $^{13}C$ NMR (150 MHz, CDCl$_3$) δ 166.2 (C-7), 142.8 (C-4), 138.7 ($C_i$, 3-O—Bn), 138.00, 137.95 ($C_i$, 2-O—Bn, 4-O—Bn), 135.8 (C-6'), 129.7 (C-2), 128.8, 128.7, 128.3, 128.2, 128.1, 128.0, 127.93, 127.89, 127.82, 127.5 ($CH_{arom}$, C-3', C-1'), 94.2 (C-1), 81.9 (C-3), 79.7 (C-2), 77.9 (C-4), 76.0 ($CH_2$, 3-O—Bn), 75.5 ($CH_2$, 4-O—Bn), 73.2 ($CH_2$, 2-O-n), 69.5 (C-5), 63.1 (C-6), 32.1, 30.0, 29.9, 29.8, 29.76, 29.71, 29.5, 22.9 ($CH_2$-8'-$CH_2$-22'), 29.0 ($CH_2$-8') 14.3 ($CH_3$-23'); IR (film): 2923, 2852, 1734, 1607, 1466, 1273, 1097, 1072, 998, 749, 696 cm$^{-1}$; HRMS (ESI) calcd. for $[C_{106}H_{138}O_{13}+NH_4]^+$: 1637.0476; obsd.: 1637.0494.

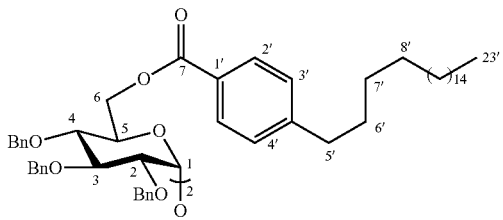

70

6,6'-di-O—[(Z)-4-(nonadec-1-en-1-yl)benzoate]–α,α'-D-trehalose (43f): To a solution of diester 70 (62 mg, 0.038 mmol) in MeOH:CH$_2$Cl$_2$ (2.5 mL, 1:1, v/v) was added Pd(OH)$_2$/C (37 mg). H$_2$ gas was bubbled through the reaction mixture overnight. After 12 hours, the reaction mixture was diluted, filtered over celite, and concentrated in vacuo. The resulting residue was purified by silica-gel column chromatography (1:0-9:1, EtOAc:MeOH, v/v) to give the title compound as an off-white solid (24 mg, 0.022 mmol, 58%). $R_f$=0.76 (4:1, EtOAc:MeOH, v/v); $[α]^{22.0}_D$=+60 (c=0.1, pyridine); $^1H$ NMR (500 MHz, C$_5$D$_5$N) δ 8.24 (d, $J_{2',3'}$=8.2 Hz, 4H, H-2'), 7.49 (m, 2H, OH), 7.19 (d, $J_{2',3'}$=8.1 Hz, 4H, H-3'), 5.97 (d, $J_{1,2}$=3.7 Hz, 2H, H-1), 5.29 (ddd, $J_{4,5}$=10.1 Hz, $J_{6a,6b}$=5.5 Hz, $J_{6a,5}$=2.0 Hz, 2H, H-5), 5.20 (dd, $J_{5,6b}$=11.8 Hz, $J_{6a,6b}$=2.1 Hz, 2H, H-6a), 5.08 (m, H-6b), 4.83 (t, $J_{2,3}$=$J_{3,4}$=9.2 Hz, 2H, H-3), 4.40 (m, 2H, H-2), 4.28 (t, $J_{3,4}$=14,5=9.4 Hz, 2H, H-4), 2.56 (t, $J_{5',6'}$=7.7 Hz, 4H, $CH_2$-5'), 1.55 (m, 4H, $CH_2$-6'), 1.36-1.21 (m, 64H, $CH_2$-7'-$CH_2$-22'), 0.88 (t, $J_{23,24}$=7.2 Hz, 6H, $CH_3$-23'); $^{13}C$ NMR (150 MHz, C$_5$D$_5$N) δ 167.2 (C-7), 149.0 (C-4), 130.5 (C-2'), 129.2 (C-3'), 128.9 (C-1'), 96.3 (C-1), 75.4 (C-3), 73.8 (C-2), 72.5 (C-4), 72.0 (C-5), 65.5 (C-6), 36.4 ($CH_2$-5'), 31.7 ($CH_2$-6'), 32.5, 30.37, 30.36, 30.35, 30.29, 30.27, 30.1, 30.0, 29.9, 23.3 ($CH_2$-7'-$CH_2$-22'), 14.7 ($CH_3$-23'); IR (film): 3357, 2917, 2850, 1716, 1467, 1415, 1283, 1102, 1077, 1046, 1019, 721 cm$^{-1}$; HRMS (ESI) calcd. for $[C_{64}H_{106}O_3+NH_4]^+$: 1100.7972; obsd.: 1100.7992.

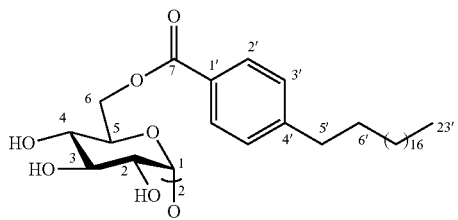

43f 2,2',3,3',4,4'-Hexa-O-benzyl-6,6'-di-O-(4-(octadecylamino)benzoate)-α,α'-D-trehalose (76): 2,2',3,3',4,4'-Hexa-O-benzyl-α,α'-D-trehalose (107 mg, 0.121 mmol) and 4-(octadecylamino)benzoic acid (211 mg, 0.542 mmol) were co-evaporated with toluene (2×5 mL) and then re-dissolved in dry toluene (3 mL). To the resulting solution was added EDCI (151 mg, 0.787 mmol) and DMAP (15 mg, 0.121 mmol) and the mixture was stirred at 70° C. overnight. The following day, the reaction mixture was diluted with EtOAc (50 mL), washed with water and brine, dried over MgSO$_4$, filtered, and concentrated under reduced pressure. The resulting residue was purified by silica-gel column chromatography (1:0-3:1, pet. ether:EtOAc, v/v) to give the title compound as a clear oil (75 mg, 0.046 mmol, 38%). $R_f$ 35=0.46 (4:1, pet. ether:EtOAc, v/v); $[α]^{23}_D$=+66 (c=1.0, CH$_2$Cl$_2$); $^1H$ NMR (500 MHz, CDCl$_3$) δ 7.84 (d, $J_{2',3'}$=8.9 Hz, 4H, H-2'), 7.42-7.27 (m, 30H, $CH_{arom}$), 6.53 (d, $J_{2',3'}$=8.8 Hz, 4H, H-3'), 5.28 (d, $J_{1,2}$=3.5 Hz, 2H, H-1), 5.06 (d, $J_{a,b}$=10.7 Hz, 2H, $CH_a$ 3-O—Bn), 4.93 (d, $J_{a,b}$=10.8 Hz, 2H, $CH_b$ 3-O—Bn), 4.91 (d, $J_{a,b}$=10.7 Hz, 2H, $CH_a$ 4-O—Bn), 4.75 (m, 4H, $CH_2$ 2-O—Bn), 4.61 (d, $J_{a,b}$=10.5 Hz, 2H, $CH_b$ 4-O—Bn), 4.39-4.25 (m, 6H, H-5, H-6), 4.16-4.10 (m, 2H, H-3), 3.73 (t, $J_{3,4}$=$J_{4,5}$=9.7 Hz, 2H, H-4), 3.66 (dd, $J_{2,3}$=9.6 Hz, $J_{1,2}$=3.4 Hz, 2H, H-2), 3.17 (m, 4H, $CH_2$-6'), 1.65 (m, 4H, $CH_2$-7'), 1.42 (m, 4H, $CH_2$-8'), 1.38-1.25 (m, 28H, $CH_2$-9'-$CH_2$-22'), 0.91 (t, $J_{22',23}$=7.2 Hz, 6H, $CH_3$-23'); $^{13}C$ NMR (125 MHz, CDCl$_3$) δ 166.5 (C-5'), 152.4 (C-4'), 138.7 ($C_i$, 3-O—Bn), 138.04 ($C_i$, 4-O—Bn), 137.97 ($C_i$, 2-O—Bn), 131.8 (C-2'), 128.60, 128.59, 128.3, 128.2, 128.0, 127.9, 127.8, 127.6 ($CH_{arom}$), 117.8 (C-1'), 111.4 (C-3'), 94.1 (C-1), 81.8 (C-3), 79.6 (C-2), 78.0 (C-4), 76.0 ($CH_2$, 3-O—Bn), 75.5 ($CH_2$, 4-O—Bn), 73.0 ($CH_2$, 2-O—Bn), 69.6 (C-5), 62.5 (C-6), 43.5 ($CH_2$-6'), 32.1, 29.84, 29.81, 29.80, 29.74, 29.72, 29.6, 29.50, 29.45 ($CH_2$-7', $CH_2$-9'-$CH_2$-22'), 27.2 ($CH_2$-8'), 14.3 ($CH_3$-23'); IR (film): 3380, 2921, 2852, 1706, 1604, 1527, 1497, 1418, 1267, 1172, 1095, 1070, 998, 733, 696 cm$^{-1}$; HRMS (ESI) calcd. for $[C_{104}H_{140}N_2O_{13}+H]^+$: 1626.0428; obsd.: 1626.0490.

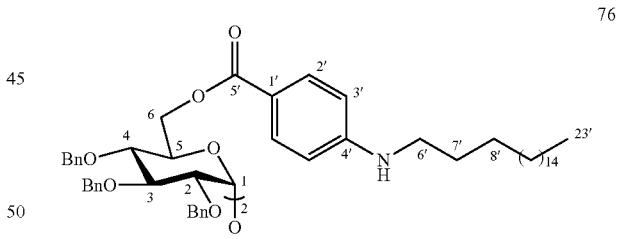

76

6,6'-di-O-(4-(octadecylamino)benzoate)-α,α'-D-trehalose (43g): To a solution of diester 76 (74 mg, 0.046 mmol) in MeOH:CH$_2$Cl$_2$ (3 mL, 1:1, v/v) was added Pd(OH)$_2$/C (44 mg). H$_2$ gas was bubbled through the reaction mixture. After 48 hours, the reaction mixture was diluted with pyridine, filtered over celite, and concentrated in vacuo. The resulting residue was purified by silica-gel column chromatography (1:0-4:1, EtOAc:MeOH, v/v) to give the title compound as an off-white solid (14 mg, 0.013 mmol, 28%). $R_f$=0.71 (9:1, EtOAc:MeOH, v/v); $[α]^{21.0}_D$=+80 (c=0.025, pyridine); $^1H$ NMR (600 MHz, C$_5$D$_5$N) δ 8.23 (d, $J_{2',3'}$=8.8 Hz, 4H, H-2'), 7.31 (m, 2H, OH), 7.08 (m, 4H, OH), 6.62 (d, $J_{2',3'}$=8.9 Hz, 4H, H-3'), 6.70 (m, 2H, NH), 5.99 (d, $J_{1,2}$=3.7 Hz, 2H, H-1), 5.27 (ddd, $J_{4,5}$=9.7 Hz, $J_{5,6b}$=5.2 Hz, $J_{5,6a}$=1.8 Hz, 2H, H-5), 5.19 (dd, $J_{6a,6b}$=11.6, $J_{5,6a}$=1.8 Hz, 2H, H-6a), 5.07 (dd, $J_{6a,6b}$=11.7 Hz, $J_{5,6b}$=5.3 Hz, 2H, H-6b), 4.82 (dt, $J_{3,4}$=$J_{2,3}$=9.4 Hz, $J_{a,b}$=3.1 Hz, 2H, H-3), 4.38 (m, 2H, H-2), 4.31 (td, $J_{3,4}$=$J_{4,5}$=9.4 Hz, $J_{a,b}$=5.3 Hz, 2H, H-4), 3.14 (q, $J_{NH,6'}$=$J_{6',7'}$=6.5 Hz, 4H, CH$_2$-6'), 1.62 (p, $J_{6',7'}$=$J_{7',8'}$=7.4 Hz, 4H, CH$_2$-7'), 1.39-1.17 (m, 60H, CH$_2$-8'-CH$_2$-22'), 0.88 (t, $J_{22',23'}$=7.2 Hz, 6H, CH$_3$-23'); $^{13}$C NMR (150 MHz, C$_5$D$_5$N) δ 167.7 (C-5), 154.1 (C-4'), 132.6 (C-2'), 118.2 (C-1'), 111.9 (C-3'), 96.5 (C-1), 75.5 (C-3), 74.0 (C-2), 72.6 (C-4), 72.3 (C-5), 64.9 (C-6), 43.9 (CH$_2$-6'), 32.6, 30.47, 30.39, 30.2, 30.1, 29.9, 28.0, 23.4 (CH$_2$-7'-CH$_2$-22'), 14.8 (CH$_3$-23'); HRMS (ESI) calcd. For [C$_{62}$H$_{104}$N$_2$O$_{13}$+H]$^+$: 1085.7611; obsd.: 1085.7589.

43g

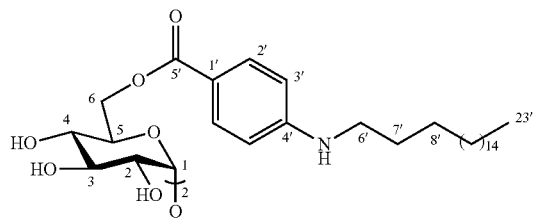

2,2',3,3',4,4'-Hexa-O-trimethylsilyl-6,6'-di-O-(4-[octadecylthio]benzoate)-α,α'-D-trehalose (80): 2,2',3,3',4,4'-Hexa-O-trimethylsilyl-α,α'-D-trehalose (110 mg, 0.142 mmol) and 4-(octadecylthio)benzoic acid (346 mg, 0.851 mmol) were co-evaporated with toluene (2×5 mL) and then re-dissolved in dry toluene (5 mL). To the resulting solution was added EDCI (186 mg, 0.923 mmol) and DMAP (20 mg, 0.164 mmol) and the mixture was stirred at 70° C. for 48 hours. The reaction mixture was diluted with EtOAc (50 mL), washed with water and brine, dried over MgSO$_4$, filtered, and concentrated under reduced pressure. The resulting residue was purified by silica-gel column chromatography (1:0-19:1, pet. ether:EtOAc, v/v) to give the title compound as a clear oil (170 mg, 0.110 mmol, 77%). $R_f$=0.59 (9:1, pet. ether:EtOAc, v/v); [α]$^{21.6}_D$=+30 (c=1.0, CH$_2$Cl$_2$; $^1$H NMR (500 MHz, CDCl$_3$) δ 7.93 (d, $J_{2',3'}$=8.4 Hz, 4H, H-2'), 7.29 (d, $J_{2',3'}$=8.4 Hz, 4H, H-3'), 4.97 (d, $J_{1,2}$=2.9 Hz, 2H, H-1), 4.55 (dd, $J_{6a,6b}$=12.0 Hz, $J_{5,6a}$=2.1 Hz, 2H, H-6a), 4.26 (dd, $J_{6a,6b}$=12.1 Hz, $J_{5,6b}$=3.41, 2H, H-6b), 4.12 (m, 2H, H-5), 3.97 (t, $J_{2,3}$=33,4=8.9 Hz, 2H, H-3), 3.64 (t, $J_{3,4}$=34,5=9.0 Hz, 2H, H-4), 3.49 (dd, $J_{2,3}$=9.3 Hz, $J_{1,2}$=3.0 Hz, 2H, H-2), 2.98 (t, $J_{6',7'}$=7.4 Hz, 4H, CH$_2$-6'), 1.69 (p, $J_{6',7'}$=$J_{7',8'}$=7.3 Hz, 4H, CH$_2$-7'), 1.44 (m, 4H, CH$_2$-8'), 1.33-1.22 (m, 56H, CH$_2$-9'-CH$_2$-22'), 0.88 (t, $J_{22',23'}$=7.1 Hz, 6H, CH$_3$-23'), 0.18 (s, 18H, CH$_3$-TMS), 0.15 (s, 18H, CH$_3$-TMS), 0.13 (s, 18H, CH$_3$-TMS); $^{13}$C NMR (125 MHz, CDCl$_3$) δ 166.3 (C-5'), 144.9 (C-4'), 130.1 (C-2'), 126.4 (C-1'), 126.3 (C-3'), 94.8 (C-1), 73.8 (C-3), 72.9 (C-2), 72.1 (C-4), 71.0 (C-5), 63.7 (C-6), 32.2 (C-6'), 32.1, 29.85, 29.82, 29.81, 29.80, 29.74, 29.66, 29.52, 29.3, 29.1, 28.9 (CH$_2$-9'-CH$_2$-22'), 29.1 (CH$_2$-8'), 28.9 (CH$_2$-7'), 14.3 (CH$_3$-23'), 1.3, 1.1, 0.4 (CH$_3$-TMS); IR (film): 2922, 2852, 1718, 1593, 1457, 1401, 1263, 1148, 1099, 869, 838, 757 cm$^{-1}$; HRMS (ESI) calcd. for [C$_{80}$H$_{150}$O$_{13}$S$_2$Si$_6$+NH$_4$]$^+$: 1568.9472; obsd.: 1568.9496.

80

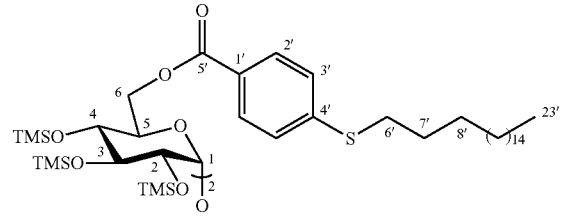

6,6'-di-O-(4-[octadecylthio]benzoate)-α,α'-D-trehalose (43h): To a solution of diester 80 (160 mg, 0.103 mmol) in CH$_2$Cl$_2$:MeOH (1:1, 5 mL) was added Dowex-H$^+$ (23 mg) and the resulting suspension was left to stir at room temperature for 1 hour. The reaction mixture was filtered and concentrated under reduced pressure to yield the title compound as a white solid, which was precipitated from hot EtOH (60 mg, 0.054 mmol, 52%). $R_f$=0.68 (4:1, EtOAc:MeOH, v/v); [α]$^{22.6}_D$=+60 (c=0.1, CH$_2$Cl$_2$$^1$H NMR (500 MHz, C$_5$D$_5$N) δ 8.19 (d, $J_{2',3'}$=8.5 Hz, 4H, H-2'), 7.47 (m, 2H, OH), 7.32 (d, $J_{2',3'}$=8.4 Hz, 4H, H-3'), 1.19 (m, 4H, OH), 5.96 (d, $J_{1,2}$=3.7 Hz, 2H, H-1), 5.28 (ddd, $J_{4,5}$=10.0 Hz, $J_{6,6a}$=5.5 Hz, $J_{5,6a}$=1.8 Hz, 2H, H-5), 5.20 (dd, $J_{6a,6b}$=11.7 Hz, $J_{5,6a}$=1.7 Hz, 2H, H-6a), 5.05 (dd, $J_{6a,6b}$=11.7 Hz, $J_{5,6b}$=5.7 Hz, 2H, H-6b), 4.81 (td, $J_{2,3}$=$J_{3,4}$=9.4 Hz, $J_{a,b}$=2.9 Hz, H-3), 4.38 (m, 2H, H-2), 4.26 (td, $J_{4,5}$=$J_{3,4}$=9.6 Hz, $J_{a,b}$=5.2 Hz, 2H, H-4), 2.97 (t, $J_{6',7'}$=7.4 Hz, 4H, CH$_2$-6'), 1.66 (p, $J_{6',7'}$=$J_{7,8}$=7.4 Hz, 4H, CH$_2$-7), 1.41 (m, 4H, CH$_2$-8'), 1.36-1.19 (m, 56H, CH$_2$-9'-CH$_2$-22'), 0.88 (t, $J_{22',23'}$=7.1 Hz, 6H, CH$_3$-23'); $^{13}$C NMR (150 MHz, C$_5$D$_5$N) δ 166.9 (C-5), 145.4 (C-4'), 130.9 (C-2'), 127.8 (C-1'), 127.0 (C-3), 96.5 (C-1), 75.5 (C-3), 73.9 (C-2), 72.6 (C-4), 72.2 (C-5), 65.7 (C-6), 32.4 (CH$_2$-6'), 32.6, 30.48, 30.46, 30.44, 30.40, 30.36, 30.28, 30.1, 29.9, 29.6, 29.5, 23.4 (CH$_2$-7'-CH$_2$-22'), 14.8 (CH$_3$-23'); IR (film): 3353, 2917, 2849, 1713, 1593, 1470, 1400, 1275, 1100, 1077, 1042, 759 cm$^{-1}$; HRMS (ESI) calcd. For [C$_{62}$H$_{102}$O$_{13}$S$_2$+NH$_4$]$^+$: 1136.7100; obsd.: 1136.7117.

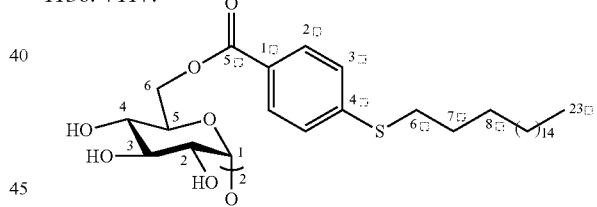

General procedure for the Staudinger reduction and coupling reaction. To a stirred solution of 6,6'-diazido-6,6'-dideoxy-α,α'-trehalose in DMF (0.08 mmol/mL) at 0° C. were added 1.0 M PMe$_3$ in THF (10 equiv.) and water (60 equiv.). The solution was stirred for 10 minutes at 0° C., then allowed to warm to room temperature, and stirred for a further 20 hours. The mixture was concentrated and the residue co-evaporated with distilled pyridine (0.02 mmol/mL)×2 and then dissolved in distilled pyridine (2×0.02 mmol/mL). To this solution was added carboxylic acid (2.5 equiv.), DIPEA (5 equiv.) and then HBTU (2.5 equiv.). The reaction mixture was stirred overnight at room temperature and then concentrated. The residue was purified as detailed in individual procedure.

6,6'-Diazido-6,6'-dideoxy-α,α'-trehalose (54 mg, 0.14 mmol), PMe$_3$ (1.4 mL. 1.4 mmol), water (0.15 mL, 8.3 mmol), 4-octadecyloxybenzoic acid (137 mg, 0.35 mmol), DIPEA (0.12 mL, 0.74 mmol), and HBTU (132 mg, 0.35 mmol) were subjected to the general procedure for the Staudinger reduction and coupling reaction. The resultant residue was dissolved in hot $^t$BuOH:EtOAc (40 mL, 2:1, v/v) and washed with HCl (75 mL, 0.1 M), sat. NaHCO$_3$ (75 mL) and brine (75 mL). The organic layer was diluted with pyridine (10 mL), dried (MgSO$_4$), filtered and concentrated. The resultant residue was purified by gradient silica gel flash chromatography (CH$_2$Cl$_2$ to CH$_2$Cl$_2$:MeOH, 85:15, v/v) to give the title compound as a white solid (85 mg, 0.08 mmol, 57%). R$_f$=0.61 (CH$_2$Cl$_2$:MeOH, 4:1, v/v); [α]$^{21}_D$=+28 (c=1.0, pyridine); IR (film) 3327, 2915, 2849, 1623, 1607, 1551, 1505, 1467, 1302, 1254, 1182, 1147, 1103, 1035, 993, 840 cm$^{-1}$; $^1$H-NMR (500 MHz, C$_5$D$_5$N) δ 9.02 (bs, 2H, NH), 8.33 (d, J$_{2',3'}$=8.6 Hz, 4H, H-2'), 7.06 (d, J$_{2',3'}$=8.9 Hz, 4H, H-3'), 5.76 (d, J$_{1,2}$=3.5 Hz, 2H, H-1), 5.06 (m, 1H, H-5), 4.70 (t, J$_{3,4}$=14,5=9.3 Hz, 2H, H-3), 4.43 (dd, J$_{6a,6b}$=13.0 Hz, J$_{5,6a}$=6.2 Hz, 2H, H-6a), 4.24 (dd, J$_{2,3}$=9.5 Hz, J$_{1,2}$=6.2 Hz, 2H, H-2), 4.14 (bd, J$_{6a,6b}$=13.9 Hz, 2H, H-6b), 4.00 (t, J$_{3,4}$=14,5=9.6 Hz, 2H, H-4), 3.92 (t, J$_{5',6'}$=6.6 Hz, 4H, H-5'), 1.74 (p, J$_{5',6'}$=J$_{6',7'}$=7.1 Hz, 4H, H-6'), 1.46-1.39 (m, 4H, H-7'), 1.35-1.22 (m, 28H, H-8'-H-21'), 0.88 (t, J$_{21',22'}$=6.9 Hz, 6H, H-22'); $^{13}$C-NMR (150 MHz, C$_5$D$_5$N) δ 169.0 (C=O), 162.6 (C-4'), 130.4 (C-2'), 128.2 (C-1'), 115.0 (C-3'), 97.1 (C-1), 74.8 (C-3), 74.0 (C-2), 73.9 (C-4), 72.9 (C-5), 68.8 (C-5') 44.7 (C-6), 42.5, 32.6, 30.48, 30.47, 30.41, 30.40, 30.37, 30.2, 30.1, 30.0, 23.43 (C-6' & C-8'-C-21'), 26.8 (C-7'), 14.8 (C-22'); HRMS (ESI) m/z [M+H]$^+$ calcd. for [C$_{62}$H$_{104}$N$_2$O$_{13}$+H]$^+$: 1085.7611, obsd. 1085.7609.

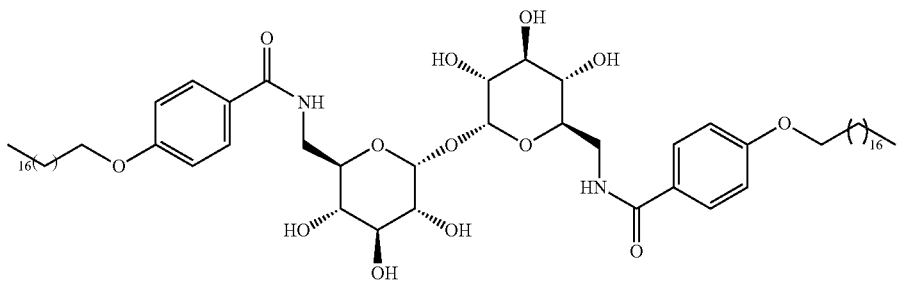

6,6'-Dideoxy-di-(2-O-benzyl-4-octadecyloxy-benzoylamido)-α,α'-trehalose. 6,6'-Diazido-6,6'-dideoxy-α,α'-trehalose (63 mg, 0.16 mmol), PMe$_3$ (1.6 mL, 1.6 mmol), water (0.17 mL, 9.4 mmol), 2-(benzyloxy)-4-(octadecyloxy) benzoic acid (198 mg, 0.40 mmol), HBTU (152 mg, 0.40 mmol) and DIPEA (0.14 mL, 0.80 mmol) were subjected to the general procedure for the Staudinger reduction and coupling reaction. The resultant residue was dissolved in hot $^t$BuOH:EtOAc (70 mL, 2:1, v/v) and washed with HCl (100 mL, 0.1 M), sat. NaHCO$_3$ (100 mL), and brine (100 mL). The organic layer was diluted with pyridine (10 mL), dried (MgSO$_4$), filtered and concentrated. The resultant residue was purified by gradient silica gel flash column chromatography (CH$_2$Cl$_2$ to CH$_2$Cl$_2$:MeOH, 9:1, v/v) to give the title compound as a white solid (193 mg, 0.15 mmol, 93%). R$_f$=0.35 (CH$_2$Cl$_2$:MeOH, 9:1, v/v); [α]$^{19}_D$=+39 (c=1.0, pyridine); IR (film) 3387, 2916, 2849, 1628, 1605, 1544, 1498, 1466, 1391, 1257, 1175, 1146, 1110, 1035, 996, 840 cm$^{-1}$; $^1$H-NMR (500 MHz, C$_5$D$_5$N) δ 8.86 (bt, J$_{NH,6a}$=J$_{NH,6b}$=5.4 Hz, 2H, NH), 8.59 (d, J$_{5',6'}$=8.5 Hz, 2H, H-6'), 7.60 (d, J$_{2'',3''}$=8.1 Hz, 4H, H-2''), 7.41 (t, J$_{2'',3''}$=J$_{3'',4''}$=7.6 Hz, 4H, H-3''), 7.29 (t, J$_{3'',4''}$=7.4 Hz, 2H, H-4''), 6.86 (s, 2H, H-3'), 6.77 (d, J$_{5',6'}$=8.7 Hz, 2H, H-5'), 5.64 (d, J$_{1,2}$=3.4 Hz, 2H, H-1), 5.31 (s, CH$_2$-O—Bn), 5.07 (m, 2H, H-5), 4.70 (t, J$_{2,3}$=J$_{3,4}$=9.2 Hz, 2H, H-3), 4.62 (m, 2H, H-6a), 4.11 (dd, J$_{2,3}$=9.5 Hz, J$_{1,2}$=3.7 Hz, 2H, H-2), 4.06 (m, 2H, H-6b), 4.01 (t, J$_{3,4}$=J$_{4,5}$=9.4 Hz, 2H, H-4), 3.95 (t, J$_{7',8'}$=6.4 Hz, 4H, H-7'), 1.73 (p, J$_{7',8'}$=J$_{8',9'}$=6.9 Hz, 4H, H-8'), 1.49-1.37 (m, 56H, H-10'-H-23'), 0.88 (t, J$_{23',24'}$=6.8 Hz, 6H, H-24'); $^{13}$C-NMR (125 MHz, C$_5$D$_5$N$_5$) δ 166.7 (C=O), 163.8 (C-4'), 159.1 (C-2'), 137.1 (C-1''), 134.7 (C-6'), 129.7 (C-3''), 129.1 (C-4''), 128.5 (C-2''), 116.1 (C-4'), 107.4 (C-5), 101.5 (C-3'), 96.5 (C-1), 74.7 (C-3), 73.9 (C-2), 73.5 (C-4), 72.5 (C-5), 71.6 (CH$_2$-O—Bn), 69.0 (C-7'), 41.9 (C-6), 32.6, 30.51, 30.49, 30.48, 30.42, 40.41, 30.38, 30.16, 30.12, 29.9, 26.8, 23.4 (C-8'-C-23'), 14.8 (C-24'); HRMS (ESI) m/z [M+H]$^+$ calcd. for [C$_{76}$H$_{116}$N$_2$O$_{15}$+H]$^+$: 1297.8448, obsd. 1297.8442.

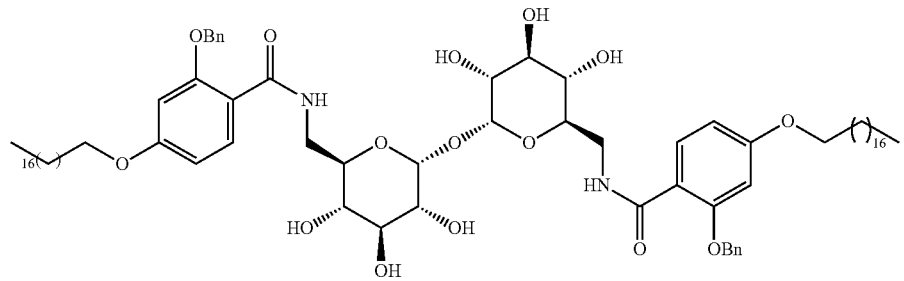

6,6'-Dideoxy-(2-O-benzyl-6-methyl-4-octadecyloxy-benzoylamido)-α,α'-trehalose. 6,6'-Diazido-6,6'-dideoxy-α,α'-trehalose (52 mg, 0.13 mmol), PMe$_3$ (1.3. mL, 1.3 mmol), water (0.15 mL, 8.3 mmol), 2-O-benzyl-6-methyl-octadecyloxy benzoic acid (2.10 mg, 0.41), DIPEA (0.14 mL, 0.80 mmol), and HBTU (155 mg, 0.41 mmol) were subjected to the general procedure for the Staudinger reduction and the coupling reaction. The resultant residue was dissolved in hot tBuOH:EtOAc (50 mL, 2:1, v/v) and washed with 0.1 M HCl (75 mL), sat. NaHCO$_3$ (74 mL), and brine (75 mL). The organic layer was diluted with pyridine (5 mL), dried (MgSO$_4$), filtered and concentrated. The resultant residue was purified by gradient silica gel flash column chromatography (CH$_2$Cl$_2$ to CH$_2$Cl$_2$:MeOH, 9:1, v/v) to give the title compound as a white solid (104 mg, 0.08 mmol, 59%). R$_f$=0.26 (CH$_2$Cl$_2$:MeOH, 85:15, v/v); [α]$_D^{23}$=+28 (c=0.7, pyridine); IR (film) 3333, 2917, 2850, 1605, 1532, 1488, 1467, 1377, 1321, 1281, 1229, 1172, 1145, 1075, 1037, 995, 943, 909, 841, 805 cm$^{-1}$; $^1$H-NMR (500 MHz, C$_5$D$_5$N) δ 9.17 (bt, J$_{NH,6a}$=J$_{NH,6b}$=5.8 Hz, 2H, NH), 7.59 (H-4''), 7.30 (t, J$_{2'',3''}$=J$_{3'',4''}$=7.4 Hz, 4H, H-3''), 7.20 (H-2'' or H-4''), 6.66 (bs, 2H, H-3'), 6.50 (bs, 2H, H-5'), 5.82 (d, J$_{1,2}$=3.3 Hz, 2H, H-1), 5.21 (s, 4H, CH$_2$-O—Bn), 5.06 (m, 2H, H-5), 4.76 (t, J$_{2,3}$=J$_{3,4}$=9.2 Hz, 2H, H-3), 4.56 (m, 2H, H-6a), 4.27-4.17 (m, 6H, H-2, H-4 & H-6b), 3.91 (t, J$_{7',8'}$=6.4 Hz, 4H, H-7'), 2.53 (s, 6'-Me), 1.73 (p, J$_{7',8'}$=J$_{8',9'}$=7.0 Hz, 4H, H-8'), 1.43 (m, 4H, H-9'), 1.35-1.19 (m, 56H, H-10'-H-23'), 0.88 (t, J$_{23',24'}$=6.8 Hz, 6H, H-24'); $^{13}$C-NMR (150 MHz, C$_5$D$_5$N) δ170.0 (C=O), 161.0 (C-4'), 157.5 (C-2'), 138.7, 138.4 (C-1' & C-6'), 129.3, 128.4, 127.8 (C-2'-C-4'), 122.6 (C-1'), 108.7 (C-5'), 99.2 (C-3'), 96.7 (C-1), 74.6 (C-3), 74.0, 73.6 (C-2 & C-4), 73.1 (C-5), 70.7 (CH$_2$-O—Bn), 68.7 (C-8), 42.0 (C-6), 32.6, 30.50, 30.48, 30.47, 30.42, 30.41, 30.2, 30.1 30.0, 26.8, 23.4 (C-9'-C-23'), 20.5 (6'-Me), 14.8 (C-24'); HRMS (ESI) m/z [M+H]$^+$ calcd. for [C$_{78}$H$_{120}$N$_2$O$_{15}$+H]$^+$: 1325.8761, obsd.: 1325.8761.

6,6'-Dideoxy-(2-hydroxy-4-octadecyloxy-benzoylamido)-α,α'-trehalose (43j). To a solution of 6,6'-Dideoxy-di-(2-O-benzyl-4-octadecyloxy-benzoylamido)-α,α'-trehalose (126 mg, 0.10 mmol) in distilled CH$_2$Cl$_2$:MeOH (6 mL, 1:1, v/v) was added Pd(OH)$_2$/C (10 mg). H$_2$ was bubbled through the suspension for 48 h, and then the reaction mixture was diluted with pyridine (15 mL) and filtered over celite. The filtrate was concentrated and the resultant residue purified by gradient silica gel flash column chromatography (CH$_2$Cl$_2$ to CH$_2$Cl$_2$:MeOH, 9:1, v/v) to give the title compound as a white solid (82 mg, 0.07 mmol, 75%). R$_f$=0.37 (CH$_2$Cl$_2$:MeOH, 85:15, v/v); [α]$_D^{20}$=+24 (c=1.0, pyridine); IR (film) 3348, 2917, 2849, 1642, 1616, 1597, 1551, 1534, 1503, 1469, 1438, 1377, 1335, 1275, 1259, 1191, 1179, 1042, 996, 940, 855, 834, 815, 805 cm$^{-1}$; H-NMR (500 MHz, C$_5$D$_5$N) δ 9.18 (bt, J$_{NH,6a}$=J$_{NH,6b}$=5.4 Hz, 2H, NH), 8.28 (d, J$_{5',6'}$=8.8 Hz, 2H, H-6'), 6.82 (d, J$_{3',5'}$=2.1 Hz, 2H, H-3'), 6.59 (dd, J$_{5',6'}$=8.8 Hz, J$_{3',5'}$=2.4 Hz, 2H, H-5), 5.76 (d, J$_{1,2}$=3.6 Hz, 2H, H-1), 5.06 (m, 2H, H-5), 4.67 (t, J$_{2,3}$=13, 4=9.3 Hz, 2H, H-3), 4.28 (m, 4H, H-7'), 4.19 (dd, J$_{2,3}$=9.9 Hz, J$_{1,2}$=3.9 Hz, 2H, H-2), 3.97 (t, J$_{3,4}$=14,5=9.3 Hz, 2H, H-4), 3.93 (m, 4H, H-6a & H-6b), 1.72 (p, J$_{7',8'}$=J$_{8',9'}$=7.0 Hz, 4H, H-8'), 1.41 (m, 4H, H-9'), 1.35-1.21 (m, 56H, H-10'-H-23'), 0.88 (t, J$_{23',24'}$=7.0 Hz, 6H, H-24'); $^{13}$C-NMR (125 MHz, C$_5$D$_5$N) δ 170.3 (C=O), 163.8 (C-1'), 163.2 (C-2'), 129.7 (C-6'), 109.5 (C-4'), 106.7 (C-5), 102.5 (C-3'), 96.3 (C-1), 74.5 (C-3), 73.4 (C-4), 73.2 (C-2), 71.9 (C-5), 68.1 (C-6), 41.5 (C-7'), 31.9, 29.80, 29.79, 29.76, 29.72, 29.69, 29.65, 29.43, 29.41, 29.2, 26.1, 22.7 (C-8'-C-23'), 14.1 (C-24'), HRMS (ESI) m/z [M+H]$^+$ calcd. for [C$_{62}$H$_{104}$N$_2$O$_{15}$+H]$^+$: 1117.7509, obsd. 1117.7513.

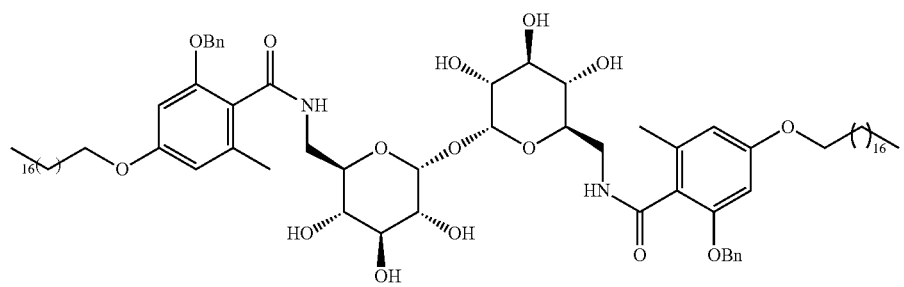

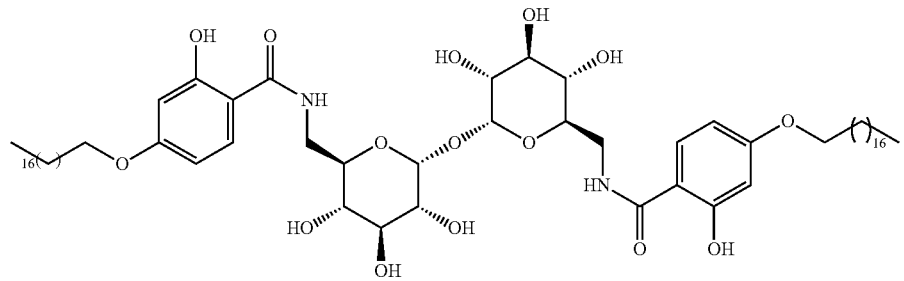

6,6'-Dideoxy-(2-hydroxy-6-methyl-4-octadecyloxy-benzoylamide)-α,α'-trehalose (43k). To a solution of 6,6'-Dideoxy-(2-O-benzyl-6-methyl-4-octadecyloxy-benzoylamido)-α,α'-trehalose (91 mg, 0.07 mmol) in distilled $CH_2Cl_2$:MeOH (6 mL, 1:1, v/v) was added $Pd(OH)_2/C$ (29 mg). $H_2$ was bubbled through the suspension for 20 h, and then the reaction mixture was diluted with pyridine (6 mL) and filtered over celite. The filtrate was concentrated and the resultant residue purified by gradient silica gel flash column chromatography ($CH_2Cl_2$ to $CH_2Cl_2$:MeOH, 4:1, v/v) to give the title compound as a white solid (51 mg, 0.04 mmol, 64%). $R_f$=0.18 ($CH_2Cl_2$:MeOH, 85:15, v/v); $[\alpha]_D^{23}$=+25 (c=1.0, pyridine); IR (film) 3350, 2916, 2849, 2765, 1607, 1539, 1467, 1318, 1275, 1213, 1174, 1144, 1106, 1059, 1037, 992, 945, 835, 804 $cm^{-1}$; $^1$H-NMR (500 MHz, $C_5D_5N$) δ 8.80 (bt, $J_{NH,6a}=J_{NH,6b}$=5.7 Hz, 2H, NH), 6.72 (d, $J_{3',5'}$=2.0 Hz 2H, H-3'), 6.50 (d, $J_{3',5'}$=2.0 2H, H-5), 5.85 (d, $J_{1,2}$=4.1 Hz, 2H, H-1), 5.09 (dt, $J_{4,5}$=10.0 Hz, $J_{5,6a}=J_{5,6b}$=4.8 Hz, 2H, H-5), 4.72 (t, $J_{2,3}=J_{3,4}$=9.4 Hz, 2H, H-3), 4.34 (m, 4H, H-6a & H-6b), 4.23 (dd, $J_{2,3}$=9.6 Hz, $J_{1,2}$=3.7 Hz, 2H, H-2), 4.11 (t, $J_{3,4}$=14,5=9.3 Hz, 2H, H-4), 3.94 (t, $J_{7',8'}$=6.2 Hz, 4H, H-7'), 2.70 (s, 6H, 6'-Me), 1.73 (p, $J_{7',8'}=J_{8',9'}$=6.8 Hz, 4H, H-8'), 1.41 (bp, $J_{8',9'}=J_{9',10'}$=7.0 Hz, 4H, H-9') 1.31-1.28 (m, 52H, H-10'-H-23'), 0.88 (t, $J_{23',24'}$=6.8 Hz, 6H, H-24'); 170.8 (C=O), 161.8 (C-4'), 160.3 (C-2'), 139.8 (C-6'), 116.8 (C-1'), 109.4 (C-5), 101.1 (C-3'), 96.8 (C-1), 74.9 (C-3), 74.2 (C-4), 73.9 (C-2), 72.7 (C-5), 68.5 (C-7'), 42.5 (C-6), 32.6, 30.48, 30.47, 30.46, 30.40, 30.39, 30.36, 30.2, 30.1, 30.0, 26.8 (C-8' and C-10'-C-23'), 23.4 (C-9') 22.2 (6'-Me), 14.8 (C-24'); HRMS (ESI) m/z [M+H]⁺ calcd. for: $[C_{64}H_{108}N_2O_{15}+H]^+$: 1145.7822, obsd.: 1145.7822.

iPrOH, or the p-$OC_{18}H_{37}$ substituted analogue, 9f. Reporter cell activation was measured by the production of NFAT-GFP, which was analysed by flow cytometry. On the whole, all brartemicin analogues strongly activated both the hMincle and mMincle expressing reporter cells, with all derivatives inducing comparable levels of NFAT-GFP to p-$OC_{18}$ (9f) and TDB. At the amount of 0.1 nmol/well, both o-$OC_{18}$ (43a) and m-$OC_{18}$ (43b) induced the reporter cells to produce comparatively more NFAT-GFP than p-$OC_{18}$ (30h), with the most potent response being observed for the o-substituted derivative 43a. At all tested concentrations, the branched brartemicin derivative 43c, dihydrocinnamate derivative 43d, cinnamate derivative 43e, carbon-linked derivative 43f, amine-linked analogue 43g, and sulphur-linked derivative 43h induced hMincle and mMincle expressing reporter cells to produce levels of NFAT-GFP similar to that produced by the cells in response to TDB. Taken together, this data highlights the capacity of Mincle to tolerate changes to the structure of brartemicin analogues, with o-$OC_{18}$ (43a) inducing the reporter cells to produce more NFAT-GFP than the other derivatives.

Example 9: Activation of GM-CSF BMDMs

To gain insight into the capacity of the 2G-series of brartemicin analogues to induce an inflammatory immune response, the analogues were then screened for their ability to activate WT and Mincle⁻/⁻ BMDMs, with cellular activation being determined by the measurement of IL-1B using ELISA (FIG. 6). Here, all brartemicin analogues (43a-h) stimulated WT BMDMs to produce appreciable quantities of

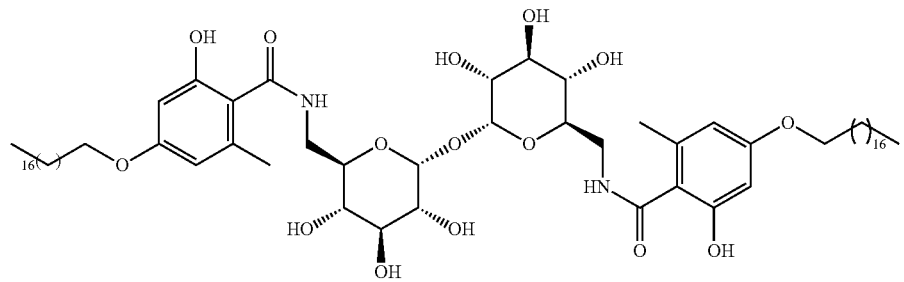

Example 8: Activation of NFAT-Mincle Reporter Cells

With the compounds 43a-h in hand, the ability of these analogues to bind and signal through Mincle was assessed (FIG. 5). Accordingly, NFAT-GFP reporter cells expressing mMincle+FcRγ, hMincle+FcRγ, or FcRγ-only were stimulated with the 2G-brartemicin analogues 43a-h, TDB, IL-1β, with the m-substituted derivative 43b, dihydrocinnamate derivative 43d, cinnamate derivative 43e, carbon-linked analogue 43f, and sulphur-linked derivative 43h inducing approximately equal amounts of IL-11 compared to p-$OC_{18}$ (9f) and TDB (FIG. 2a). Furthermore, stimulation of Mincle⁻/⁻ BMDMs with analogues 43b, 43d-f, and 43h resulted in no substantial production of IL-1β, which indicated that Mincle is the receptor primarily responsible for mediating BMDM activation by these compounds (FIG. 6b).

7. REFERENCES

Khan A A, Chee S H, McLaughlin R J, Harper J L, Kamena F, Timmer M S M, Stocker B L (2011) Long-chain lipids are required for the innate immune recognition of trehalose diesters by macrophages. *ChemBioChem* 12(17): 2572-2576.

Carta F, Vullo D, Maresca A, Scozzafava A, Supuran C T (2013) Mono-/dihydroxybenzoic acid esters and phenol pyridinium derivatives as inhibitors of the mammalian carbonic anhydrase isoforms I, II, VII, IX, XII and XIV. *Bioorg Med Chem* 21(6):1564-1569.

Baird L J, Timmer M S, Teesdale-Spittle P H, Harvey J E (2009) Total synthesis of aigialomycin D using a Ramberg-Backlund/RCM strategy. *J Org Chem* 74(6):2271-2277.

Gram G J, Karlsson I, Agger E M, Andersen P, Fomsgaard A (2009) A novel liposome-based adjuvant CAF01 for induction of CD8(+) cytotoxic T-lymphocytes (CTL) to HIV-1 minimal CTL peptides in HLA-A*0201 transgenic mice. *PloS ONE* 4(9):e6950.

The invention claimed is:
1. A compound of Formula IVb

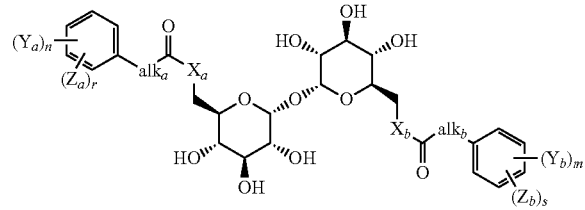

Formula IVb wherein $X_a$ and $X_b$ are independently selected from O or NH;

each $Y_a$ and $Y_b$ is independently selected from the group comprising —I, —Br, —Cl, —F, —OH, —$R^1$ and —$OR^1$ where $R^1$ is selected from ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl and ($C_2$-$C_6$)alkynyl are each optionally substituted with —OH or ($C_1$-$C_6$)alkoxy;

n and m are independently 0 to 4;

each $Z_a$ and $Z_b$ is independently selected from $R^2$, —$OR^2$, —$NHR^2$, —NHC(O)—$R^2$ and —S—$R^2$, where $R^2$ is selected from ($C_5$-$C_{26}$)alkyl, ($C_5$-$C_{26}$)alkenyl and ($C_5$-$C_{26}$)alkynyl, wherein ($C_5$-$C_{26}$)alkyl, ($C_5$-$C_{26}$)alkenyl and ($C_5$-$C_{26}$)alkynyl are each optionally substituted with —OH or ($C_1$-$C_6$)alkoxy;

r and s are independently 1 to 3;

$alk_a$ and $alk_b$ are absent such that the aryl ring connects directly to the C(O) carbon;

wherein n+r=1 to 5; and m+s=1 to 5.

2. A compound of claim 1 wherein $X_a$ and $X_b$ are both O.

3. A compound of claim 1 wherein $X_a$ and $X_b$ are both NH.

4. A compound of claim 1 wherein n and m are 0 to 3 and each of $Y_a$ and $Y_b$ are independently selected from —OH, —$R^1$ and —$OR^1$ where $R^1$ is selected from ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl and ($C_2$-$C_6$)alkynyl are each optionally substituted with —OH or ($C_1$-$C_6$)alkoxy.

5. A compound of claim 4 wherein each of $Y_a$ and $Y_b$ are independently selected from —OH and —($C_1$-$C_6$)alkyl.

6. A compound of claim 4 wherein n and m are both 1.

7. A compound of claim 1 wherein n and m are both 1 and $Y_a$ and $Y_b$ are independently selected from —OH and methyl.

8. A compound of claim 1 wherein each of $Z_a$ and $Z_b$ are independently selected from $R^2$ and —$OR^2$, where $R^2$ is selected from ($C_5$-$C_{26}$)alkyl, ($C_5$-$C_{26}$)alkenyl and ($C_5$-$C_{26}$)alkynyl, wherein ($C_5$-$C_{26}$)alkyl, ($C_5$-$C_{26}$)alkenyl and ($C_5$-$C_{26}$)alkynyl are each optionally substituted with —OH or ($C_1$-$C_6$)alkoxy.

9. A compound of claim 1 wherein each of $Z_a$ and $Z_b$ are independently selected from $R^2$, —$OR^2$, —$NHR^2$ and —S—$R^2$, where $R^2$ is selected from ($C_5$-$C_{26}$)alkyl, ($C_5$-$C_{26}$)alkenyl and ($C_5$-$C_{26}$)alkynyl.

10. A compound of claim 1 wherein r and s are both 1.

11. A pharmaceutical composition comprising a compound of claim 1 and one or more pharmaceutical acceptable excipients.

12. A method of enhancing an immune response in a subject, the method comprising administering to the subject a therapeutically effective amount of a compound of claim 1.

13. A method of enhancing an immune response to an antigen in a subject, the method comprising administering to the subject a therapeutically effective amount of a compound of claim 1, in conjunction with the antigen.

14. A method of inducing or enhancing Th1-medicated immunity in a subject, the method providing administering to the subject a therapeutically effective amount of a compound of claim 1.

15. A method of inducing or enhancing Th1-medicated immunity in a subject to an antigen, the method providing administering to the subject a therapeutically effective amount of a compound of claim 1, simultaneously, sequentially or separately with the antigen.

* * * * *